United States Patent [19]

Dower et al.

[11] Patent Number: 5,017,795
[45] Date of Patent: May 21, 1991

[54] APPARATUS FOR INSPECTING CAN SEAMS AND THE LIKE

[76] Inventors: Roger G. Dower, 501-5775 Toronto Road, Vancouver, British Columbia, Canada, V6N 3N6; Robert W. Acres, 606-1080 Pacific Street, Vancouver, British Columbia, Canada, V6E 4C2; Harold R. Davis, 4065 West 13th Avenue, Vancouver, British Columbia, Canada, V6R 2T3; Andrew N. Donham, 309-8400 Lansdowne Road, Richmond, British Columbia, Canada, V6X 3G3; Nader Riahi, 101-8751 Citation Drive, Richmond, British Columbia, Canada, V6Y 2Y5; Richard W. A. Slamka, 644 East 52nd Avenue, Vancouver, British Columbia, Canada, V5X 1G8; Lechoslaw K. Urbaniak, 154-9451 Prince Charles Boulevard, Surrey, British Columbia, Canada, V3V 7G1

[21] Appl. No.: 519,322

[22] Filed: May 7, 1990

Related U.S. Application Data

[63] Continuation of Ser. No. 320,004, Mar. 6, 1989, abandoned.

[30] Foreign Application Priority Data

Mar. 7, 1988 [CA] Canada .................................. 560755

[51] Int. Cl.⁵ .......................................... G01N 21/86
[52] U.S. Cl. ..................................... 250/560; 356/385
[58] Field of Search ............... 250/560, 561, 562, 571, 250/572; 356/376, 384, 385, 386, 387

[56] References Cited

U.S. PATENT DOCUMENTS 4,555,633 11/1985 Bjorkelund ........................ 356/385
4,798,963 1/1989 Wittkopp et al. .................. 250/560

OTHER PUBLICATIONS

Wang, "White Light Seam Tracking System for Arc-Welding Robot," SPIE, vol. 850 Optics, Illumination, and Image Sensing for Machine Vision II (1987), pp. 101-107.
Goebbels, "Automation of Surface Defect Detection and Evaluation," SPIE, vol. 849, Automated Inspection and High Speed Vision Architectures (1987), pp. 117-124.
*Optical Sensing for Process Control*, Excerpt from Text, Section 7.5.2, "Active Optical Sensors for Robotic Welding Monitoring," pp. 451-457.

*Primary Examiner*—David C. Nelms
*Attorney, Agent, or Firm*—Klarquist, Sparkman, Campbell, Leigh, & Whinston

[57] ABSTRACT

Apparatus is disclosed for detecting irregularities or flaws in seams such as the seams of cans. The apparatus includes means for irradiating the surface of the seam to produce reflected radiation signals, a plurality of radiation sensors, each having a selected field of view of the surface, and each producing sensor output signals dependent on reflected radiation signals received within such field of view. A signal processing means receives sensor output signals for a succession of fields of view along the longitudinal length of the seam and derives therefrom signal data representing a dimensional feature of the seam. Signl comparison means compares such derived data with signal data representing an acceptable dimensional limit and produces a rejection signal in the event that the dimensional feature does not fall within the limit. Means for classifying the nature of an irregularity is also disclosed, as is transport means for the movement of seams though the field of view of the sensors.

13 Claims, 80 Drawing Sheets

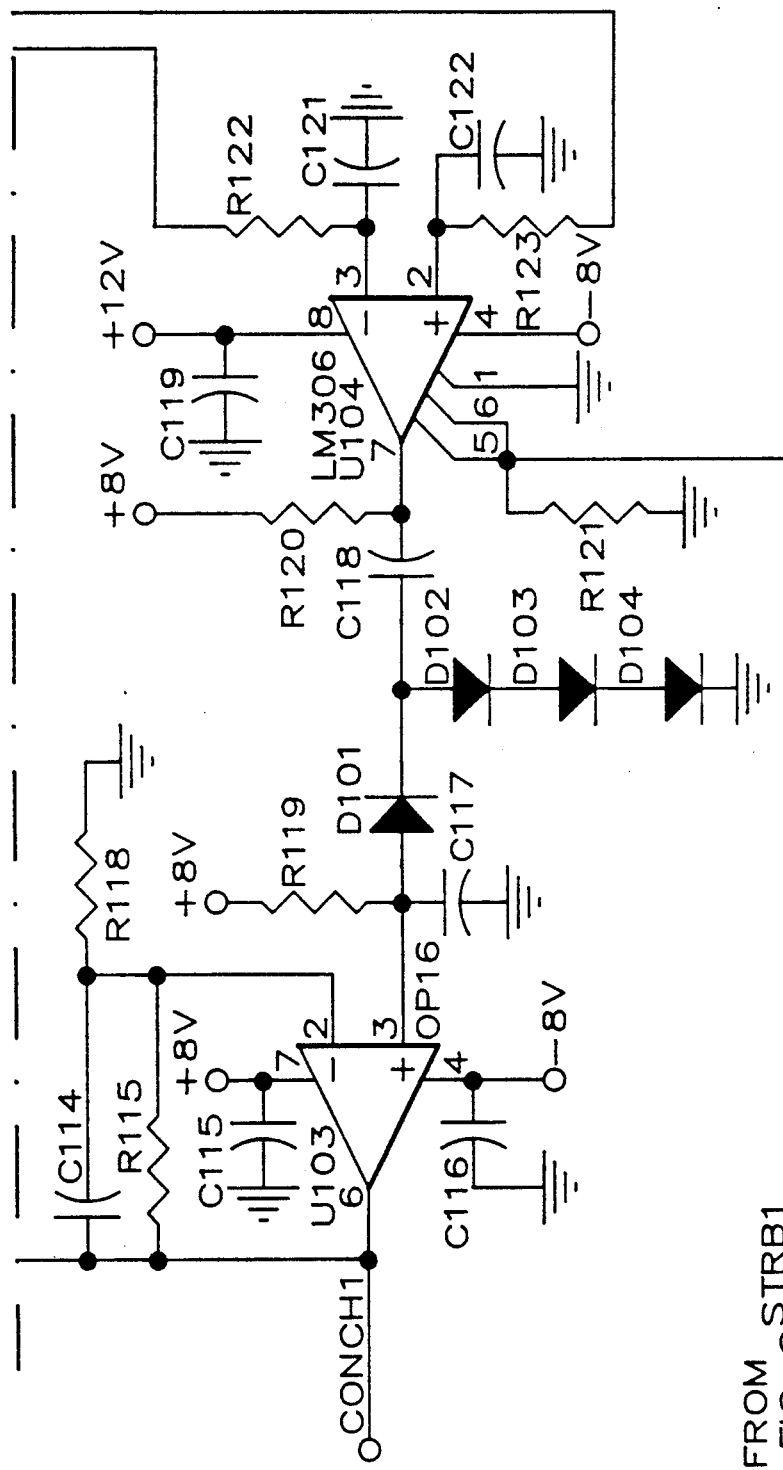
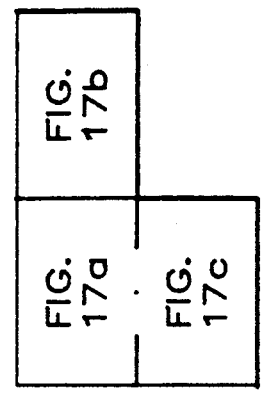
FIG. 17d
FIG. 17c

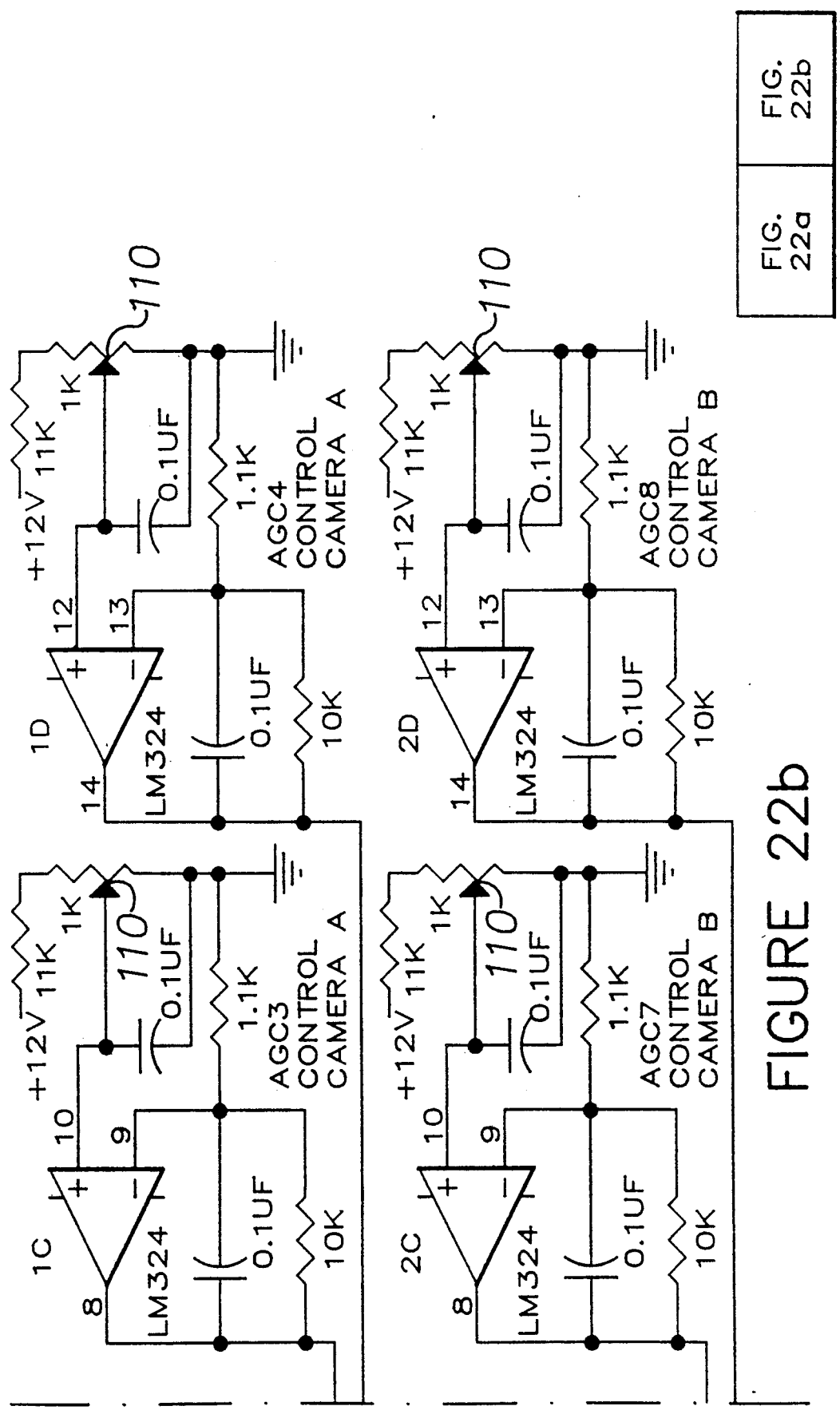

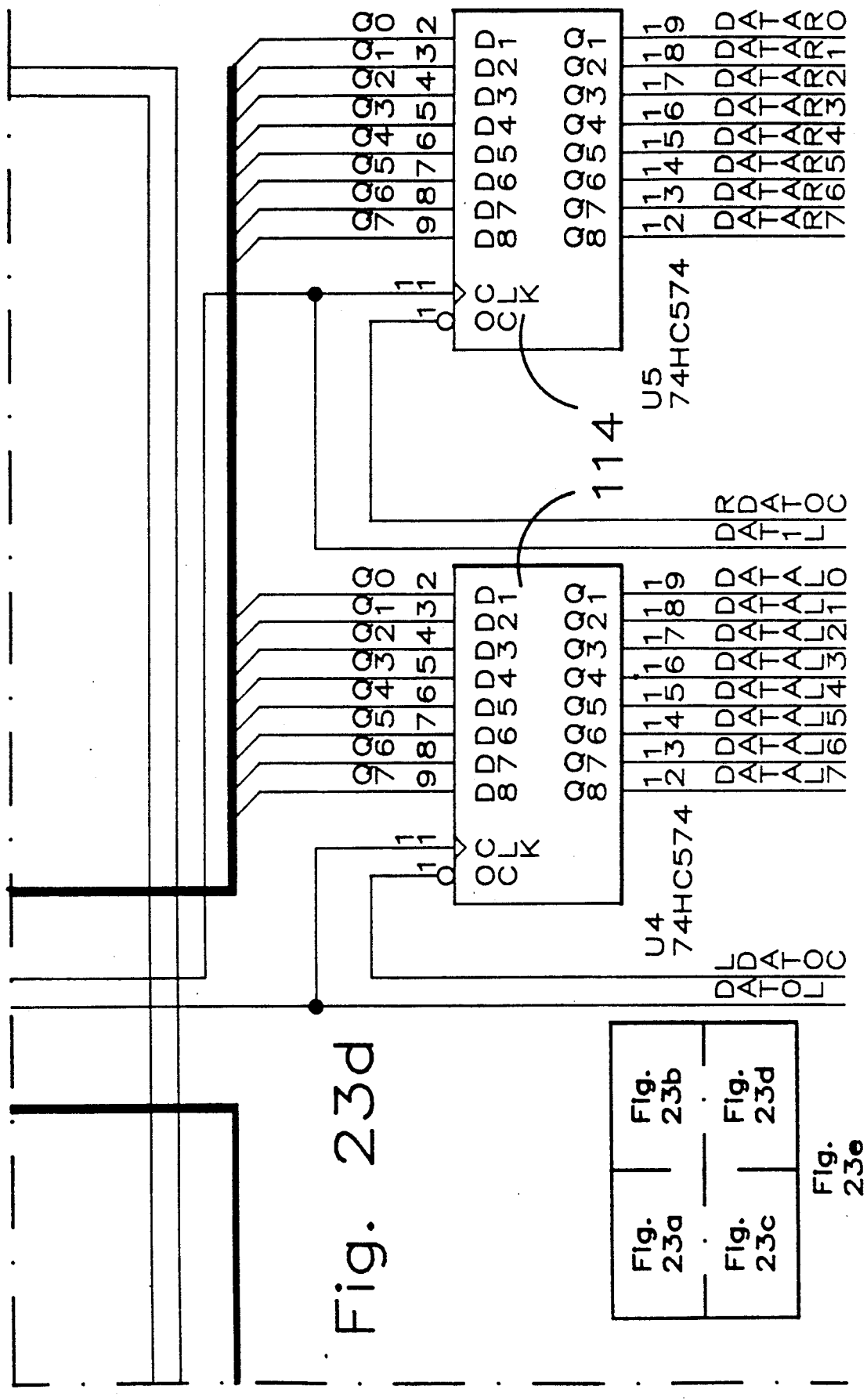

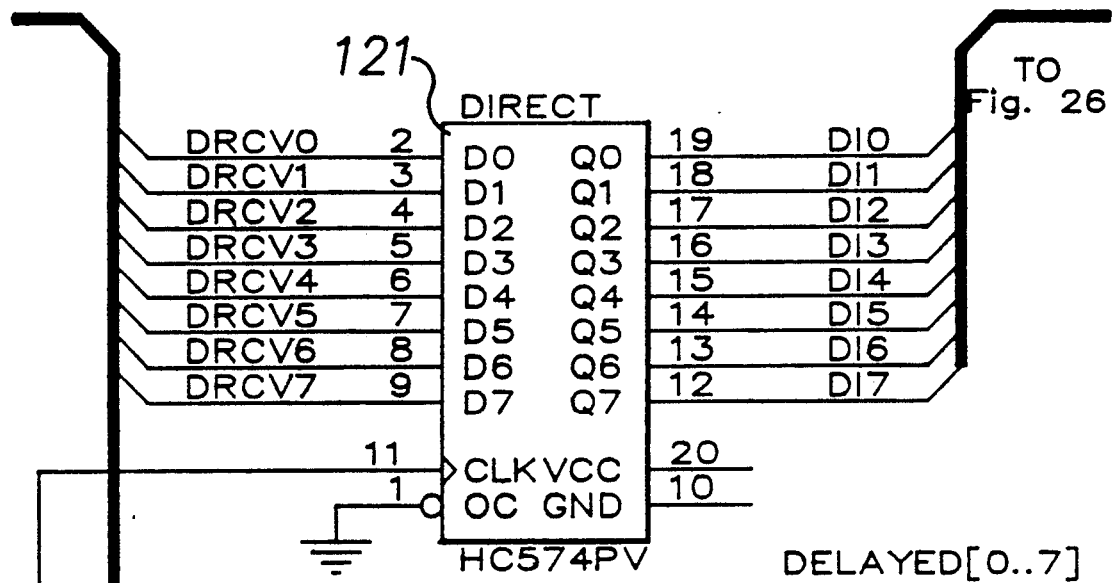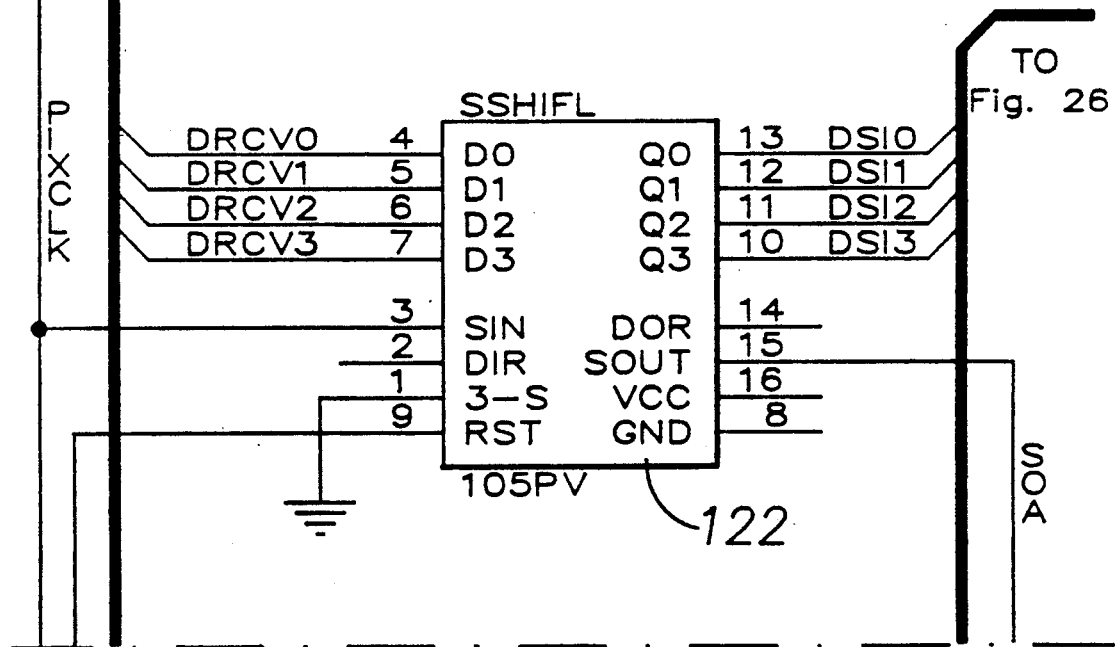
Fig. 25a

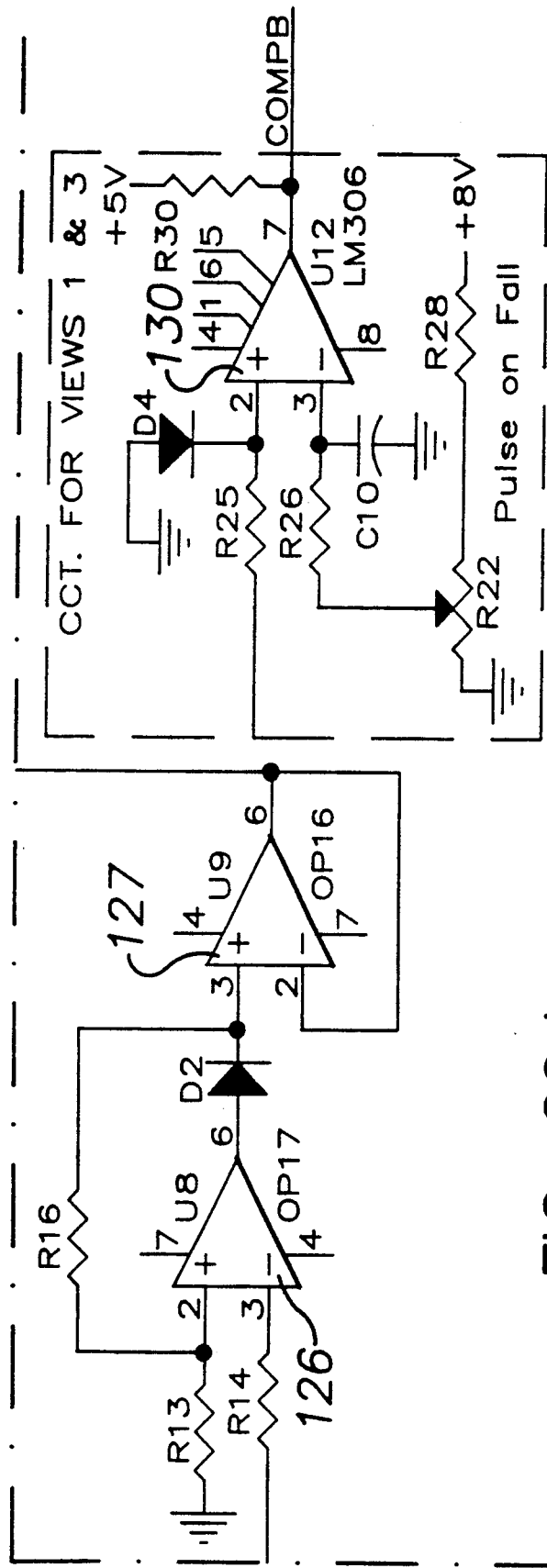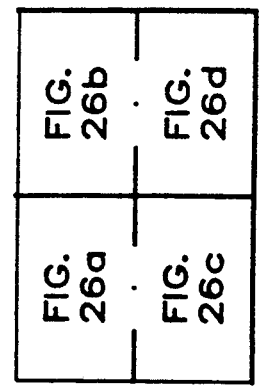
FIG. 26d
FIG. 26e

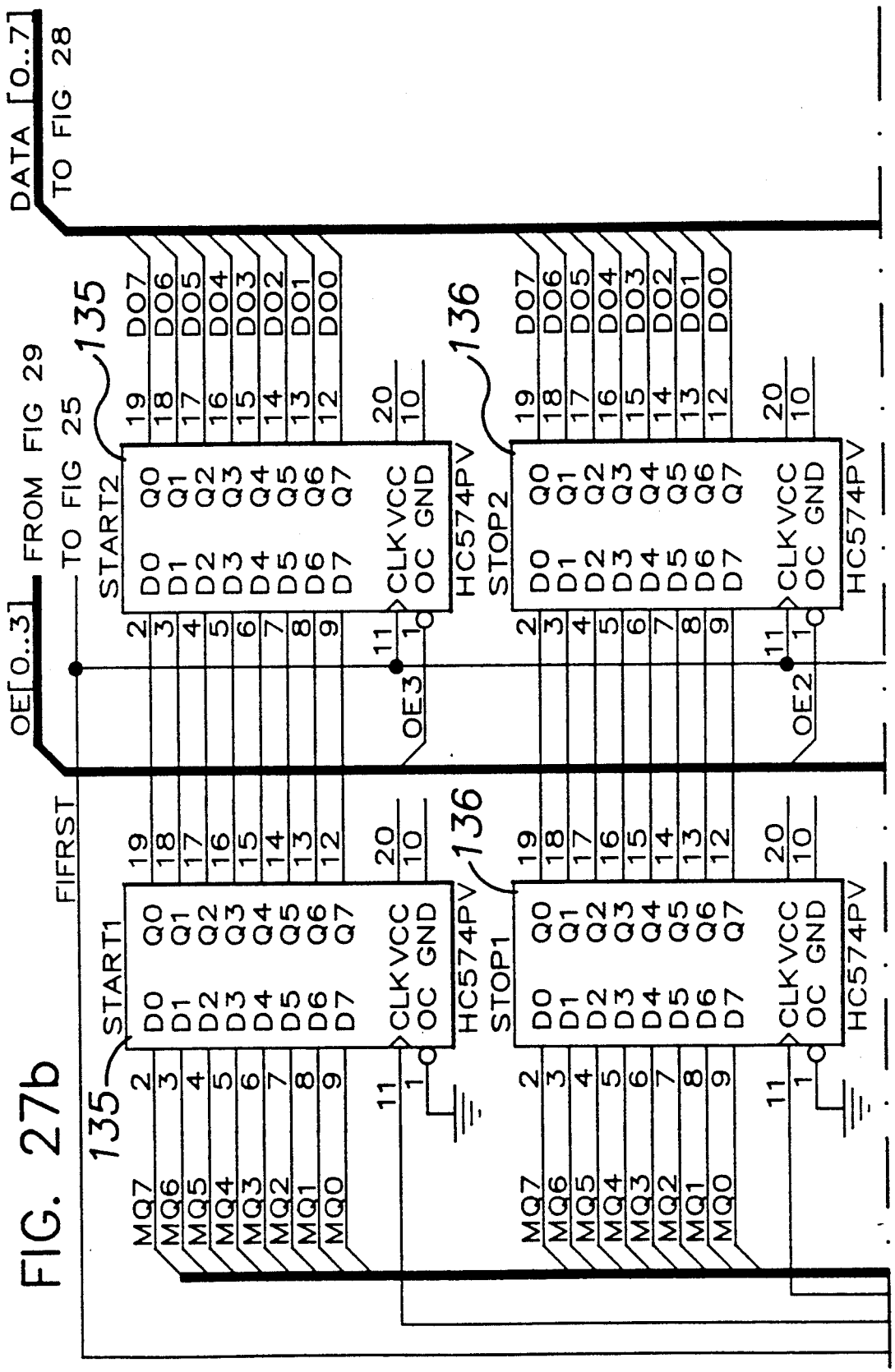

APPARATUS FOR INSPECTING CAN SEAMS AND THE LIKE

This application is a continuation of application Ser. No. 07/320,004, filled on Mar. 6, 1989 now abandoned.

FIELD OF THE INVENTION

This invention relates to apparatus for detecting irregularity in seams, and is especially suited for the inspection of curvate seam structures as are frequently used in the sealing of food cans.

BACKGROUND OF THE INVENTION

A considerable amount of food is preserved using sealed metal cans. Many of such cans will be sealed by joining the lid and the body of the can by a "double seam" which forms a rim or flange circumferentially around the top of the can. Typically, after the can has been filled, the sealing operation is performed in a partial vacuum by rolling the metal of the lid and the body tightly together with a small amount of sealing compound.

While the technology for sealing cans is well developed, a variety of flaws or faults (herein referred to as "irregularities") in the resulting seam can occur; for example: cracks, knocked down rims, false seams, droop, and the like. Since the integrity of the seam can be crucial to the avoidance of spoilage and preservation of food within the can, it becomes highly desirable to provide a means of inspecting cans against the occurrence of such irregularities.

Historically, canners have sought to assure seam integrity by a variety of means, the most basic being manual inspection by the human eye. Of course, the manual approach may only suffice for relatively gross defects that can be easily seen by an inspector, and then only so long as he or she pays constant attention to the matter at hand. Furthermore, the manual approach can be compromised by high speed canning lines where it is impractical to manually inspect every can. To circumvent this limitation, methods have been developed to manually accept or reject batches of cans on the basis of statistical sampling techniques.

Automatic equipment used for the purpose of can inspection is frequently based on the assumption that a properly sealed can will have a partial vacuum. If a seal is faulty, then air leakage will reduce deflection of the can lid. Thus, so called "dud detectors" measure can end deflection, rejecting those cans where the measured deflection is not within prescribed limits. The prior art reveals a variation in which a can is struck electromagnetically, and the vibrations induced in the can used as an indicator of proper pressure.

There are significant problems with this general approach. Measurements of can deflection can be influenced by a variety of factors, including metal thickness of the can ends, the strength of the vacuum applied during canning, the amount and firmness of the fill, and the countersink depth as a result of settings for the seam rollers on the canning machine. In addition, a flaw has to be relatively serious for leakage to occur during the typically brief time that a can spends on the processing line. Many types of flaws may not lead to significant leakage until later. Research has shown that even relatively small problems in the seam may lead to leakage and that multiple minor impacts can be as significant as one major blow.

SUMMARY OF THE INVENTION

The present invention has its foundation in machine vision technology.

In a broad aspect of the present invention, there is provided apparatus for detecting an irregularity in the surface of an elongated seam having a curvate surface cross-section (as is typical of a can seam), such apparatus comprising irradiating means for irradiating the surface to produce reflected radiation signals, and a plurality of sensors, each being disposed to have a selected field of view of the surface, each such view being defined by a width extending longitudinally of the seam and a length curvately extending in a plane transverse to the longitudinal direction of the seam. Each such sensor receives such portion of the reflected radiation signals as are reflected within its corresponding field of view, and produces corresponding sensor output signals in response. A signal processing means receives the sensor output signals for a succession of fields of view along the seam for each such sensor, and derives therefrom signal data representing one or more dimensional features of the seam. A signal comparison means compares such signal data with signal data representing an acceptable dimensional limit or limits, and produces a rejection signal in the event that a dimensional feature of interest does not fall within its prescribed limit.

Advantageously, signal data representing an acceptable dimensional limit for a given seam may be derived by the signal processing means from the sensor output signals produced for that seam. This approach where the dimensional limits are dynamically determined from one seam to the next may be contrasted with an approach where acceptable dimensional limits are fixed and predefined without regard to the fact that a succession of ostensibly identical seams, each being a completely acceptable seam, may nevertheless exhibit dimensional differences. Such differences may not be attributable to any unacceptable irregularity in the seam, but simply to acceptable tolerance variations from one seam to the next. With the dynamic approach, it becomes possible to effectively mask or filter out the effect of such variations.

In one embodiment of the present invention when used for the inspection of can seams, a transport means is included for rotating a can to longitudinally move its seam through the field of view of the sensor. Preferably, such transport means comprises an inspection rotor and means for rotating the rotor about a fixed vertically extending central axis. The sensors are mounted to the rotor so as to rotate therewith. A rotatable inspection platform is also mounted to the rotor to support the can in an upright position radially away from the central axis, and means are provided to rotate the platform (with the can) in a direction of rotation opposite to that of the rotor (doing so about a planetary axis extending parallel to the central axis of the rotor). As will become more apparent hereinafter, this arrangement permits a reduction in the degree of can rotation required to pass the full circumferential length of its seam through the field of view of the sensors—a desirable feature in situations where excessive high speed spinning of a can may be considered undesirable (e.g. as potentially damaging to the structure of food within the can).

In a preferred embodiment of the present invention, four sensors are used to obtain image data on dimensional features of the seam or double seam of a can. One sensor views the seam from an angle looking upwardly and radially inwardly at the seam; another from an angle looking horizontally inwardly at the seam; another from an angle looking vertically downwardly at the seam; and the last from an angle looking downwardly and radially outwardly at the seam. So positioned, a substantial portion of the exposed surface area of the seam may be brought within the combined field of view of the sensors. Image data may be read from each of the sensors simultaneously.

The foregoing and other features of the present invention will now be described with reference to the drawings in which:

BRIEF DESCRIPTIONS OF THE DRAWINGS

Figure 12:
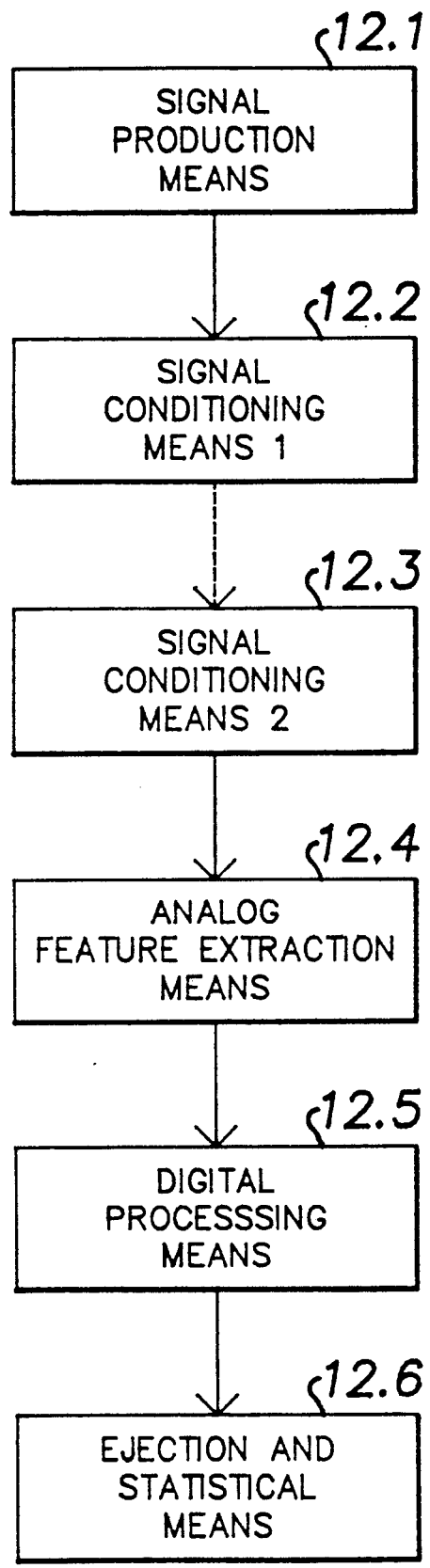
FIG. 12 is a block diagram of the signal processing portions of a preferred embodiment of the invention.
Figure 14A:
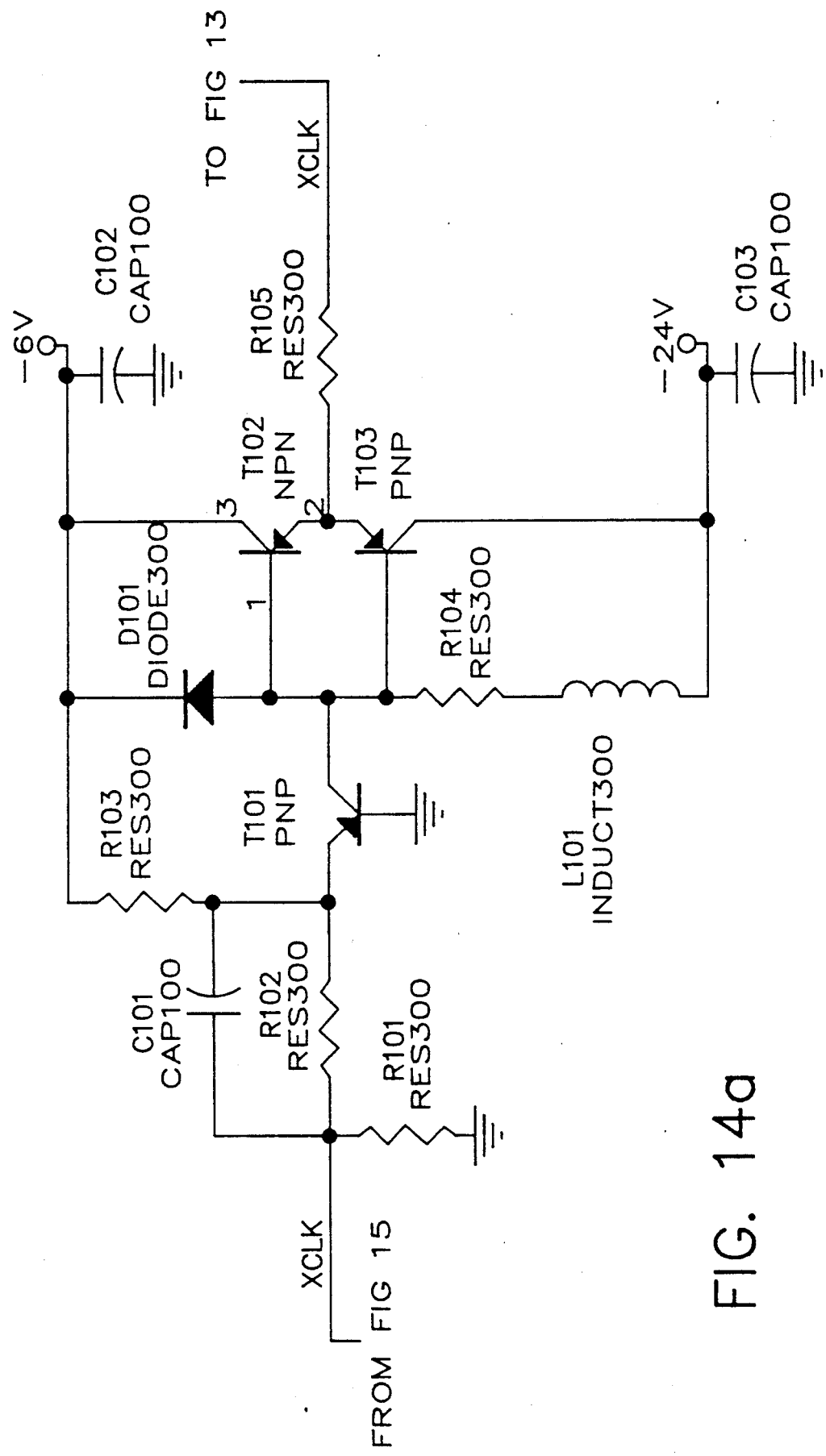
Figure 14B:
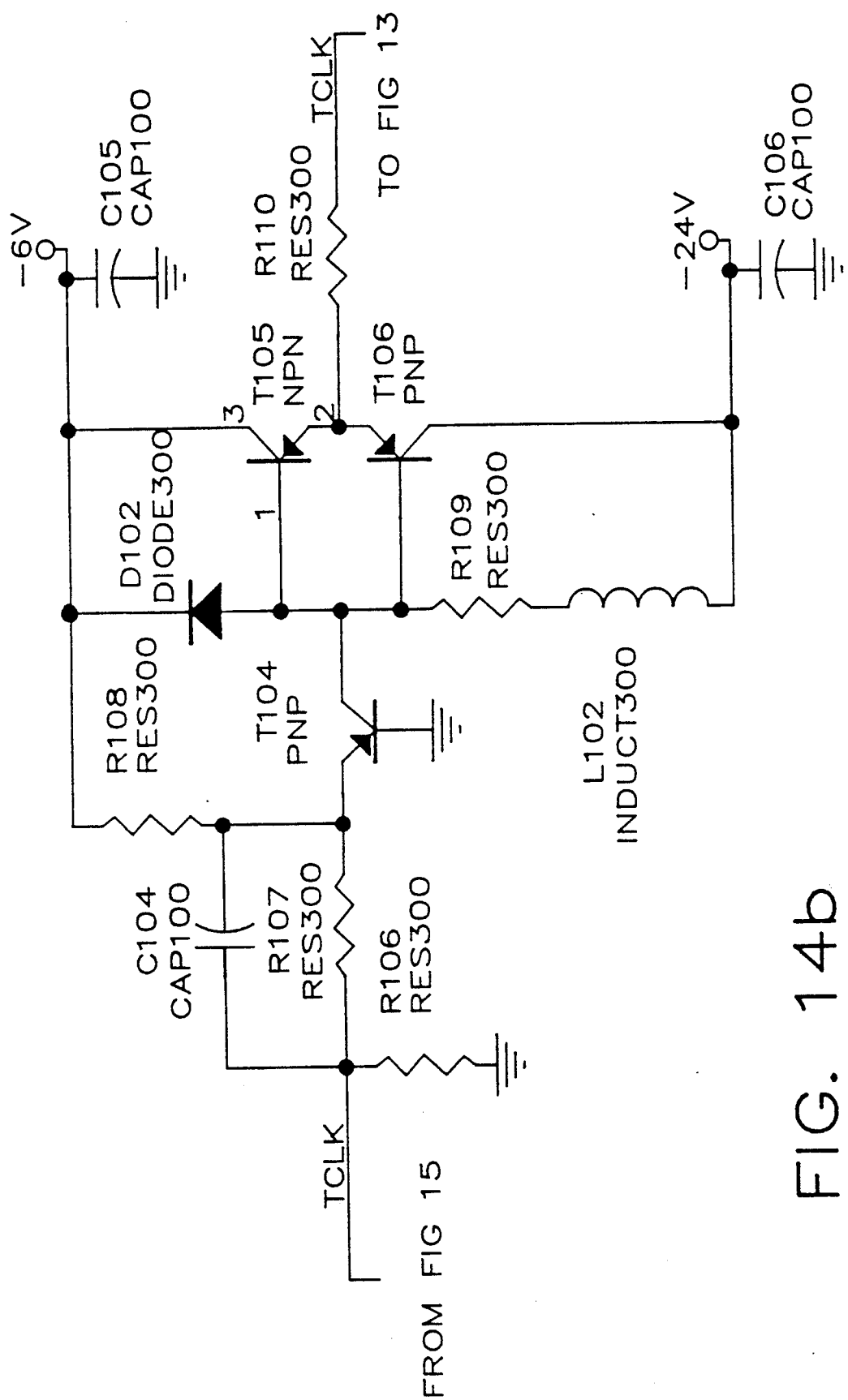
Figure 14C:
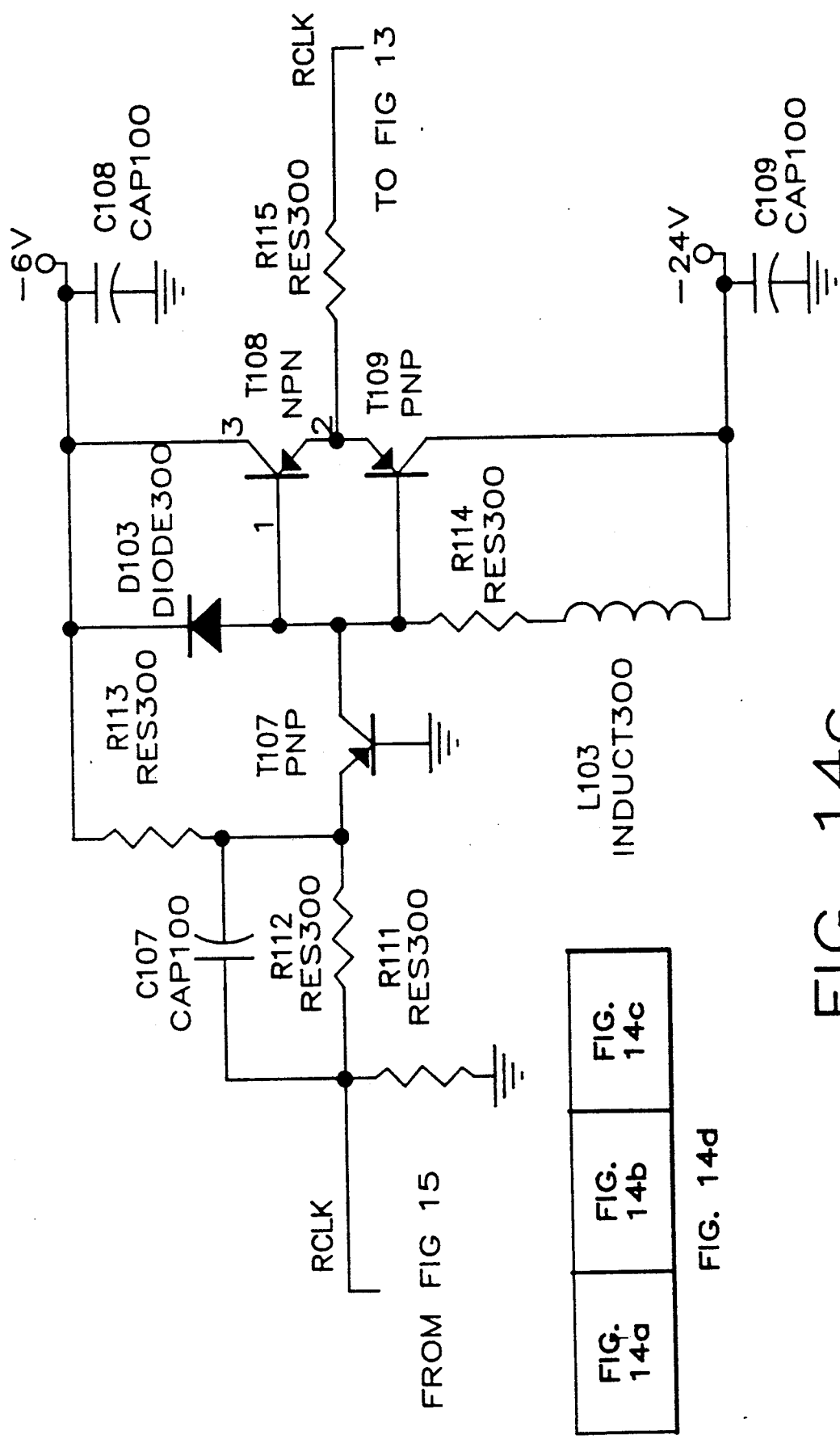

FIGS. 14a to 14 c, assembled as shown in FIG. 14d, and collectively referred to herein as FIG. 14, show in more detail part of the Signal Production Means of FIG. 12; circuitry for driving CCD timing signals.

Figure 15:
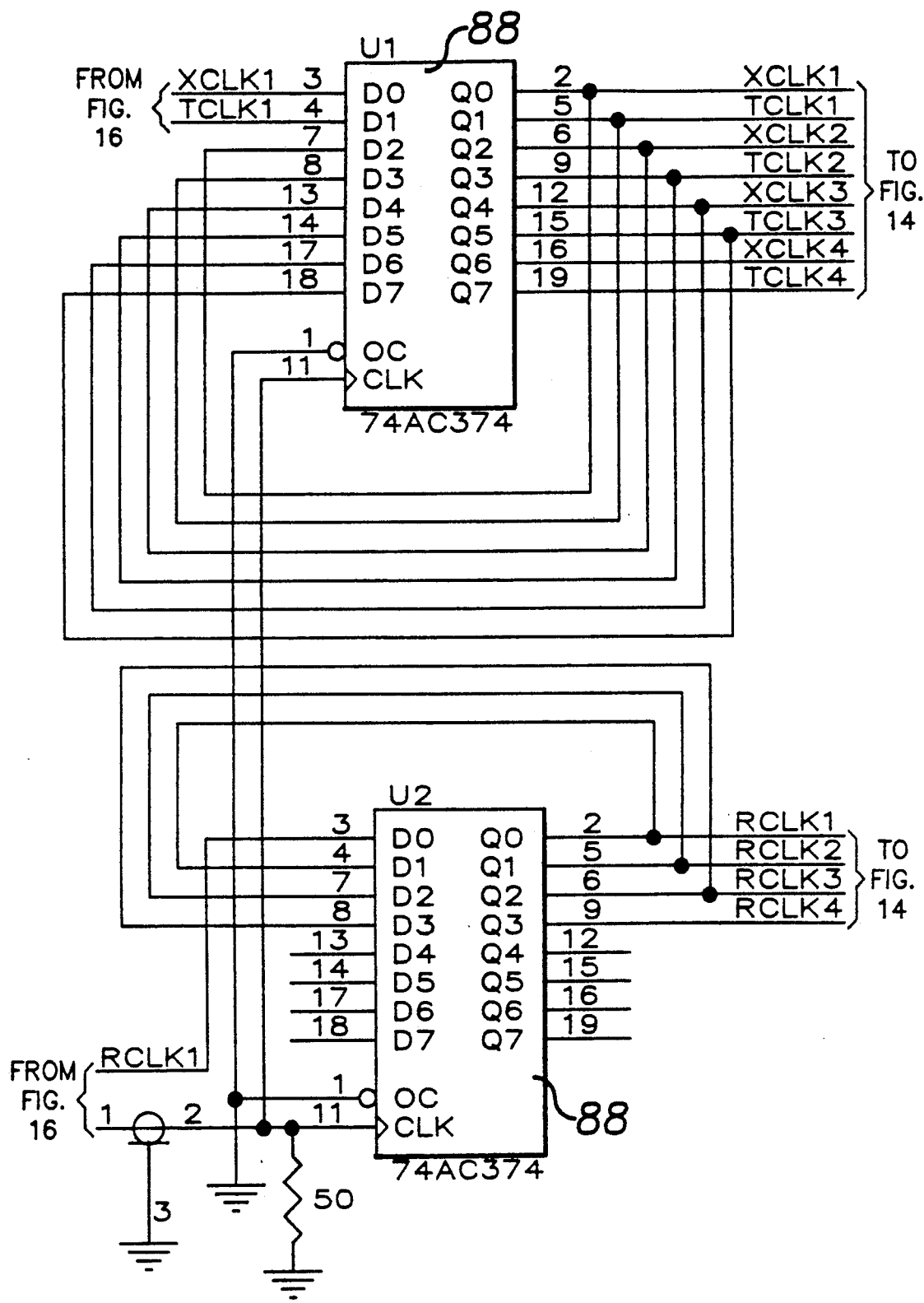

FIG. 15 shows in more detail part of the Signal Production Means of FIG. 12; circuitry for distributing CCD timing signals.

Figure 16A:
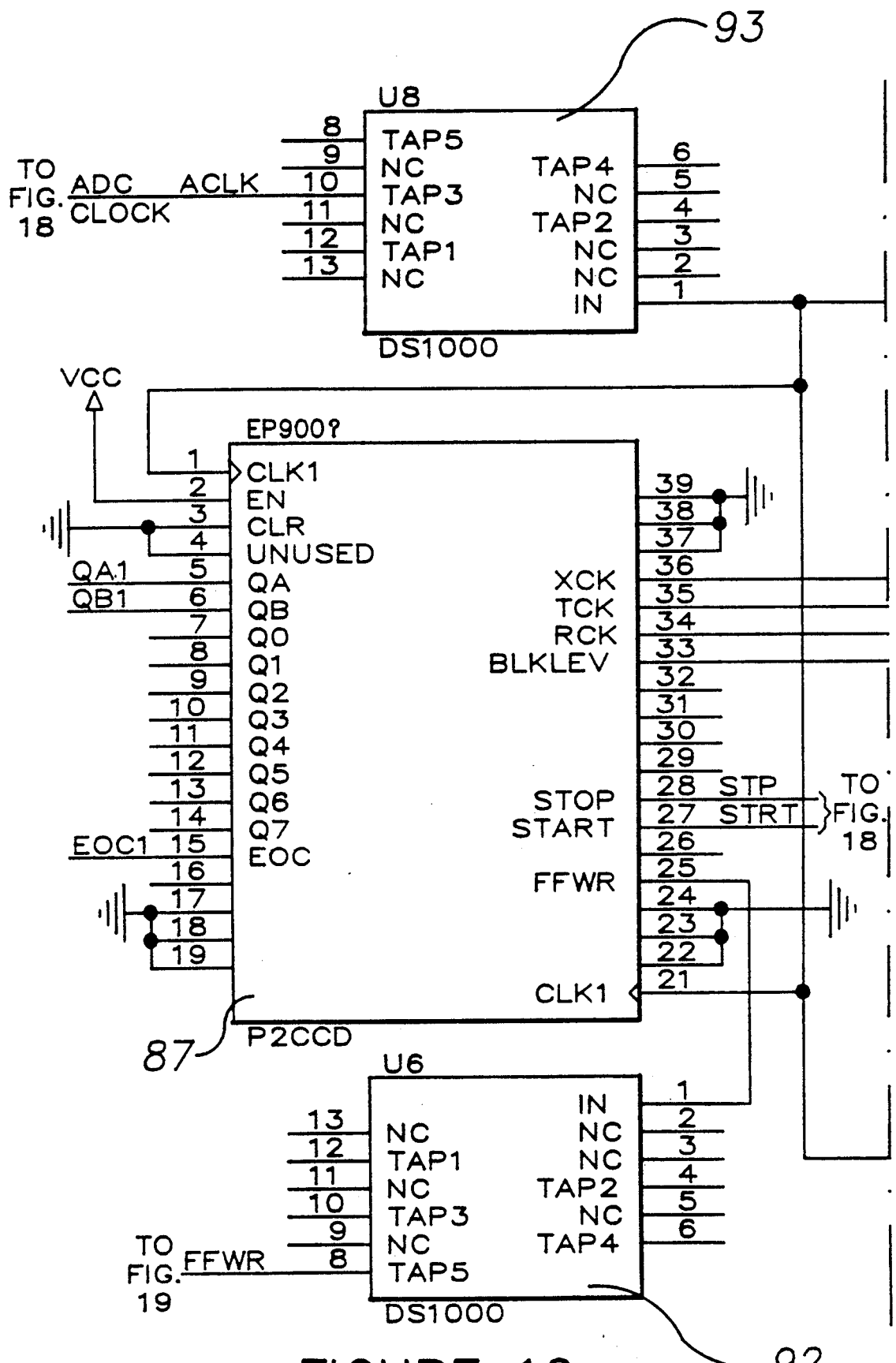
Figures 16B, 16C:
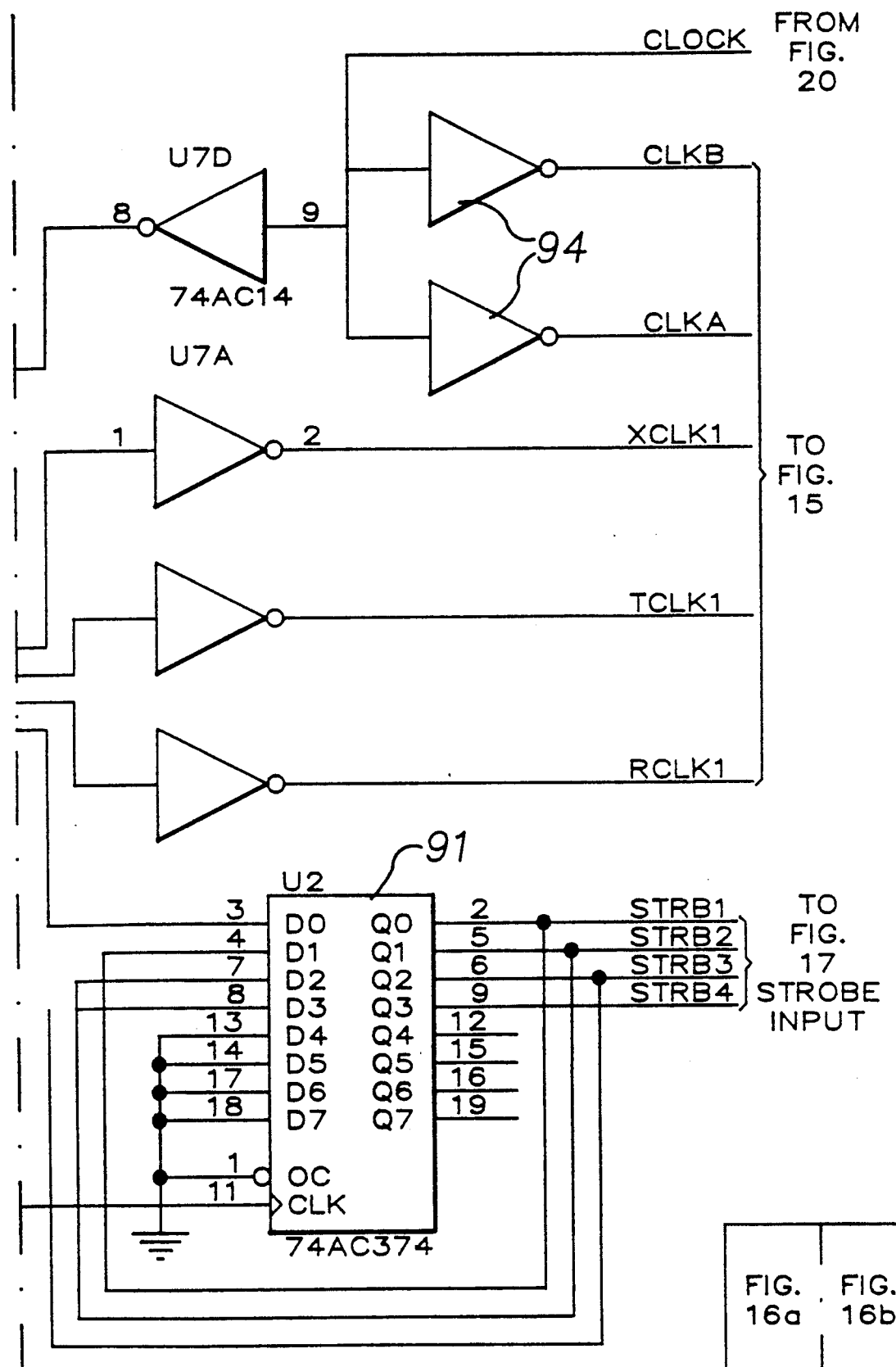

FIGS. 16a to 16b, assembled as shown in FIG. 16c, and collectively referred to herein as FIG. 16, show in more detail part of the Signal Procuction Means 1 of FIG. 12; control signal generation for the CCDs.

Figure 17A:
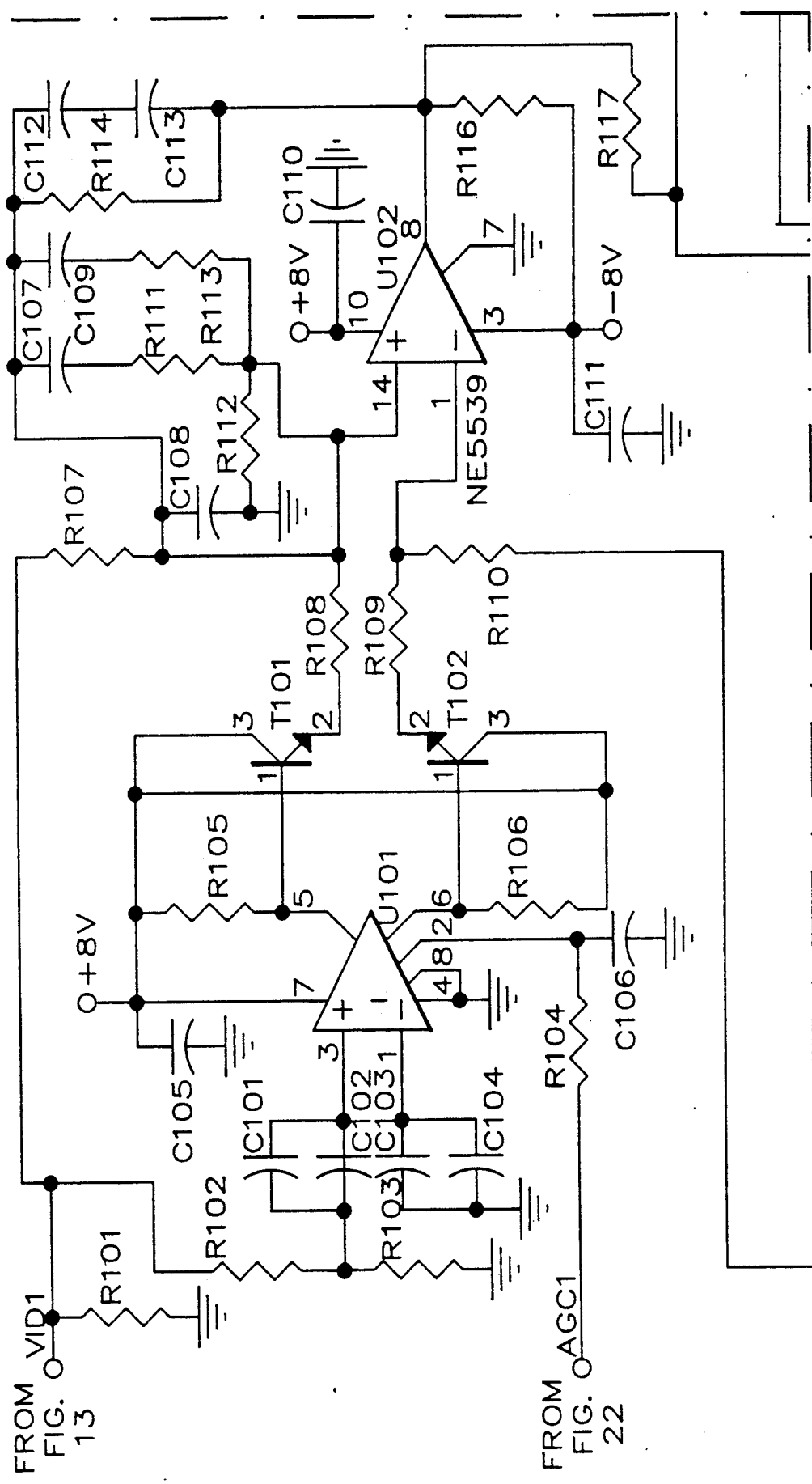
Figure 17B:
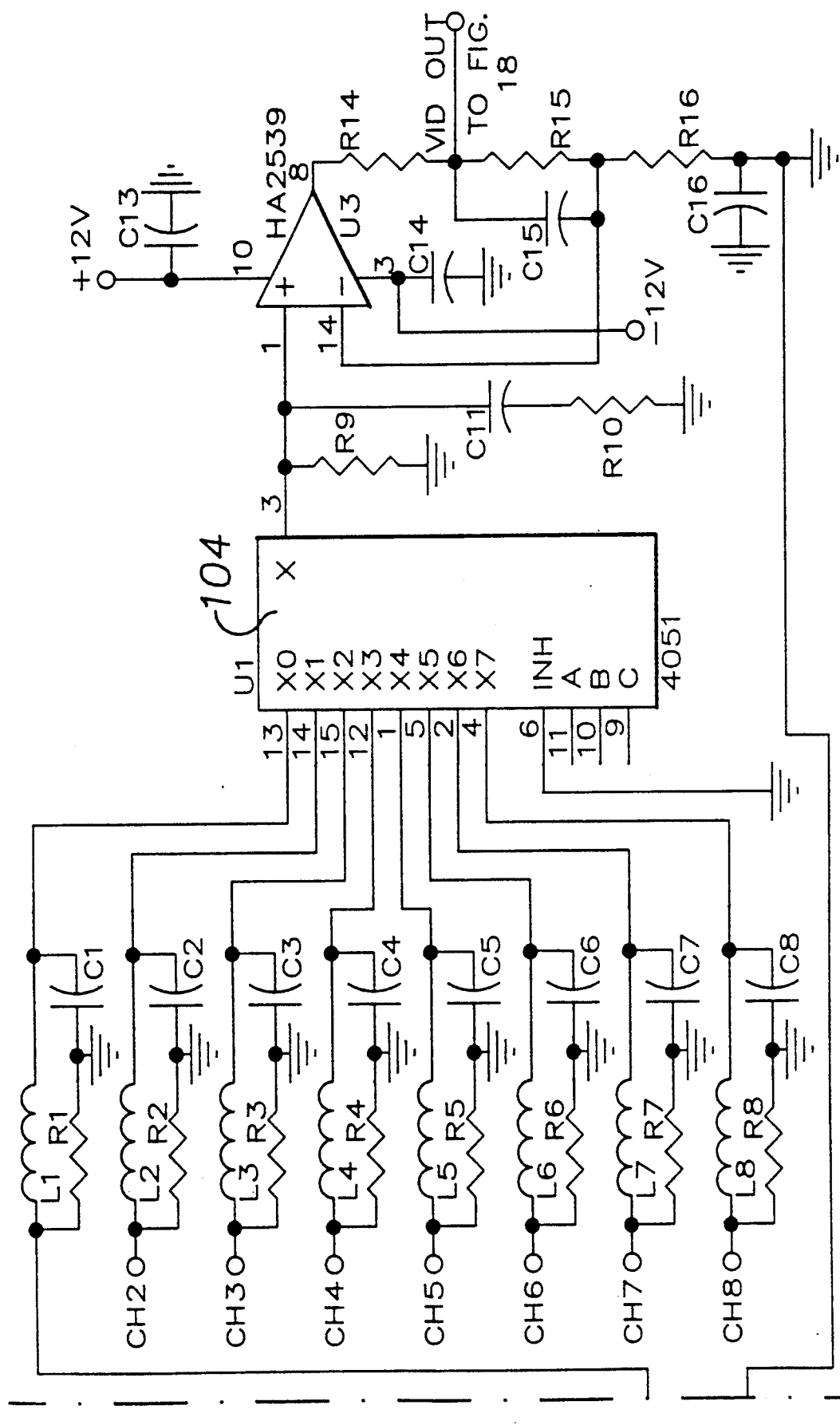

FIGS. 17a to 17c, assembled as shown in FIG. 17d, and collectively referred to herein as FIG. 17, show in more detail part of the Signal Conditioning Means 1 of FIG. 12; signal inversion and amplification circuitry and analog multiplexing.

Figure 18A:
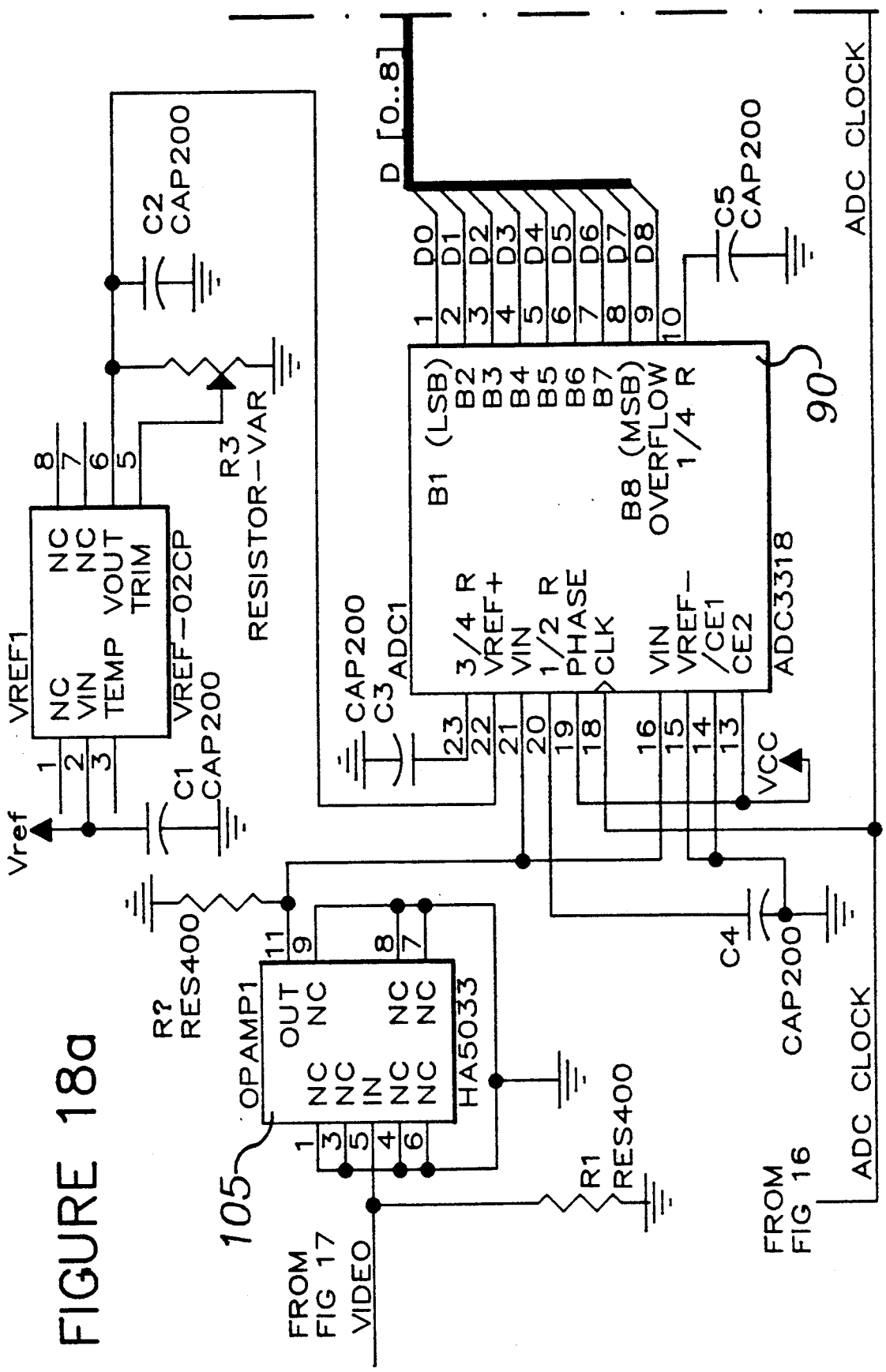
Figure 18B:
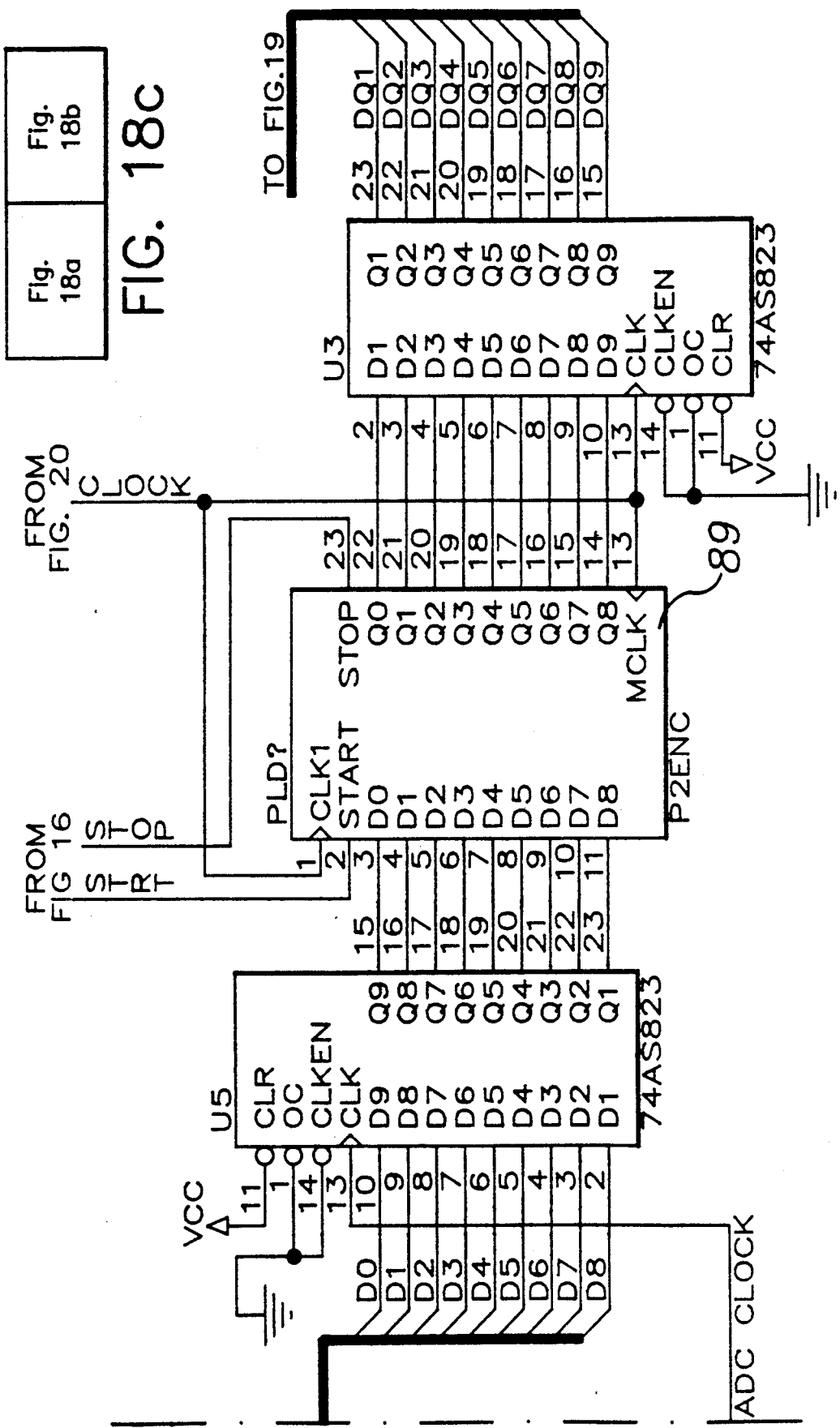

FIGS. 18a to 18b, assembled as shown in FIG. 18c, and collectively referred to herein as FIG. 18, show in more detail part of the Signal Conditioning Means 1 of FIG. 12; analog to digital conversion and data encoding circuitry.

Figure 19A:
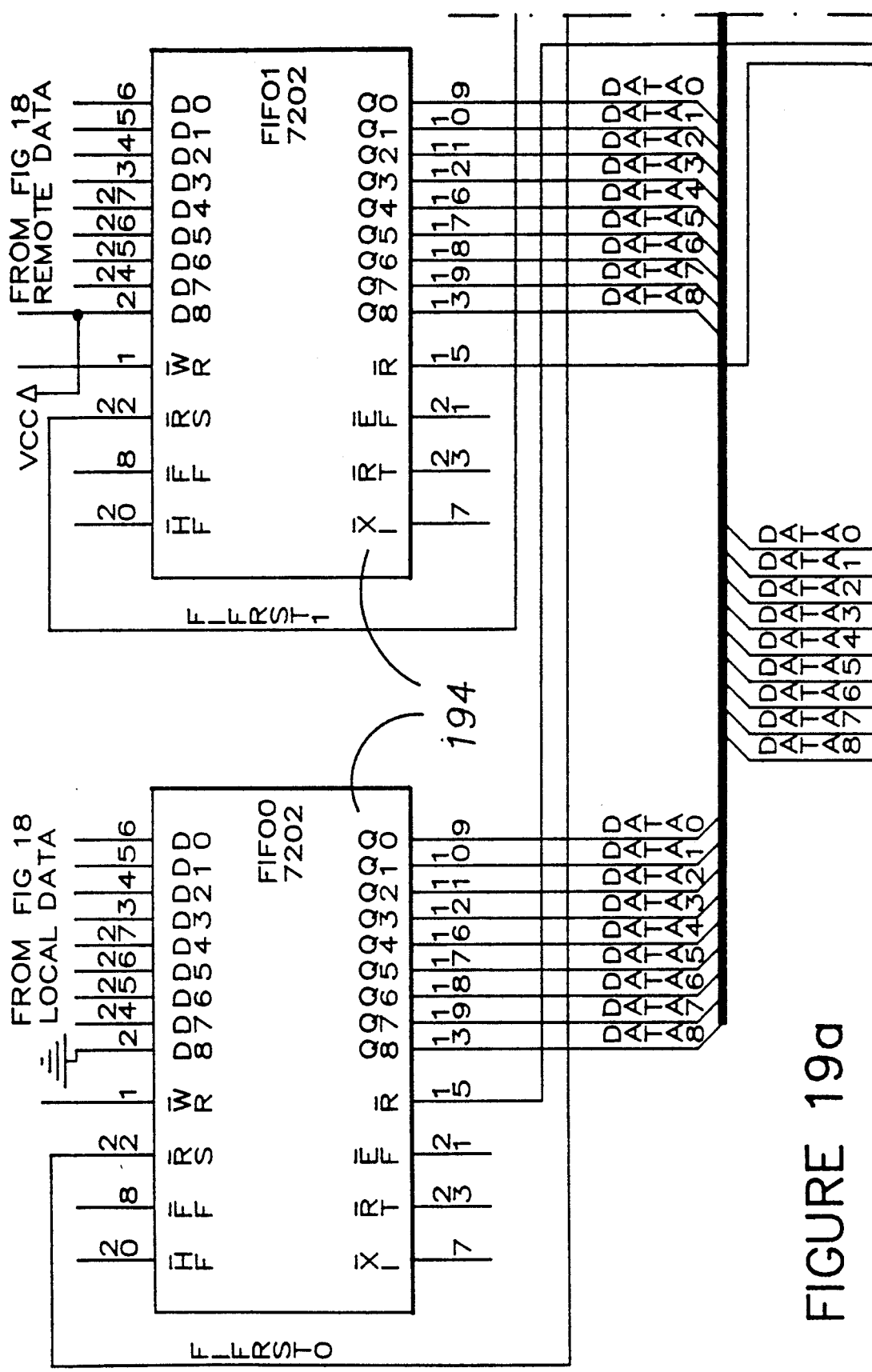
Figure 19B:
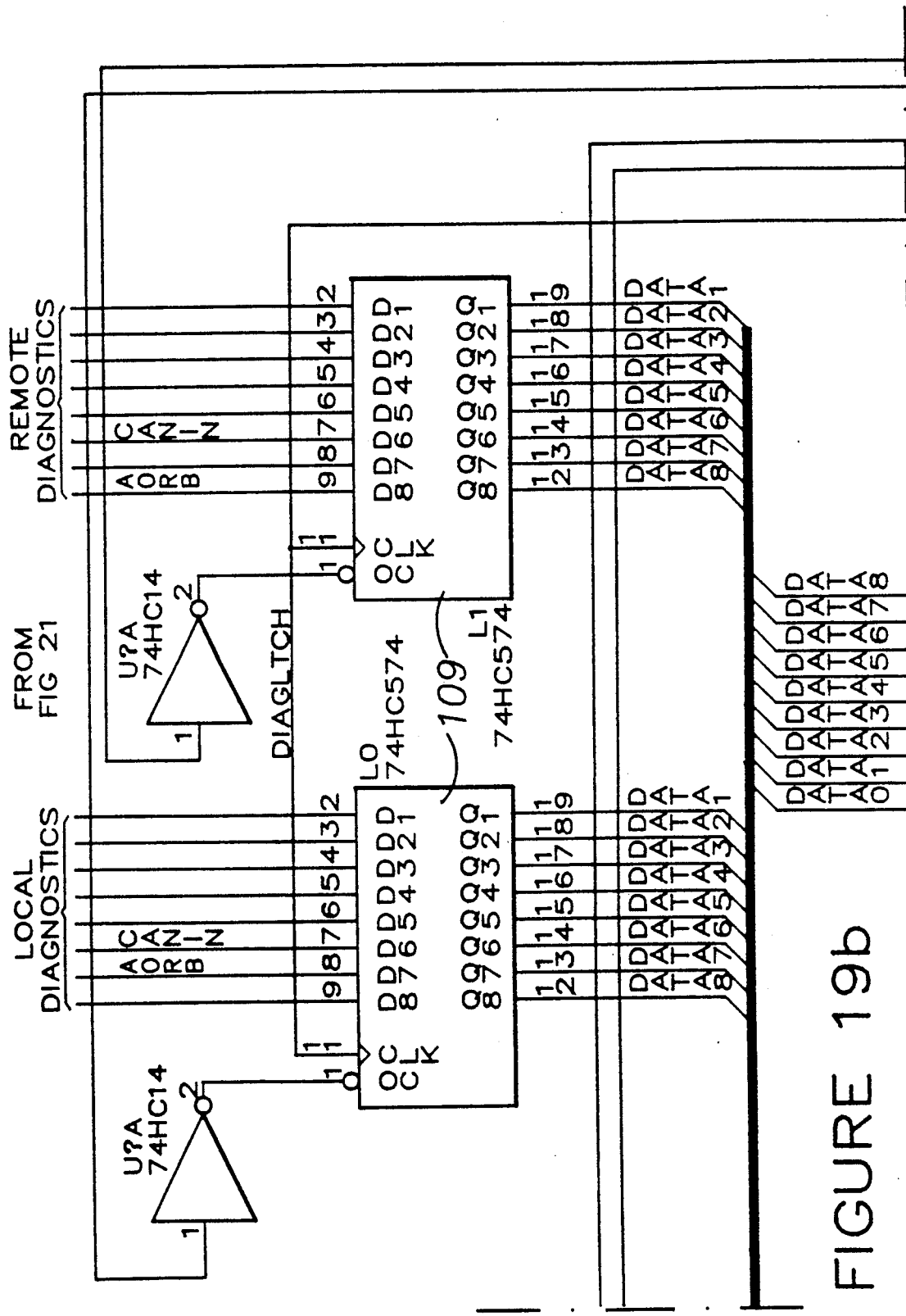
Figure 19C:
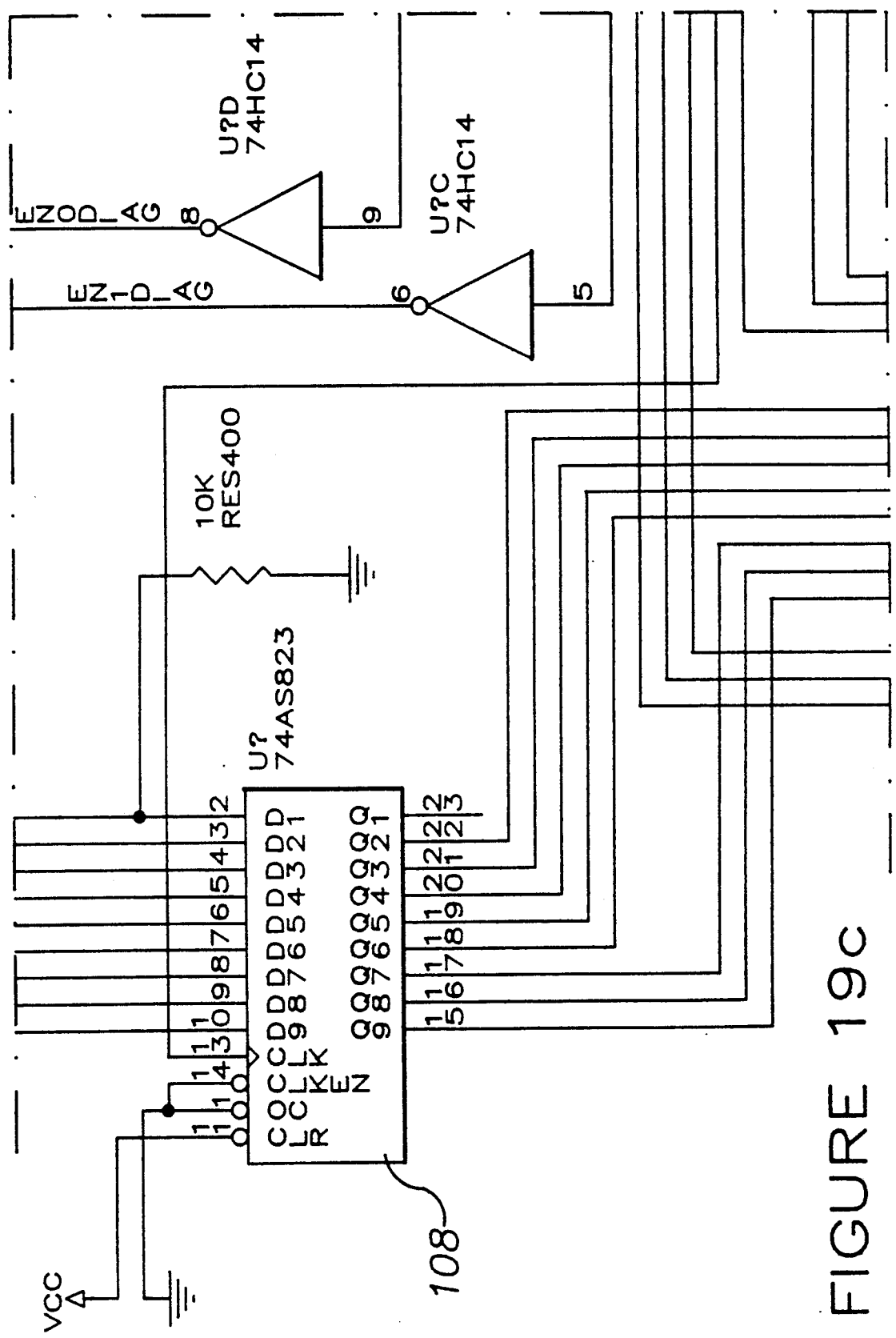
Figure 19D:
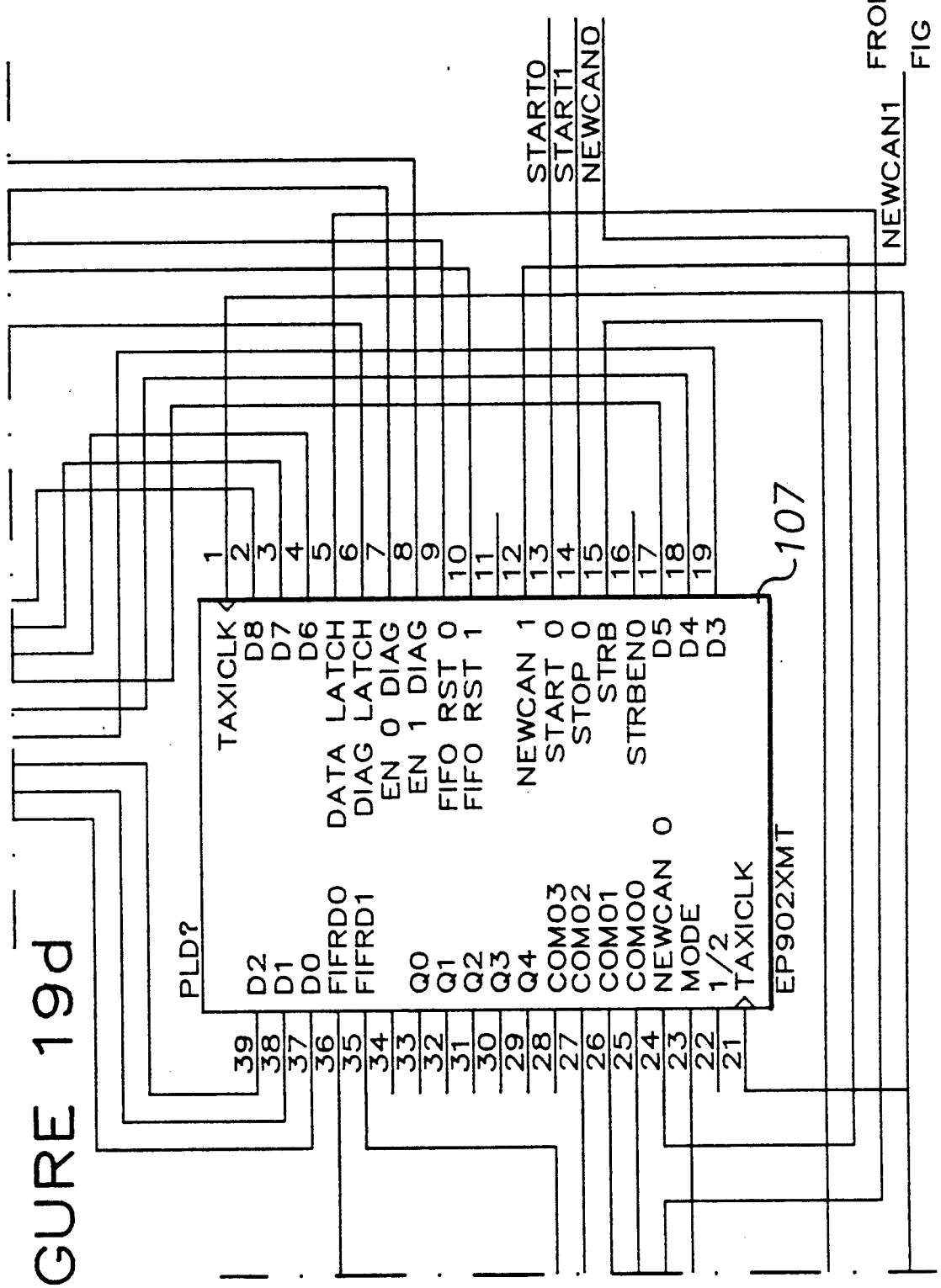
Figure 19E:
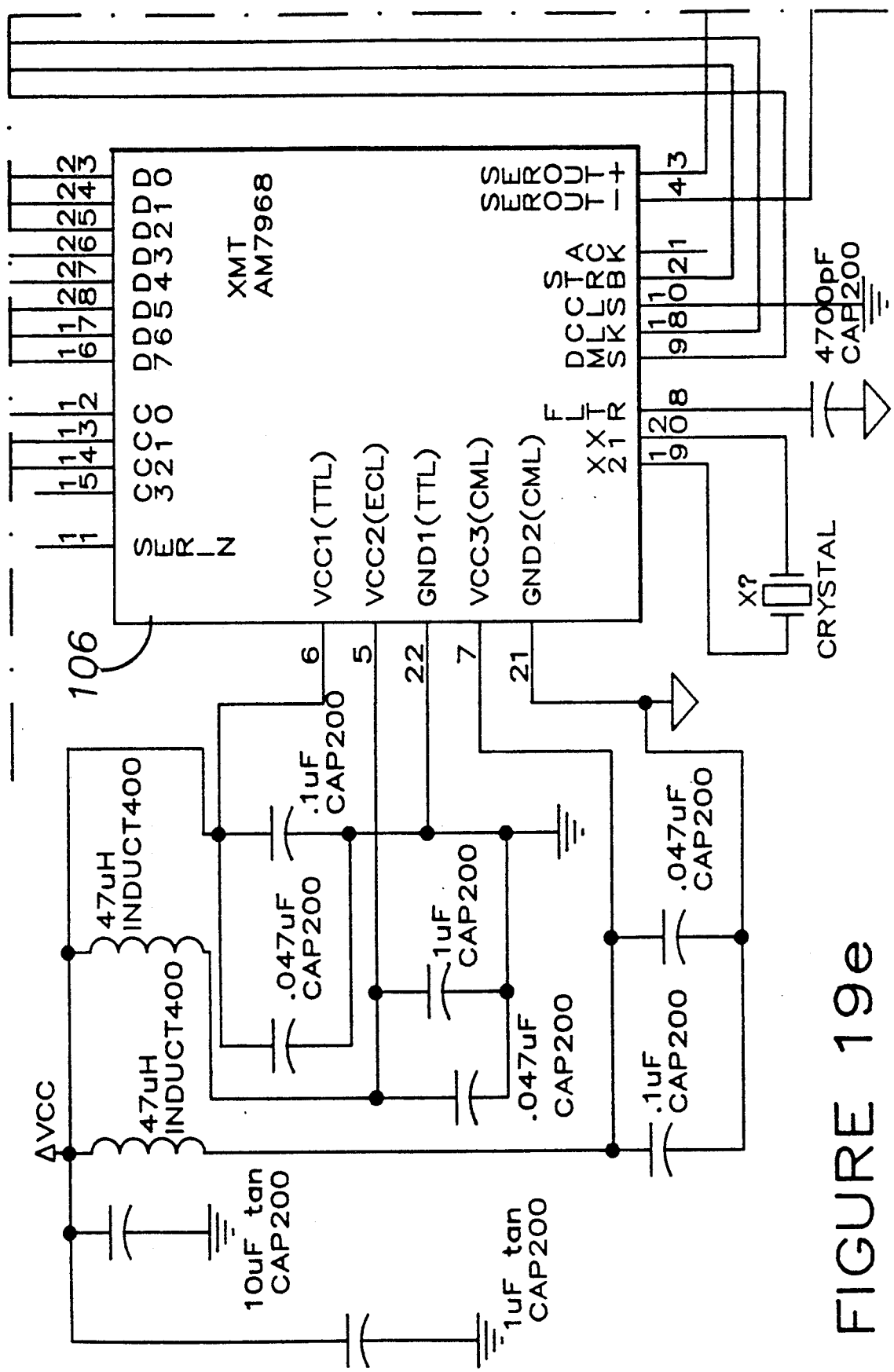
Figure 19F:
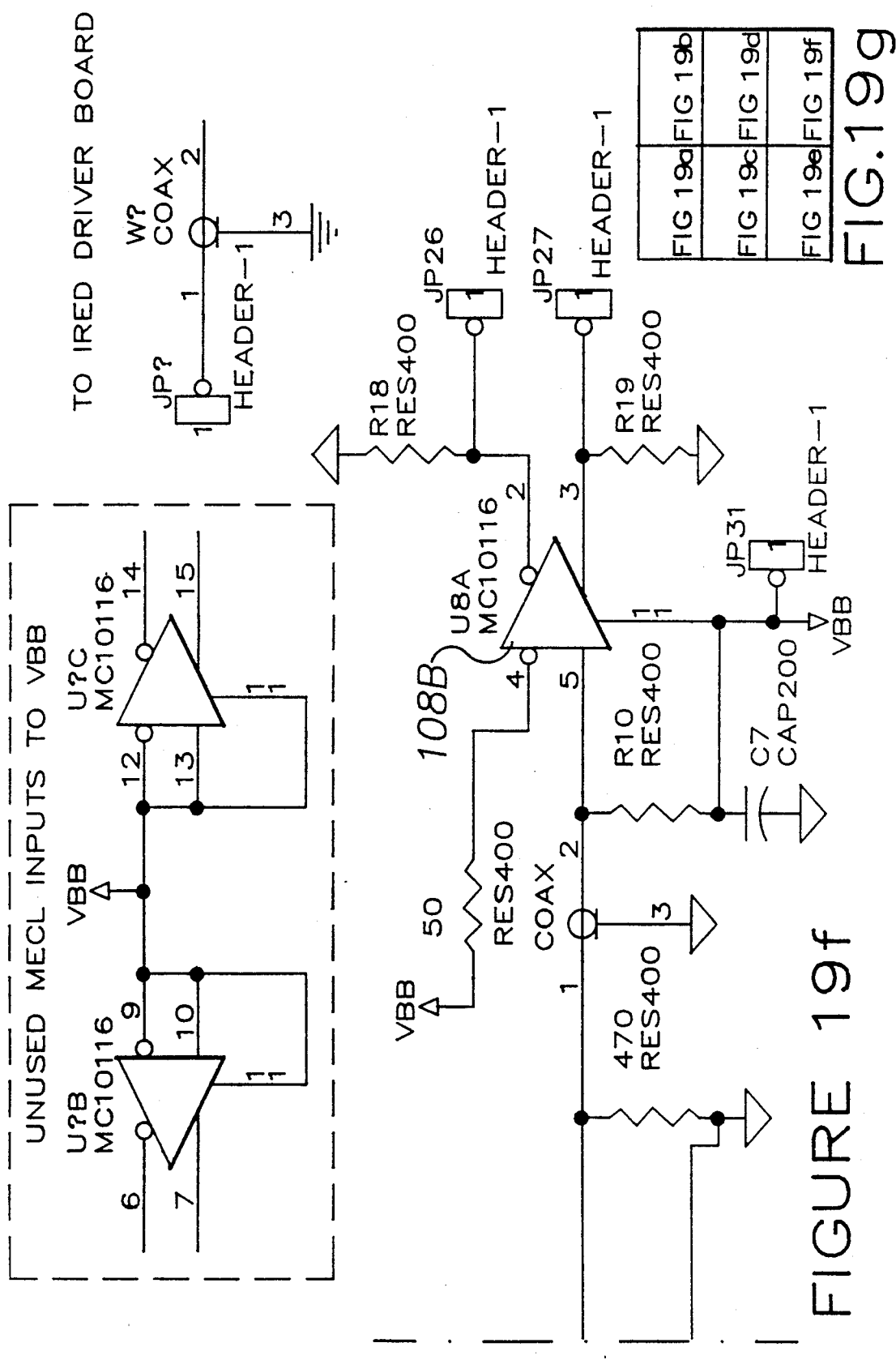
Figure 20A:
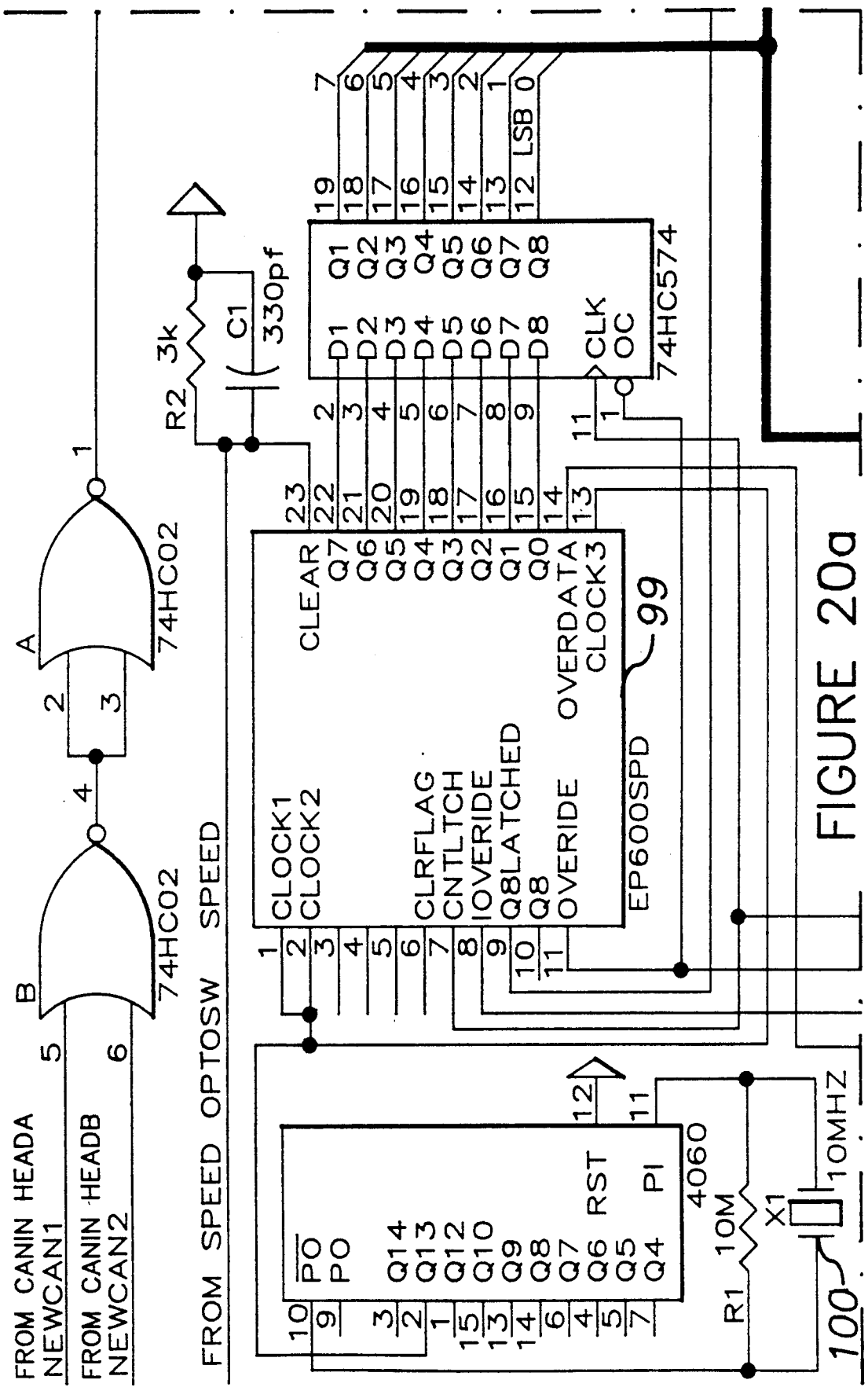
Figure 20B:
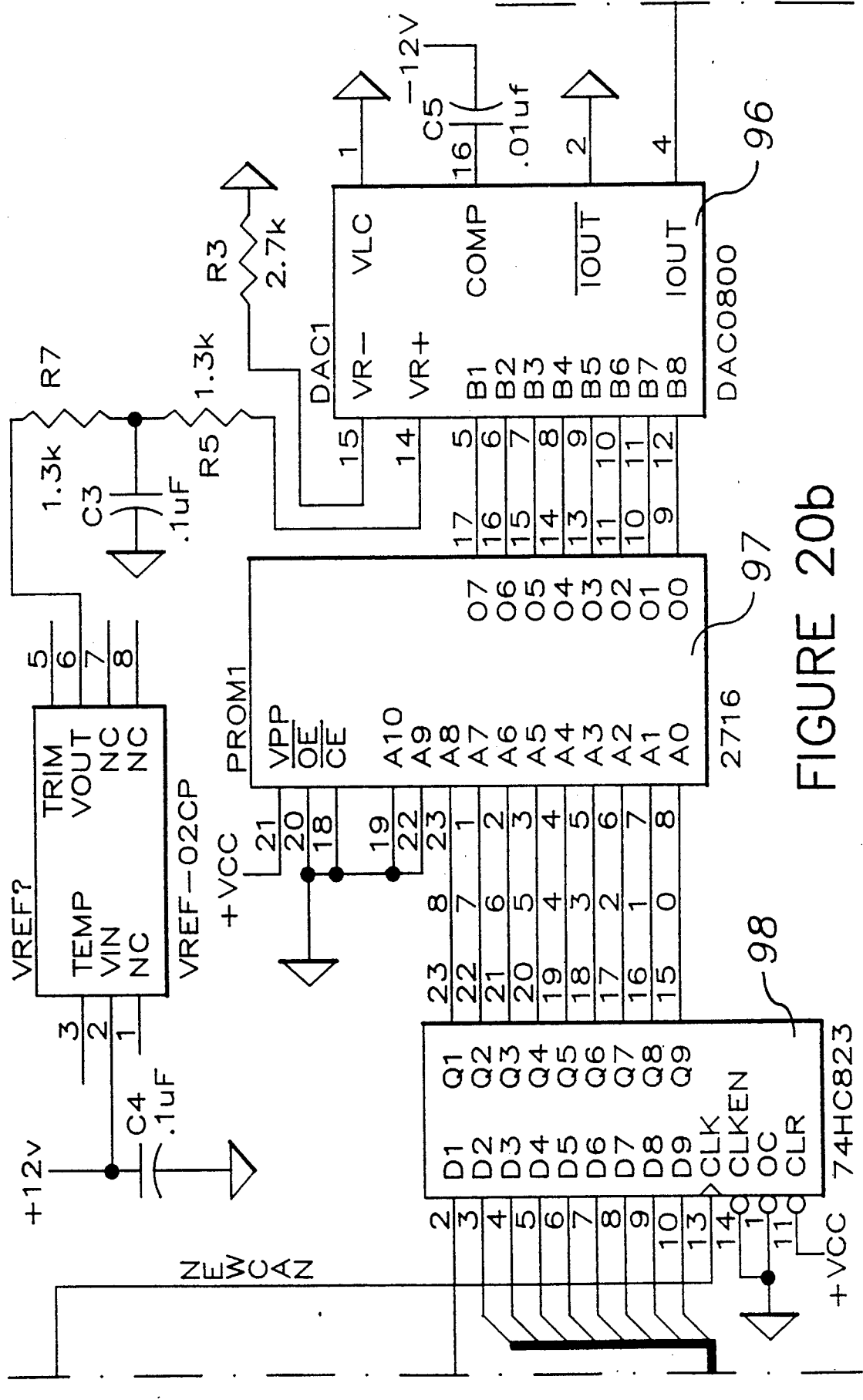
Figure 20C:
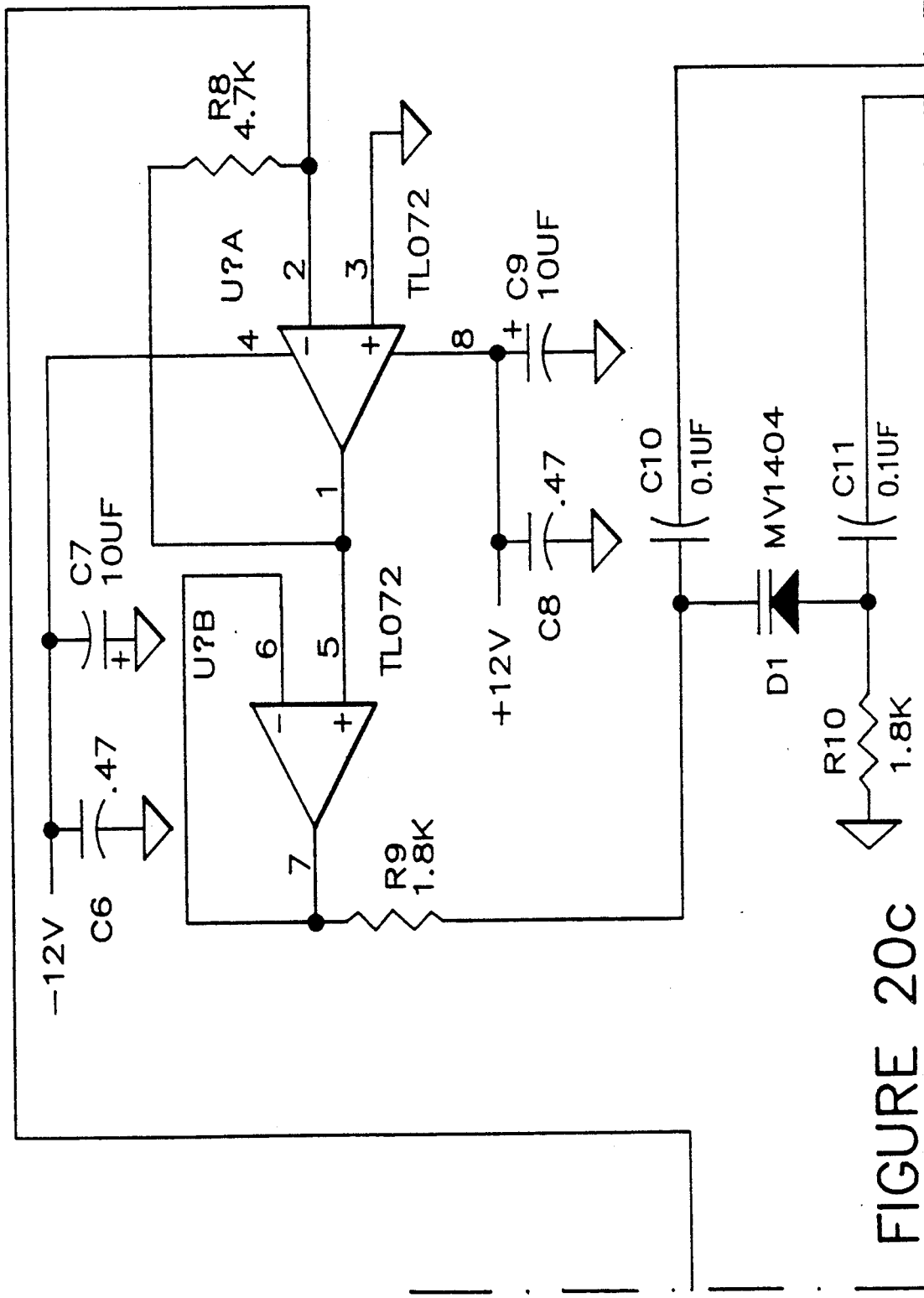
Figure 20D:
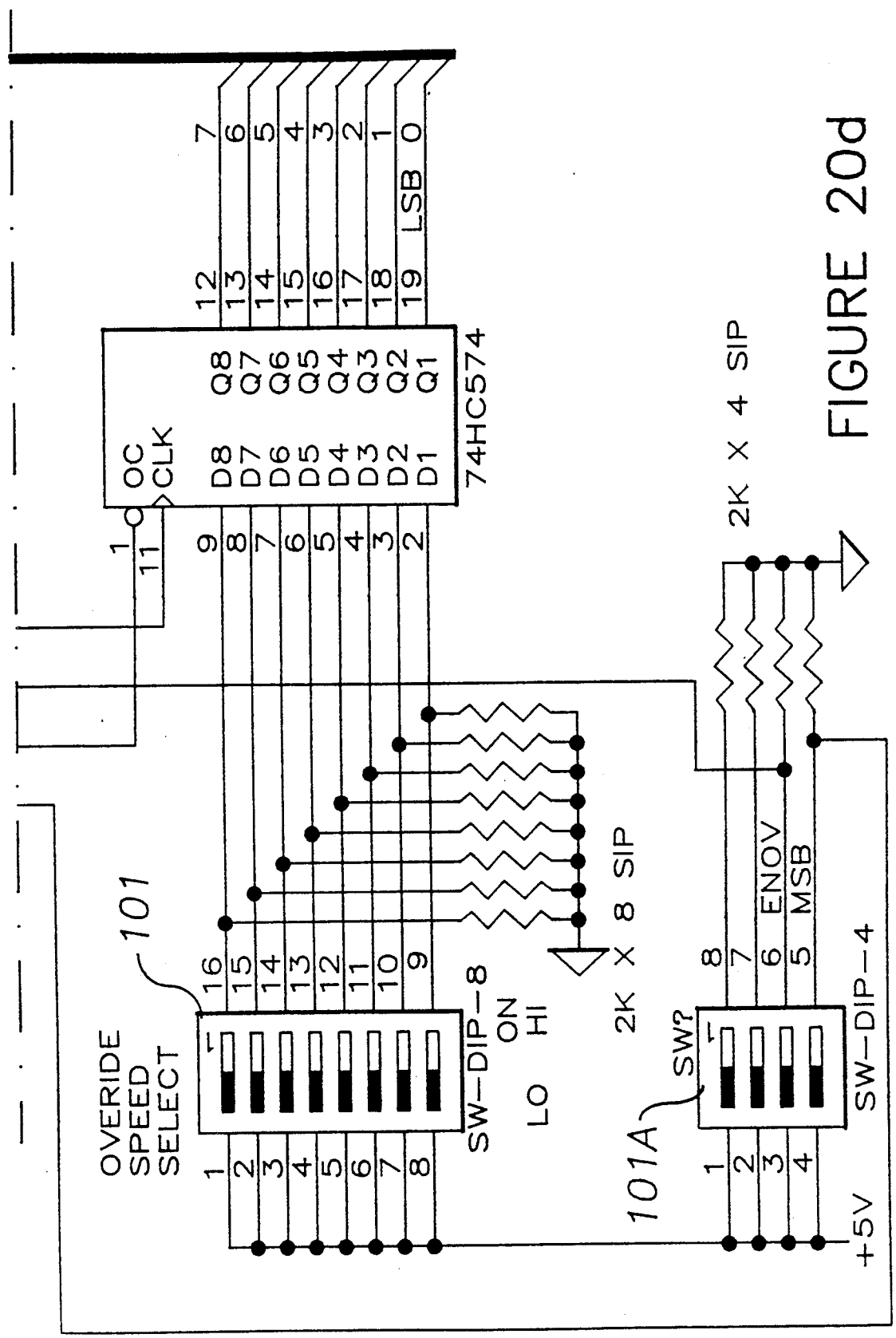
Figure 20E:
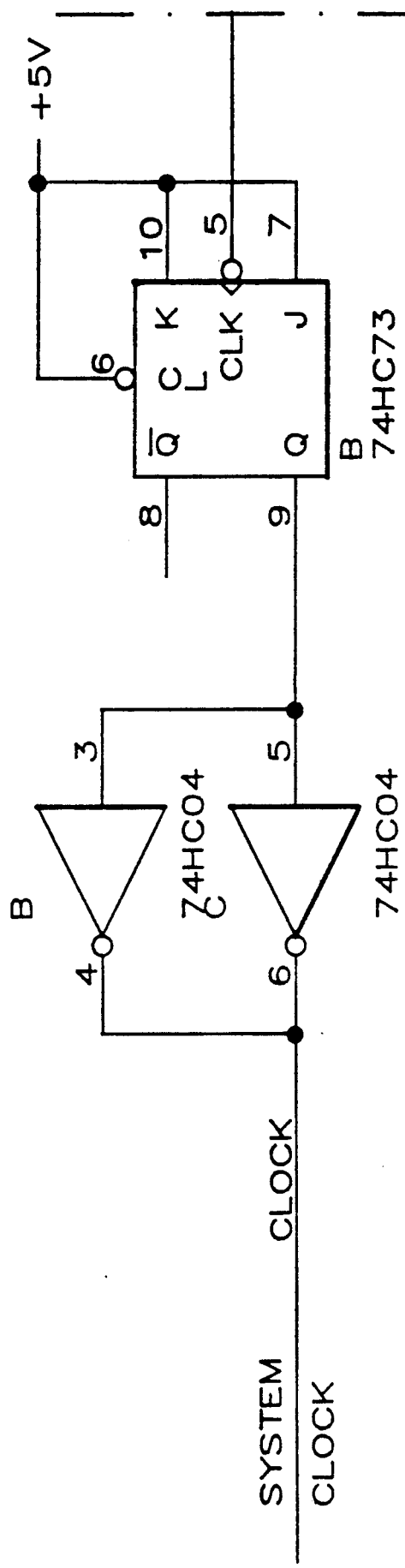
Figure 20F:
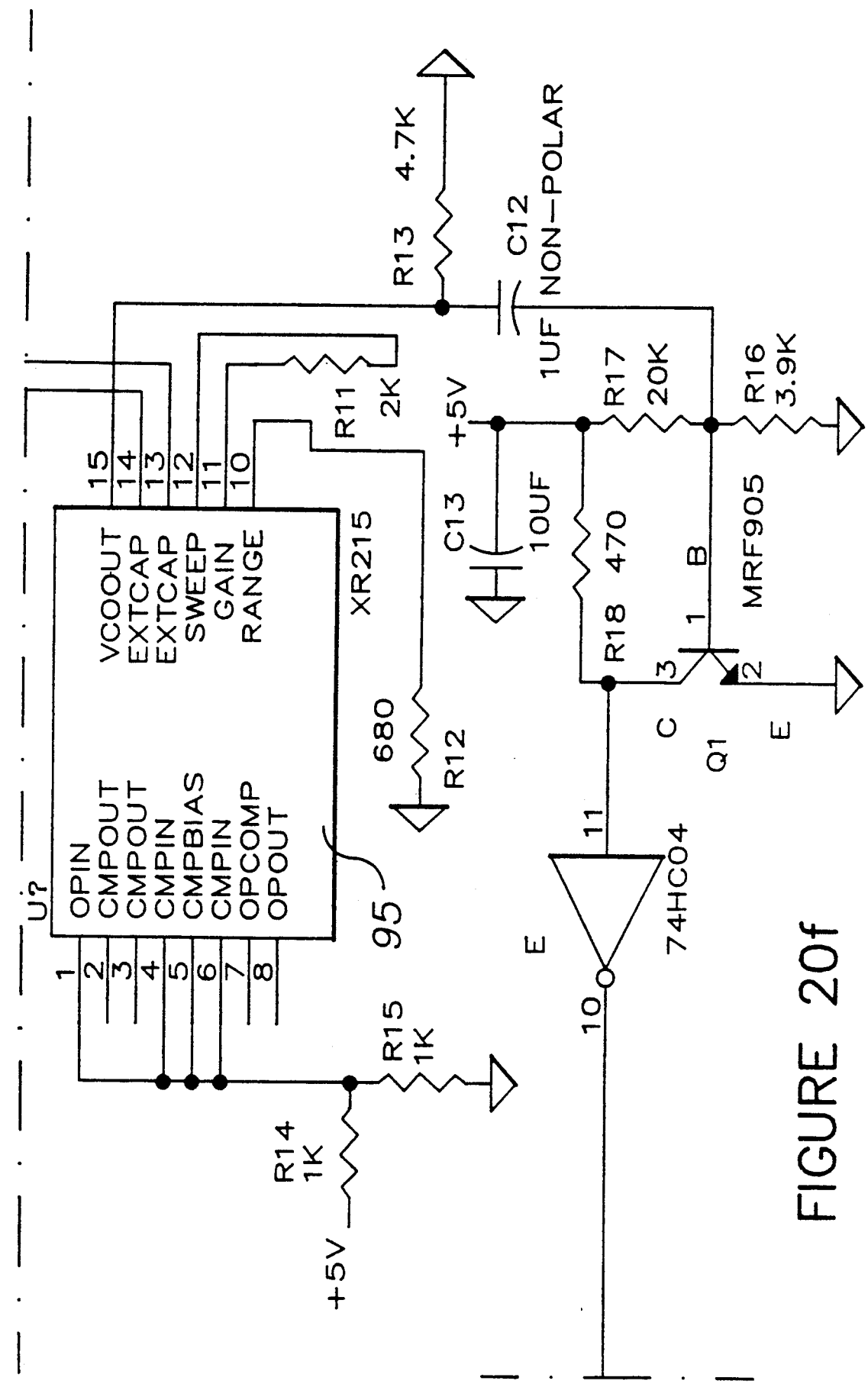
Figure 20G:
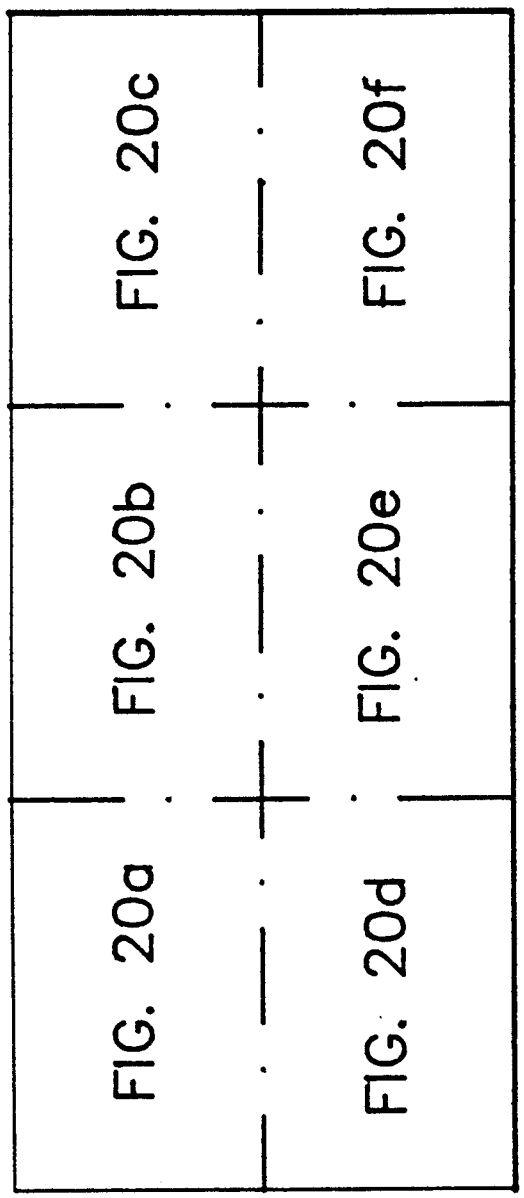

FIGS. 19a to 19f, assembled as shown in FIG. 19g, and collectively referred to herein as FIG. 19, show in more detail part of the Signal Conditioning Means 1 of FIG. 12; circuitry for preparing data for fibre optic transmission.

FIGS. 20a to 20f, assembled as shown in FIG. 19g, and collectively referred to herein as FIG. 20, show in more detail part of the Signal Production Means 1 of FIG. 12; circuitry for generating a system clock related to the machine speed.

Figure 21:
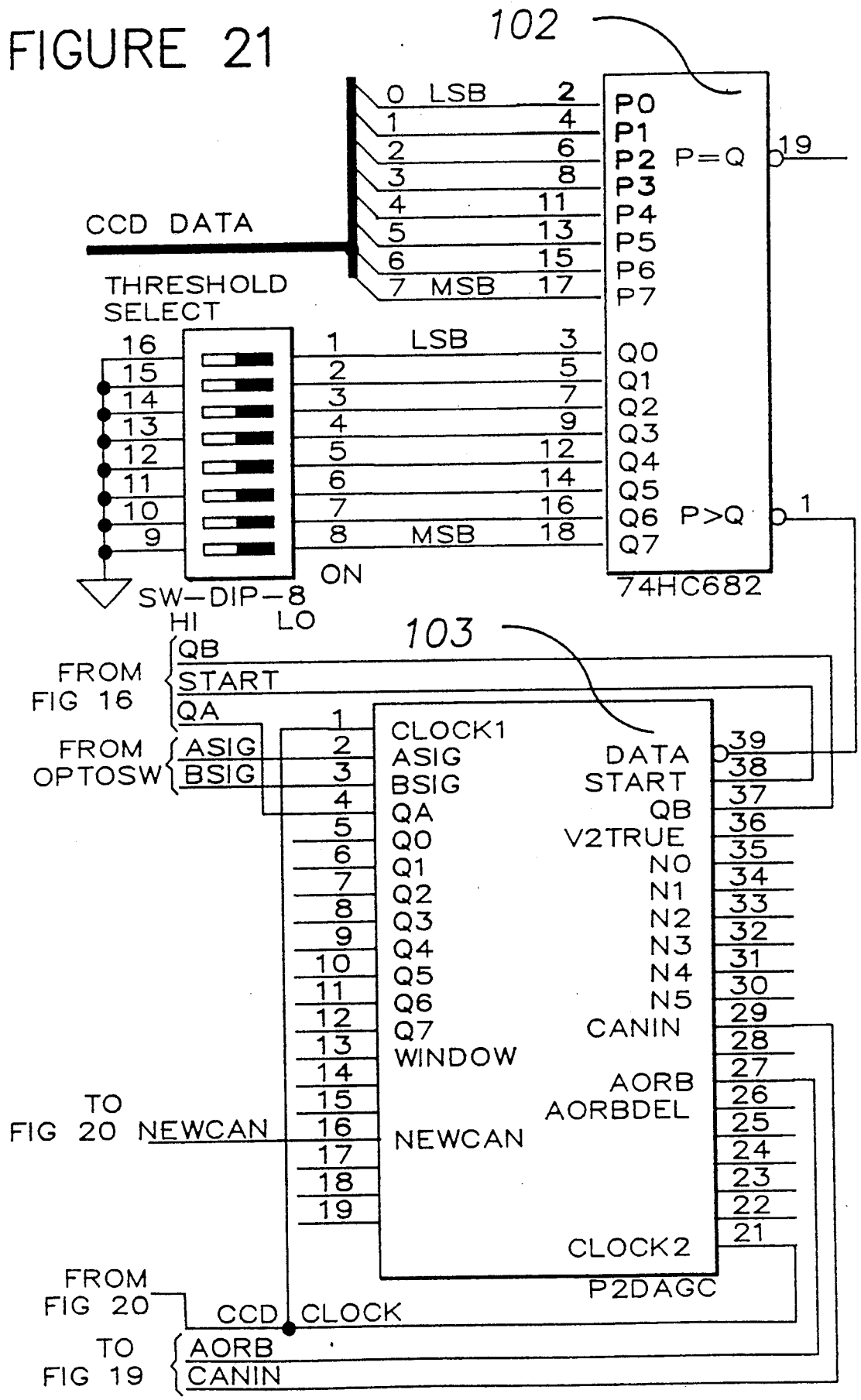

FIG. 21 shows in more detail part of the Signal Conditioning Means 1 of FIG. 12; circuitry to provide various control signals.

Figure 22A:
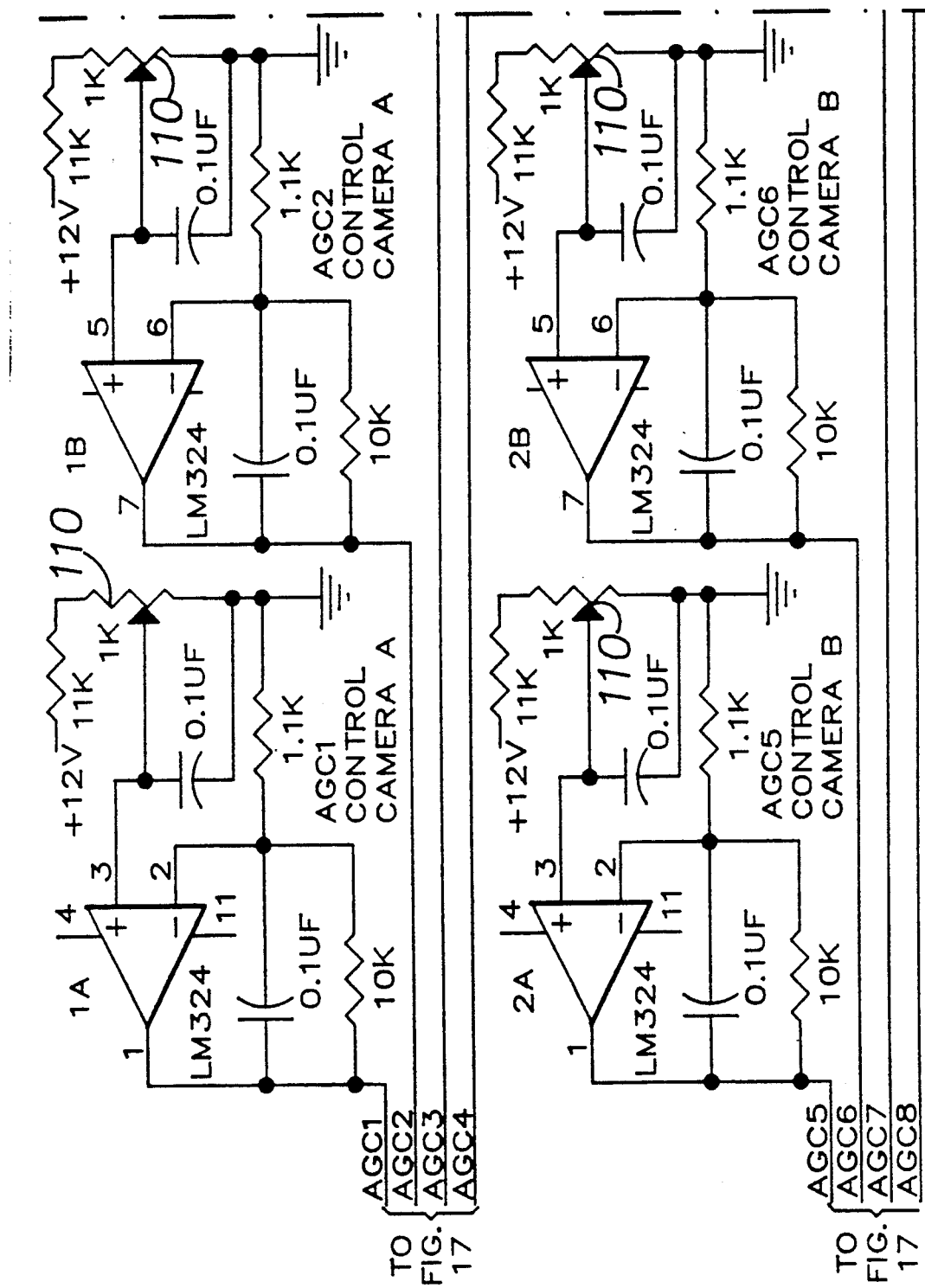

FIGS. 22a to 22b, assembled as shown in FIG. 22c, and collectively referred to herein as FIG. 22, show in more detail part of the Signal Conditioning Means 1 of FIG. 12; circuitry to control the gain in circuits of FIG. 17.

Figure 23A:
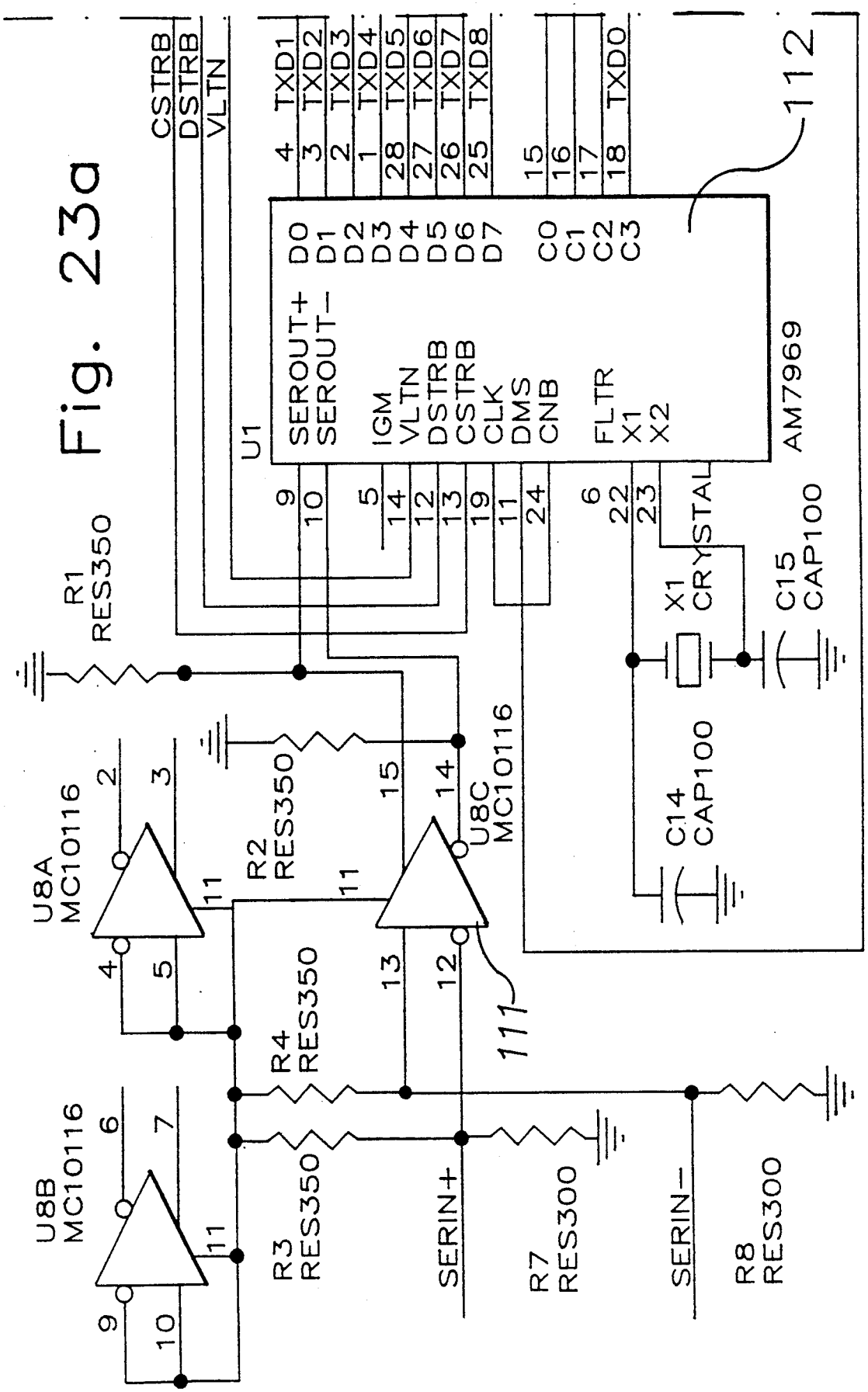
Figure 23B:
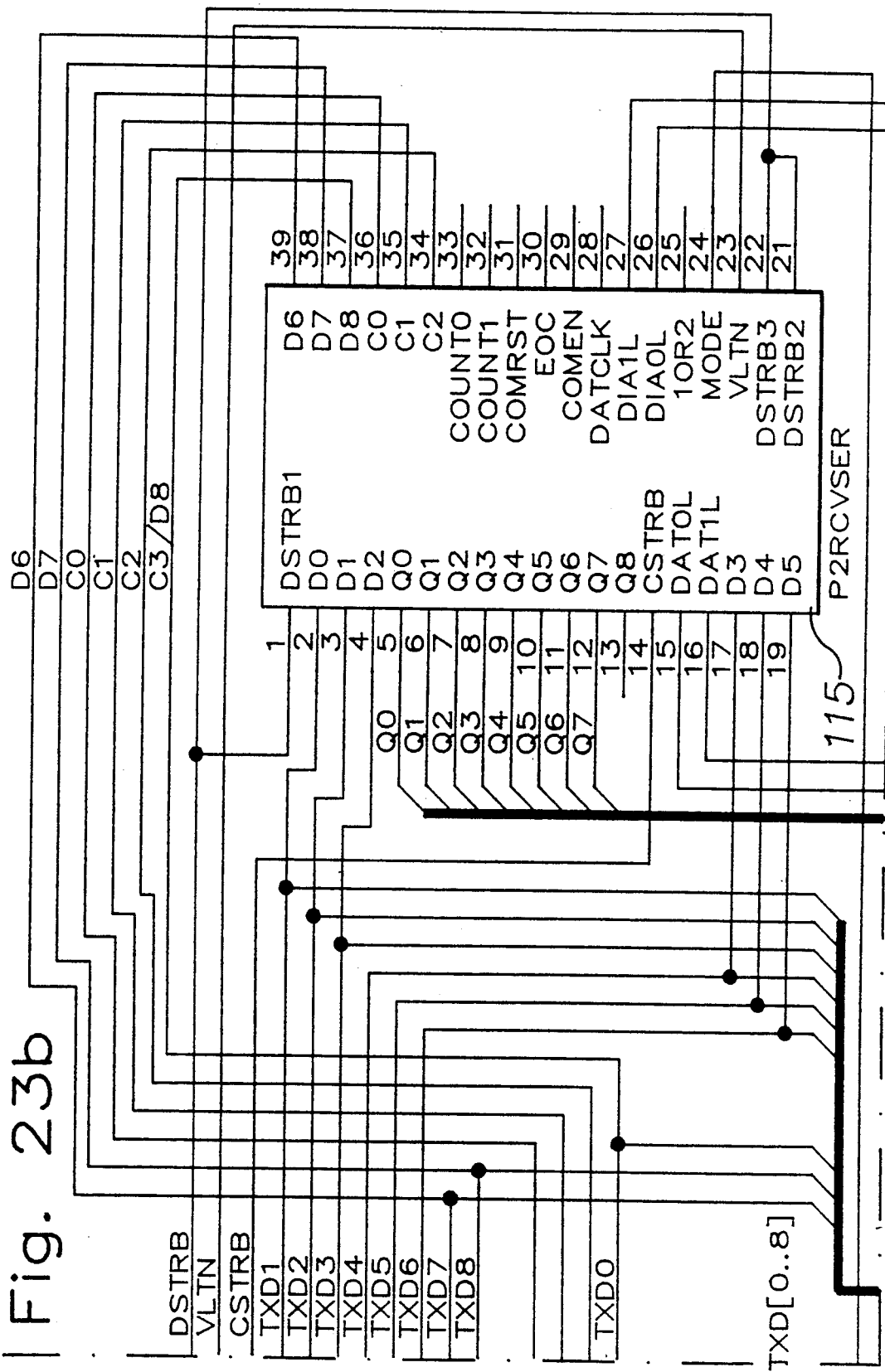
Figure 23C:
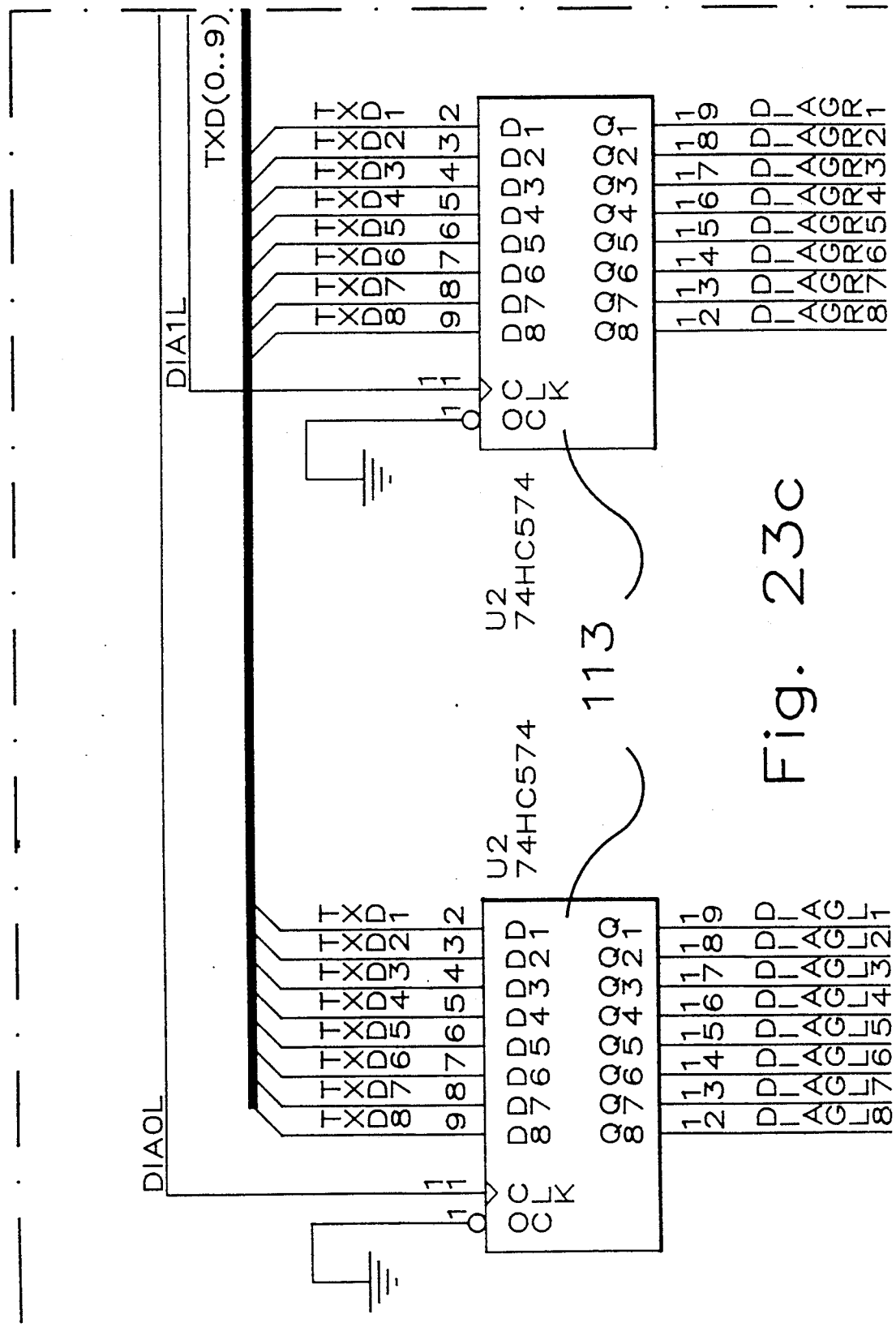

FIGS. 23a to 23d, assembled as shown in FIG. 23e, and collectively referred to herein as FIG. 23, show in more detail part of the Signal Conditioning Means 2 of FIG. 12; circuitry to convert the high speed serial train to parallel format.

Figure 24A:
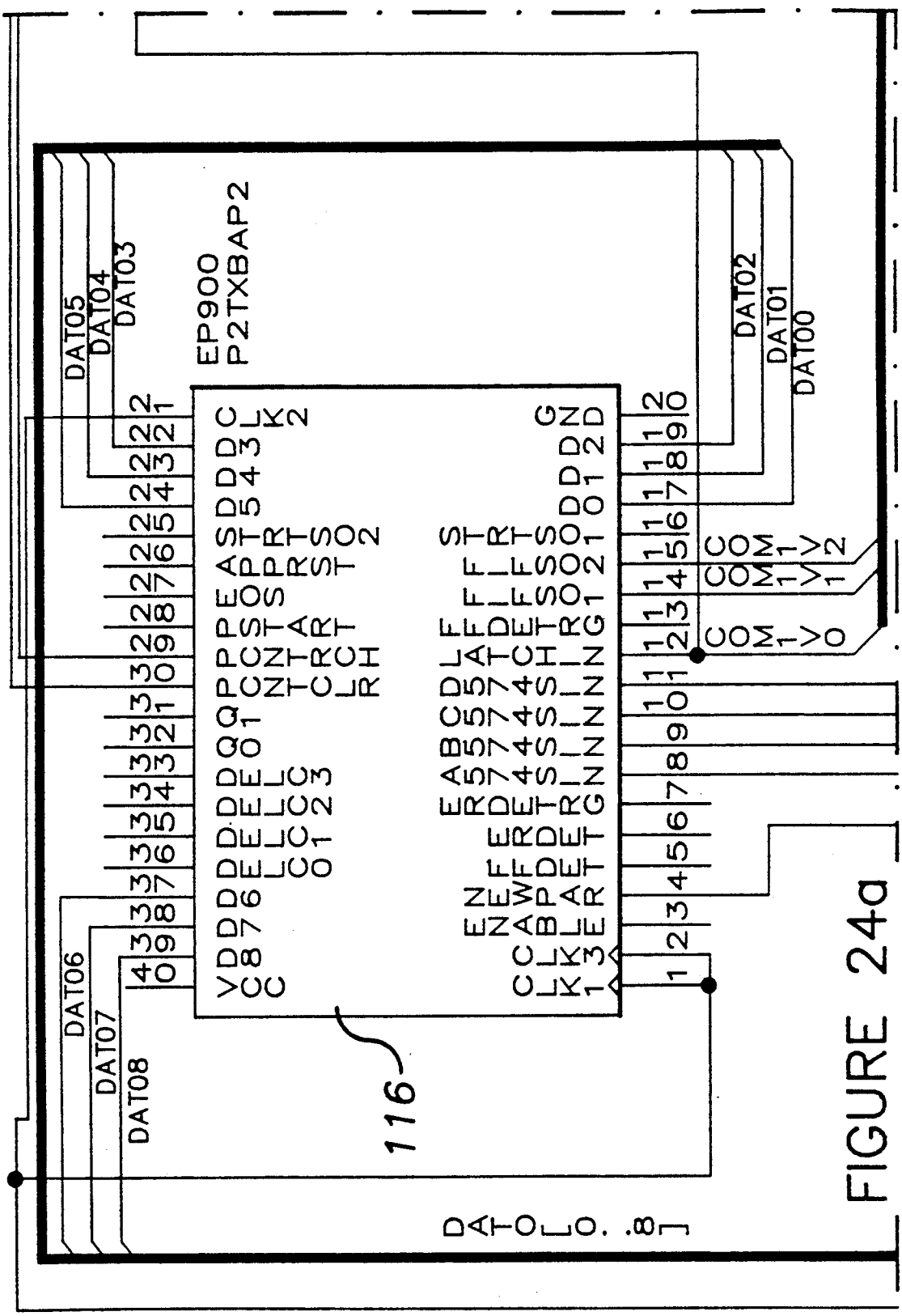
Figure 24B:
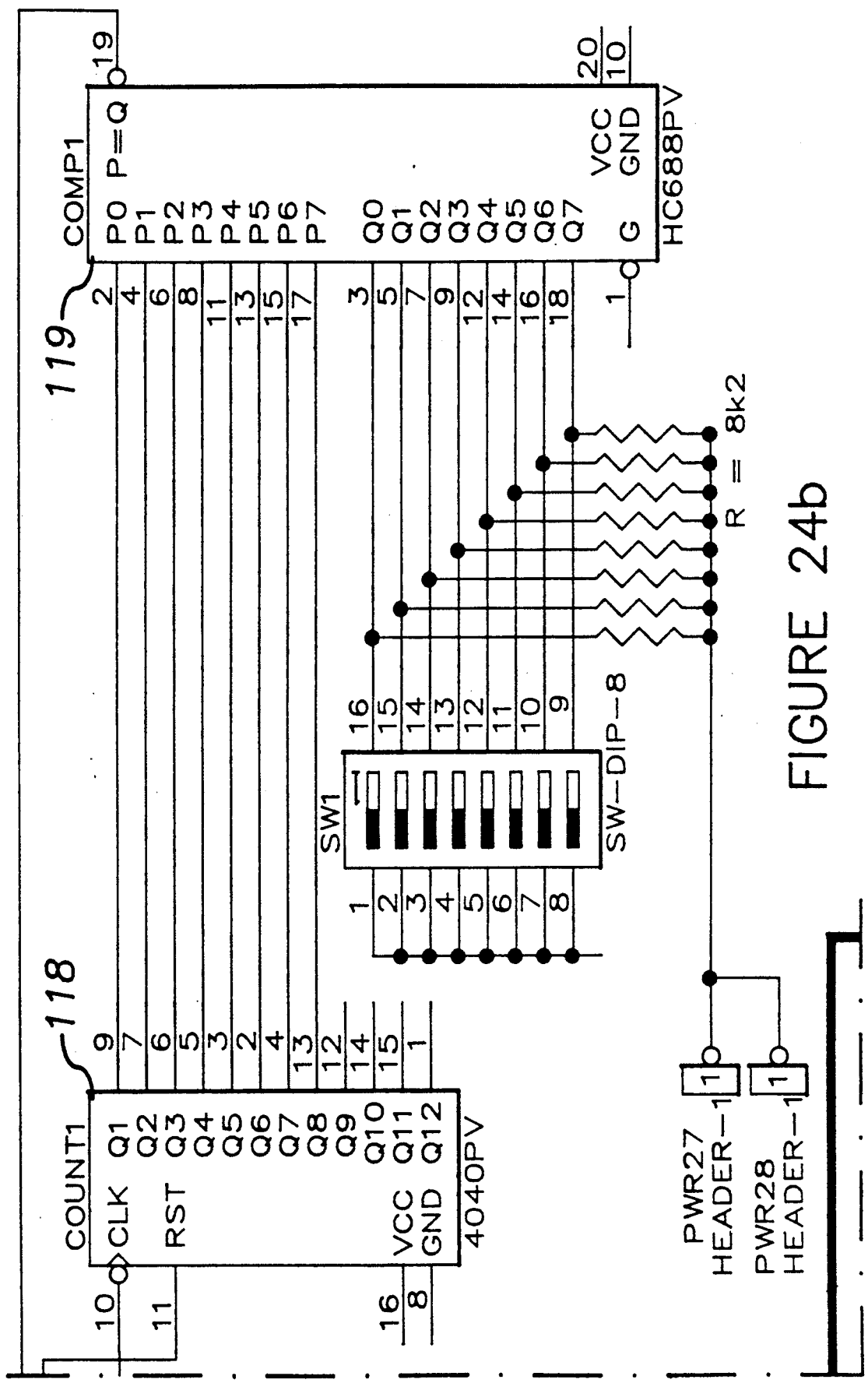
Figure 24C:
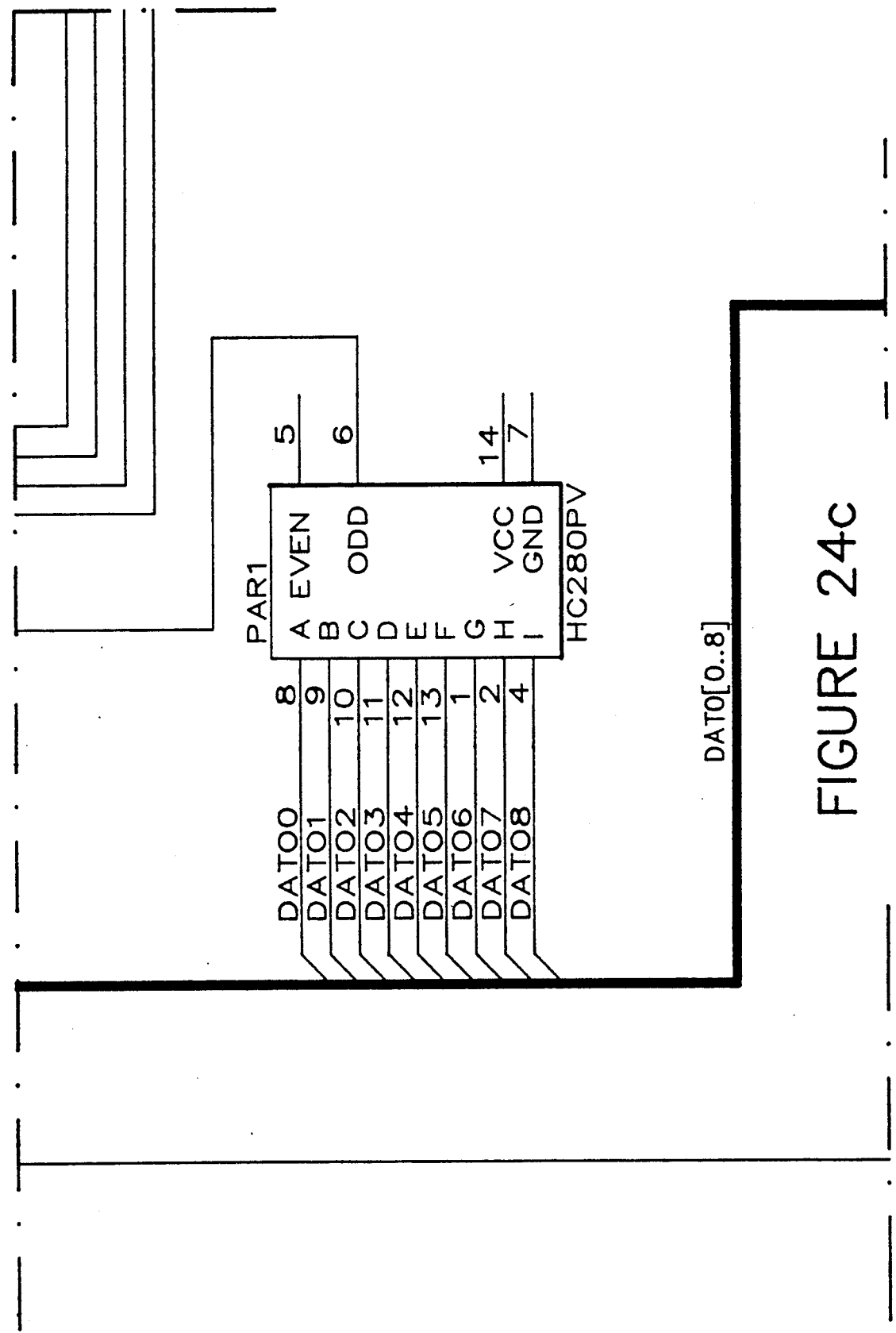
Figure 24D:
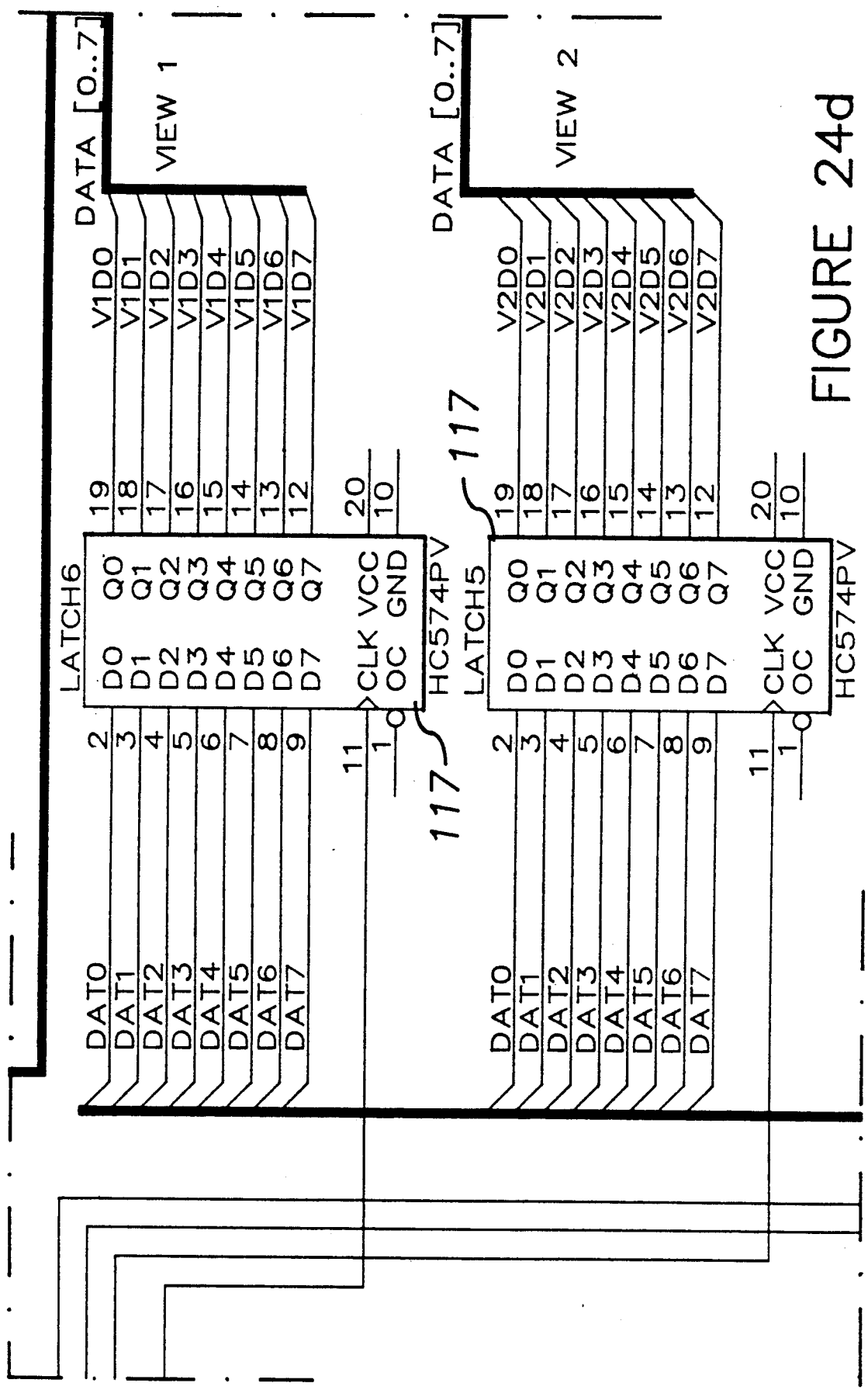
Figure 24E:
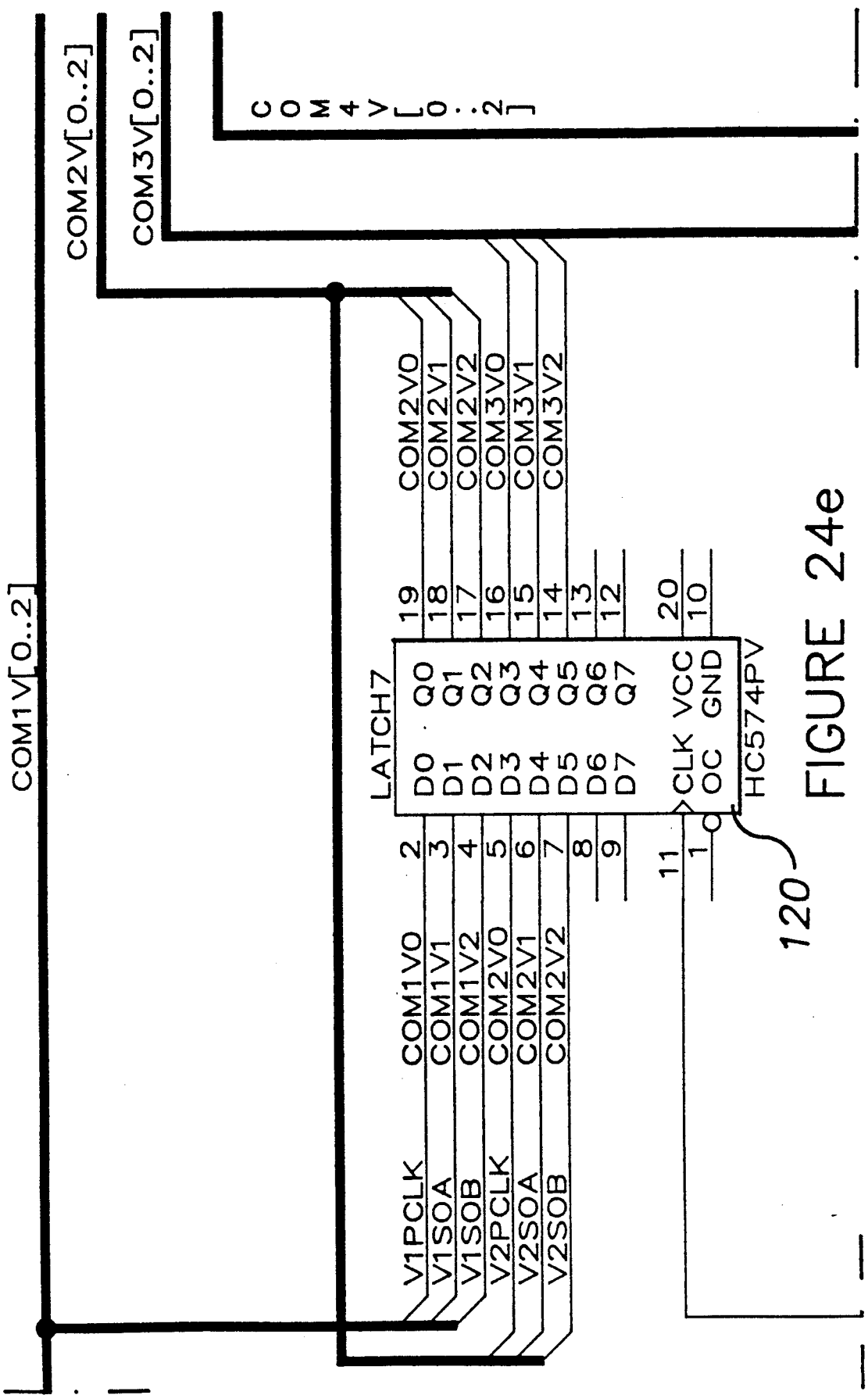
Figure 24F:
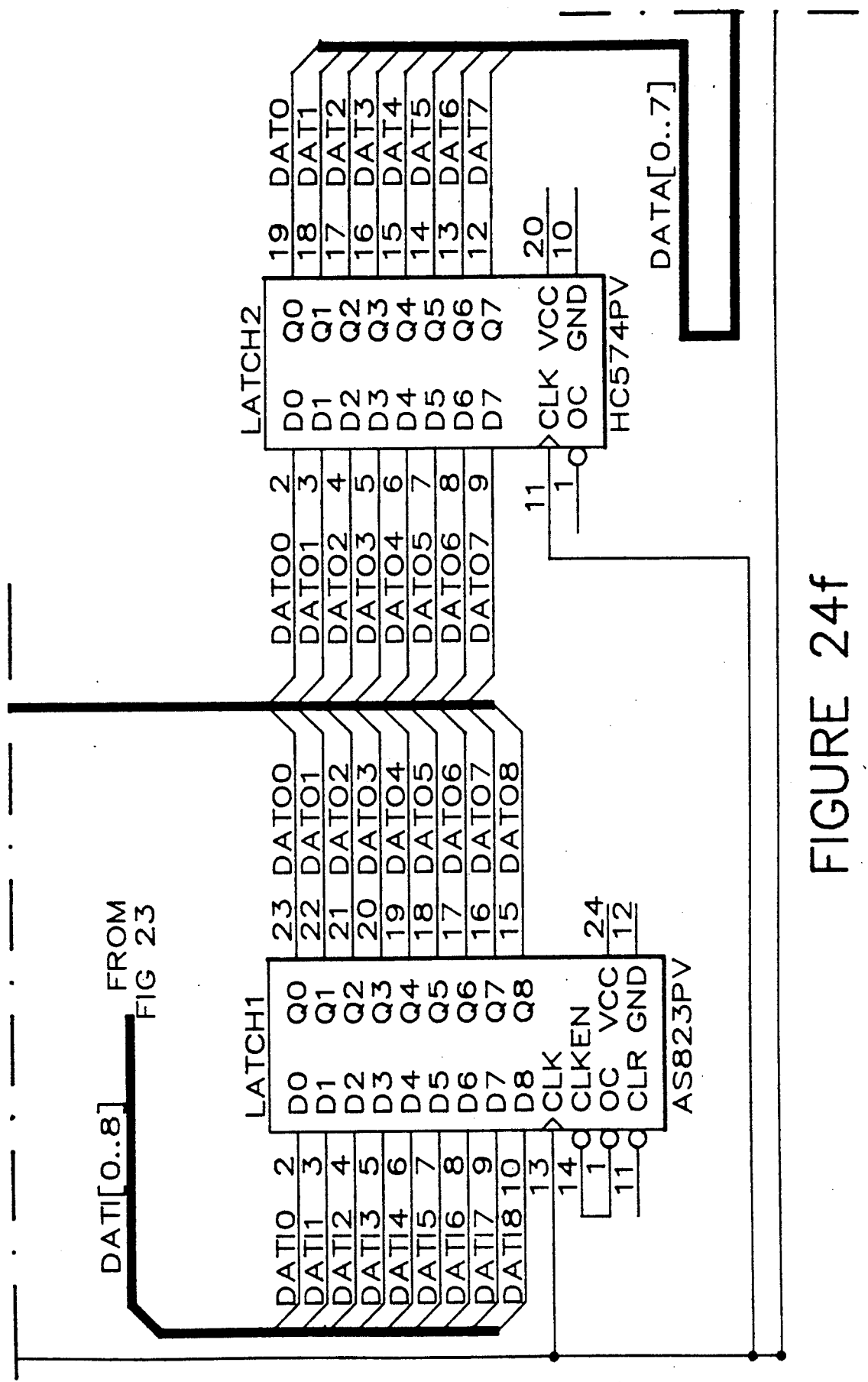
Figure 24G:
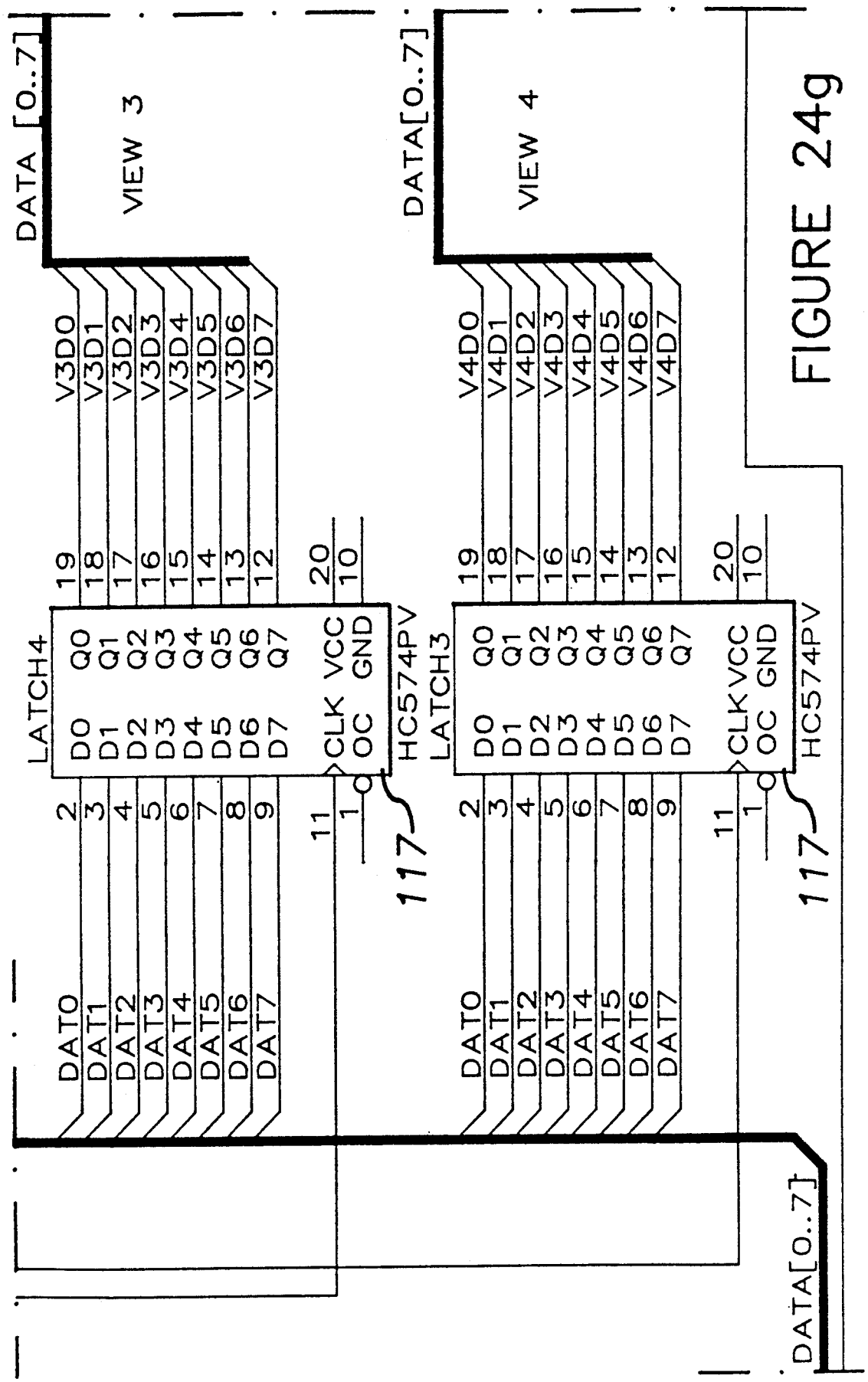
Figure 24H:
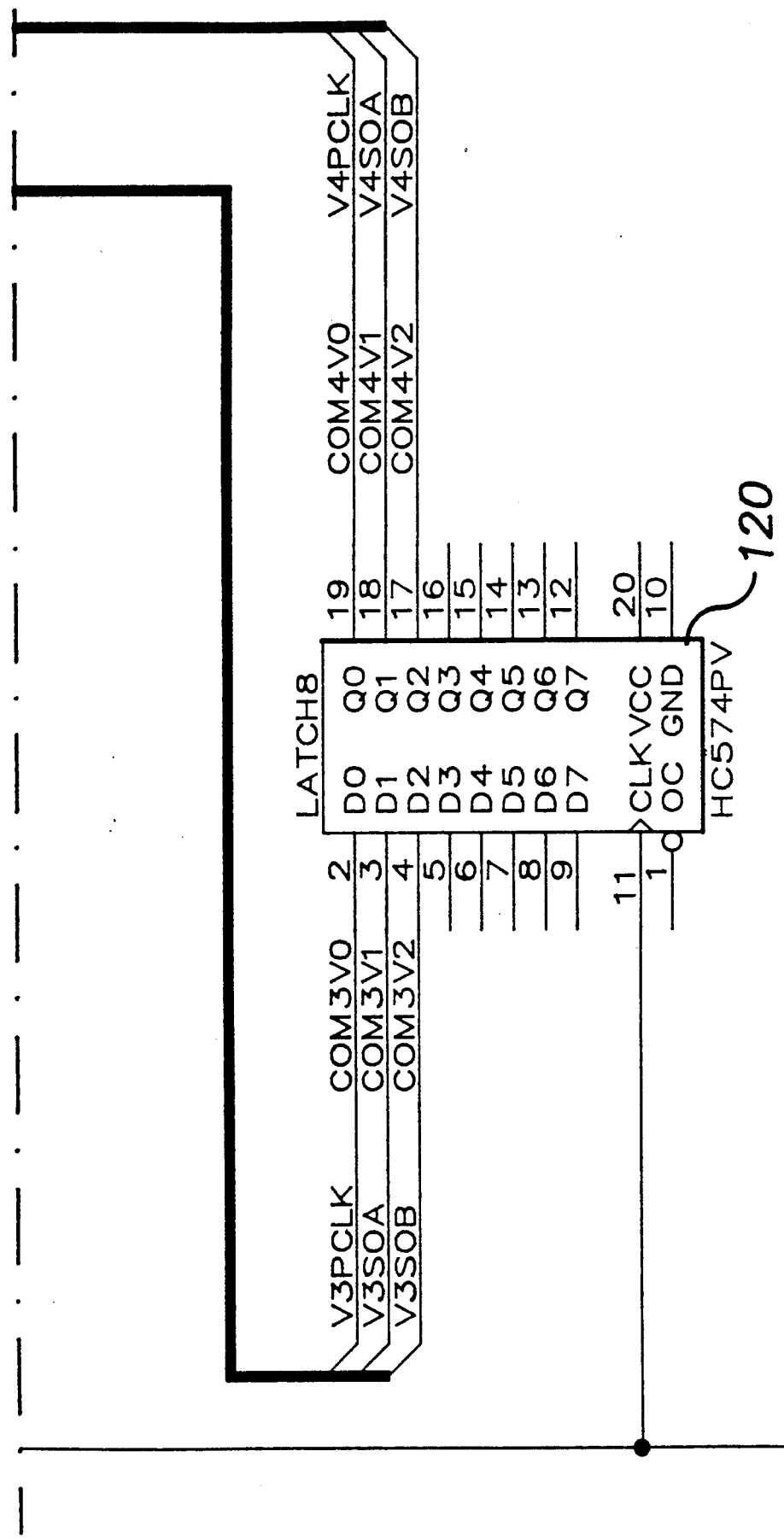
Figure 24I:
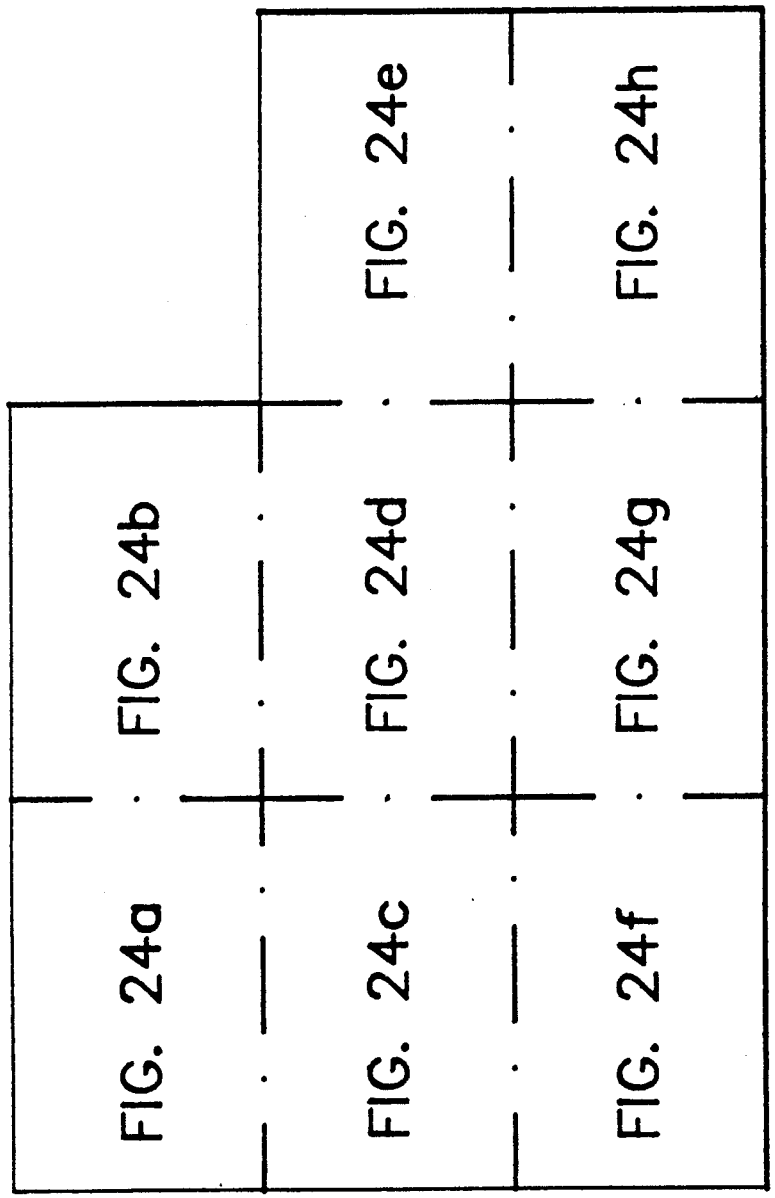

FIGS. 24a to 24h, assembled as shown in FIG. 24i, and collectively referred to herein as FIG. 24, show in more detail part of the Signal Conditioning Means 2 of FIG. 12; demultiplexing of the data.

Figure 25B:
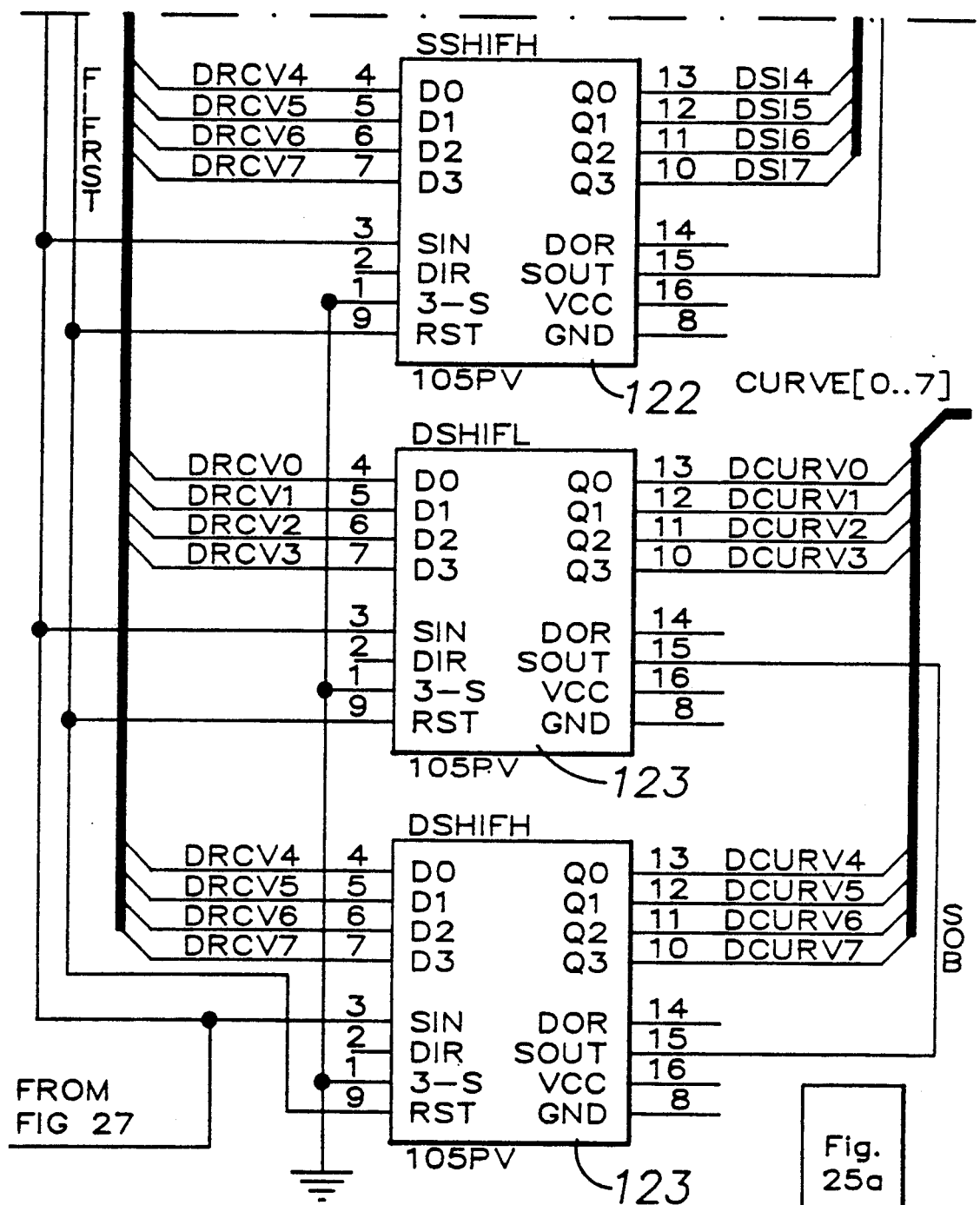

FIGS. 25a to 25b, assembled as shown in FIG. 25c, and collectively referred to herein as FIG. 25, show in more detail part of the Signal Conditioning Means 2 of FIG. 12; circuitry to provide a direct and a delayed signal to the Analog Feature Extraction Means of FIG. 26.

Figure 26A:
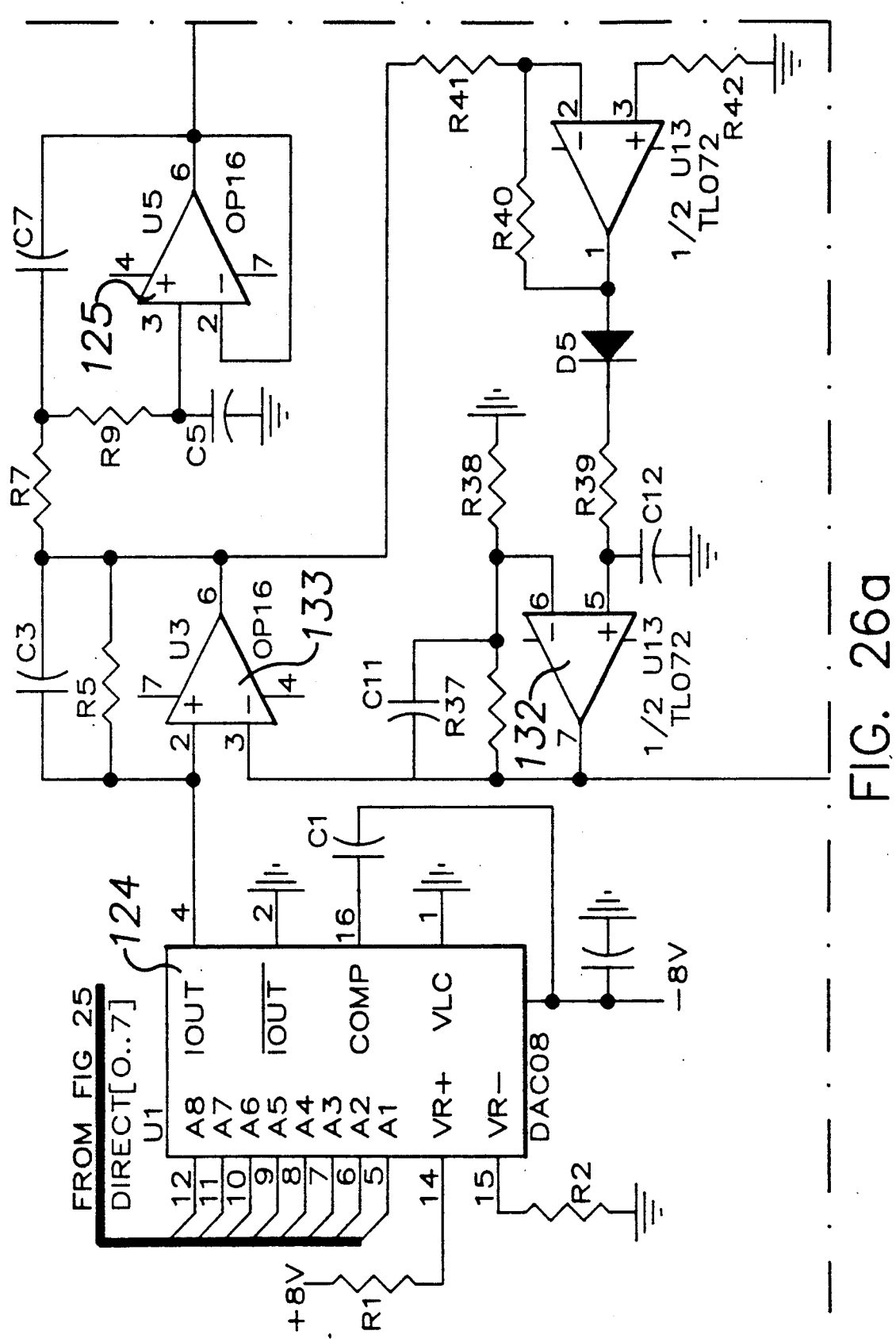
Figure 26B:
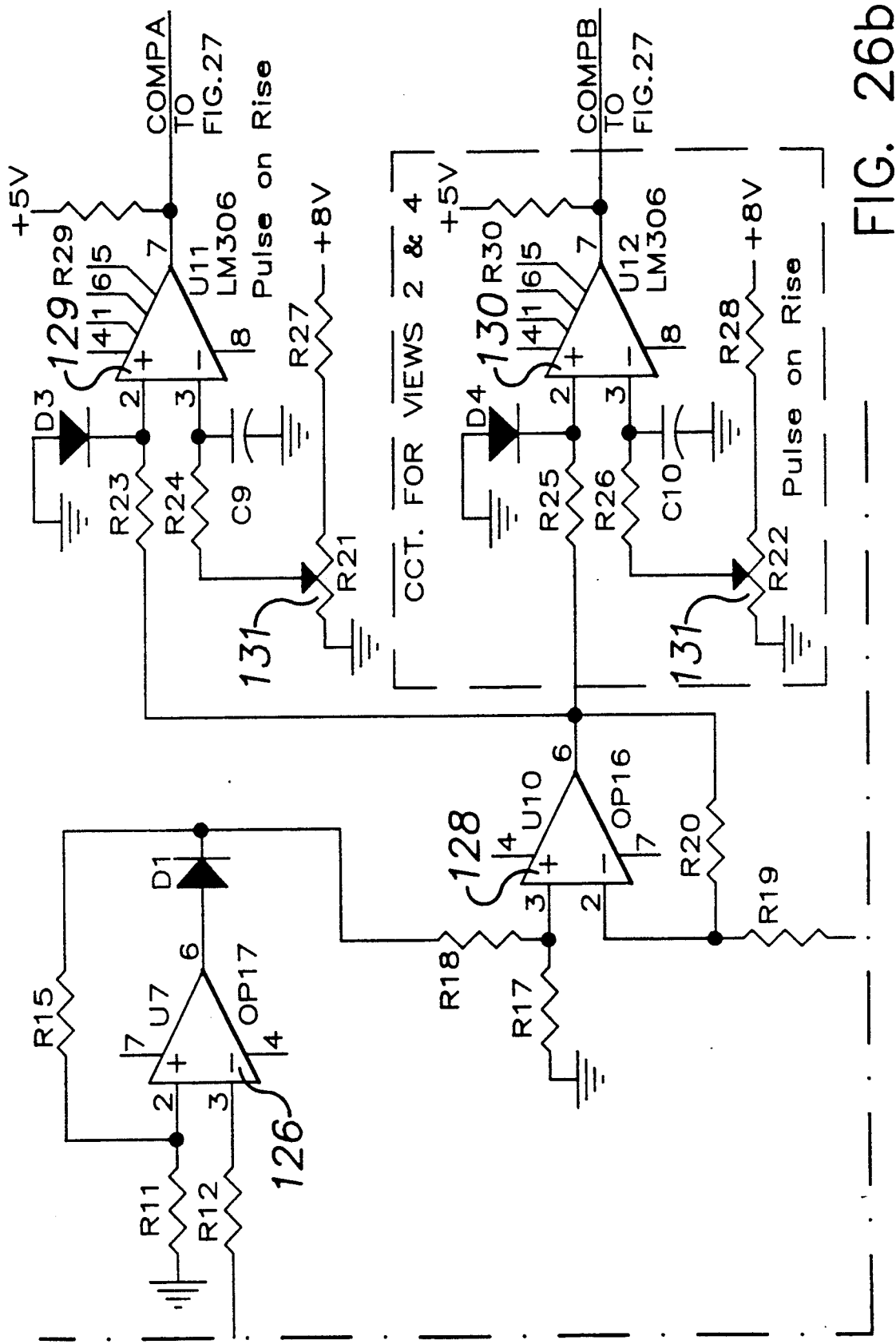
Figure 26C:
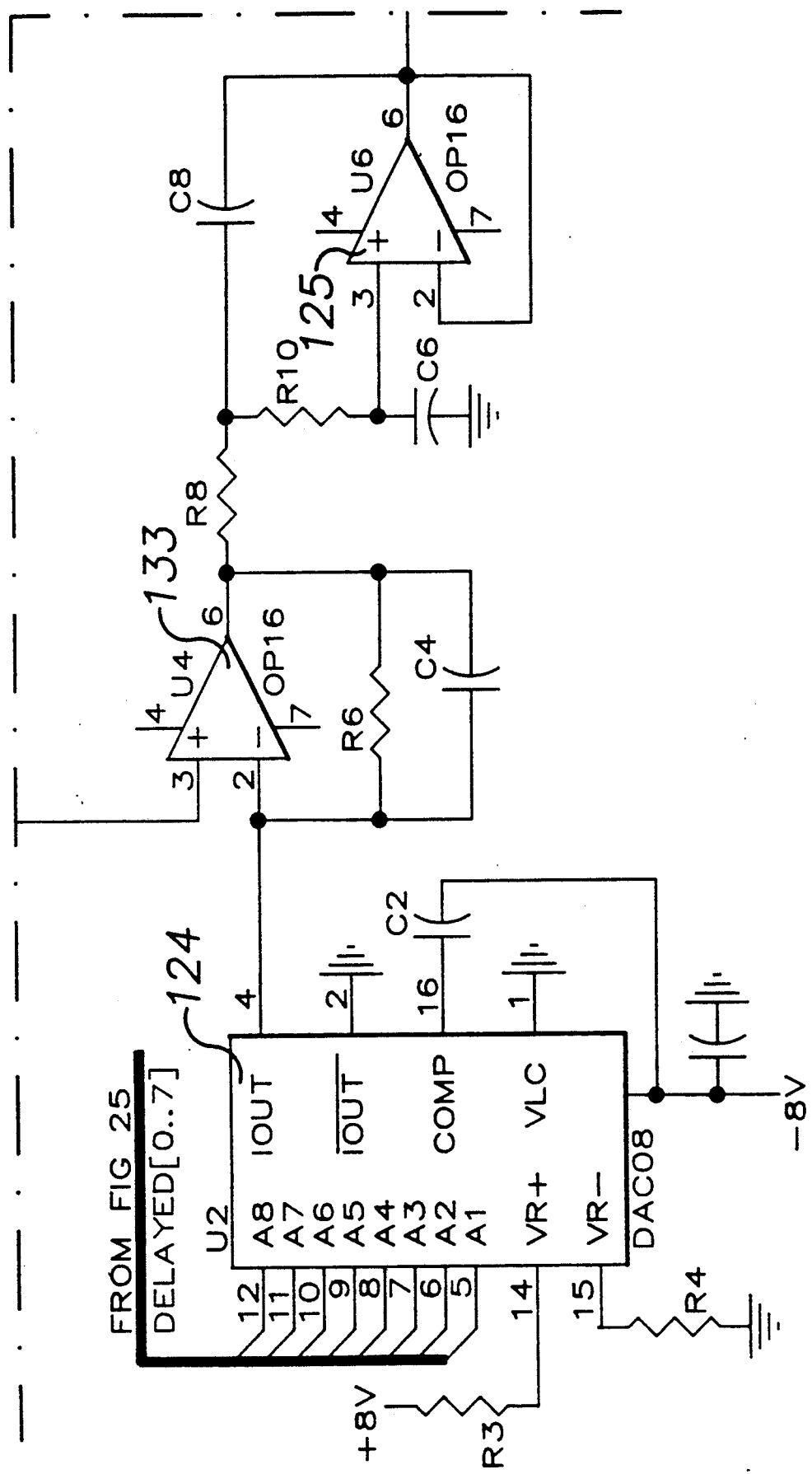

FIGS. 26a to 26d, assembled as shown in FIG. 26e, and collectively referred to herein as FIG. 26, show in more detail the Analog Feature Extraction Means of FIG. 12; circuitry for edge detection.

Figures 27A, 27D:
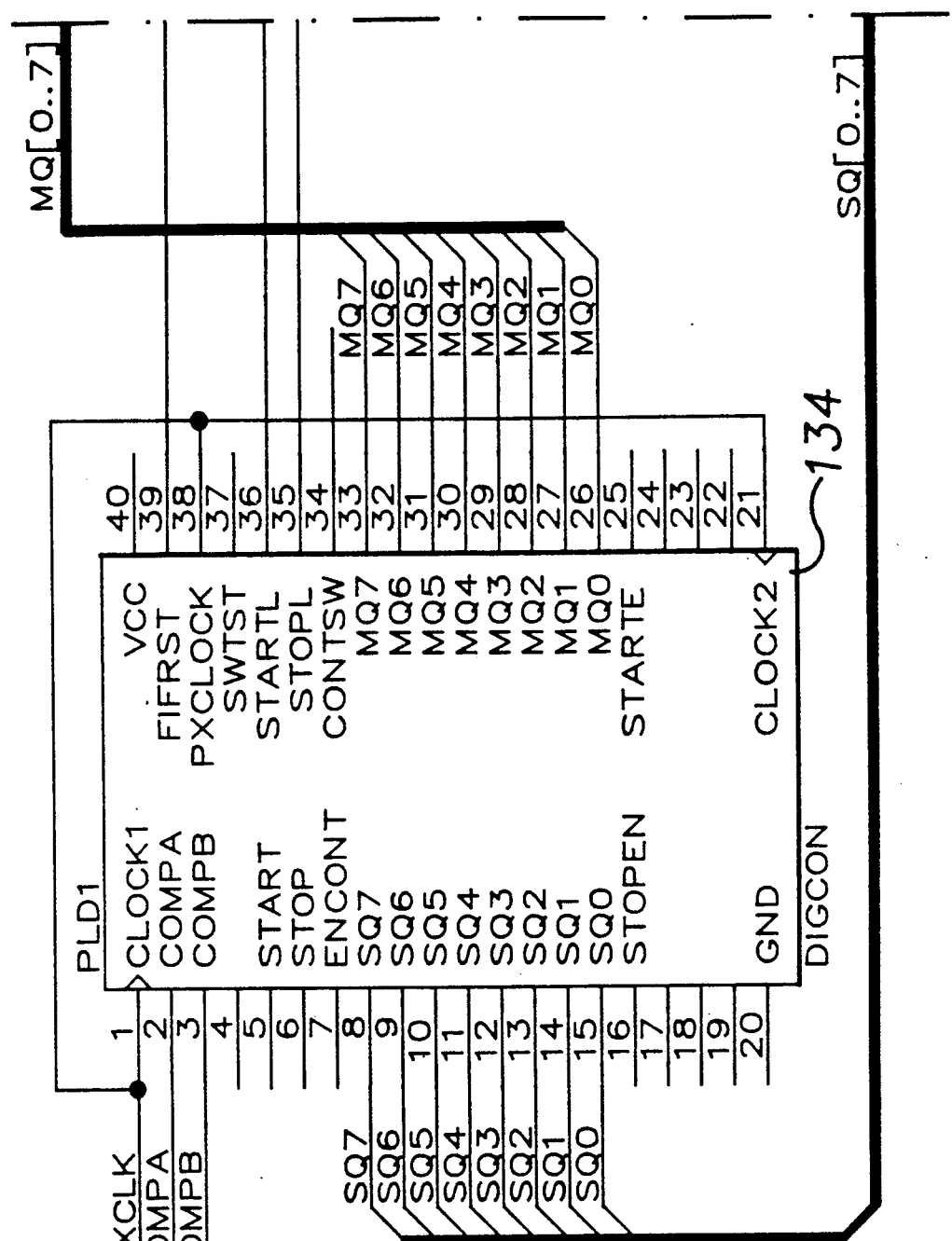
Figure 27C:
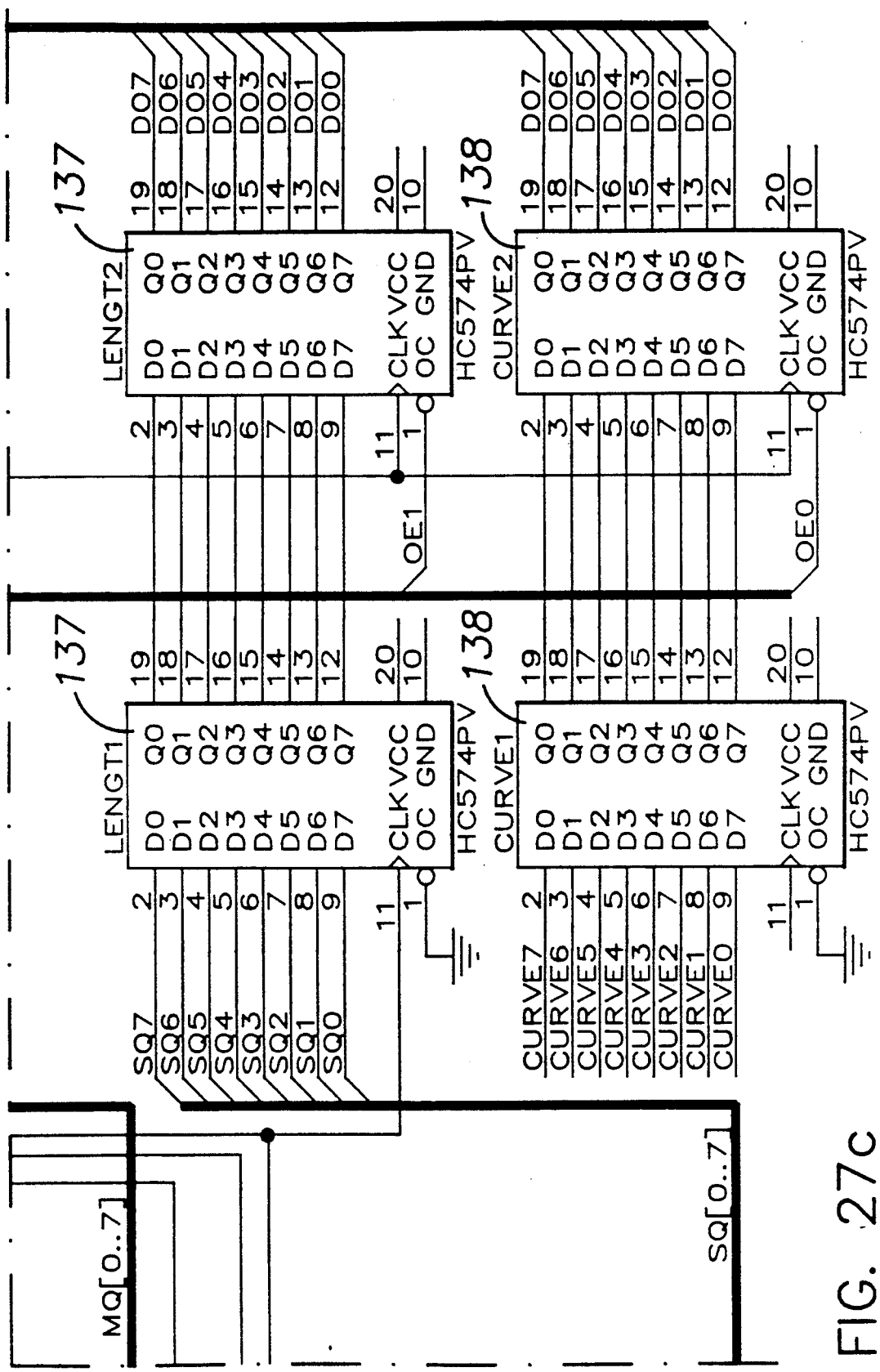

FIGS. 27a to 27c, assembled as shown in FIG. 27d, and collectively referred to herein as FIG. 27, show circuitry to prepare data for the the Digital Processing Means of FIG. 12.

Figure 28A:
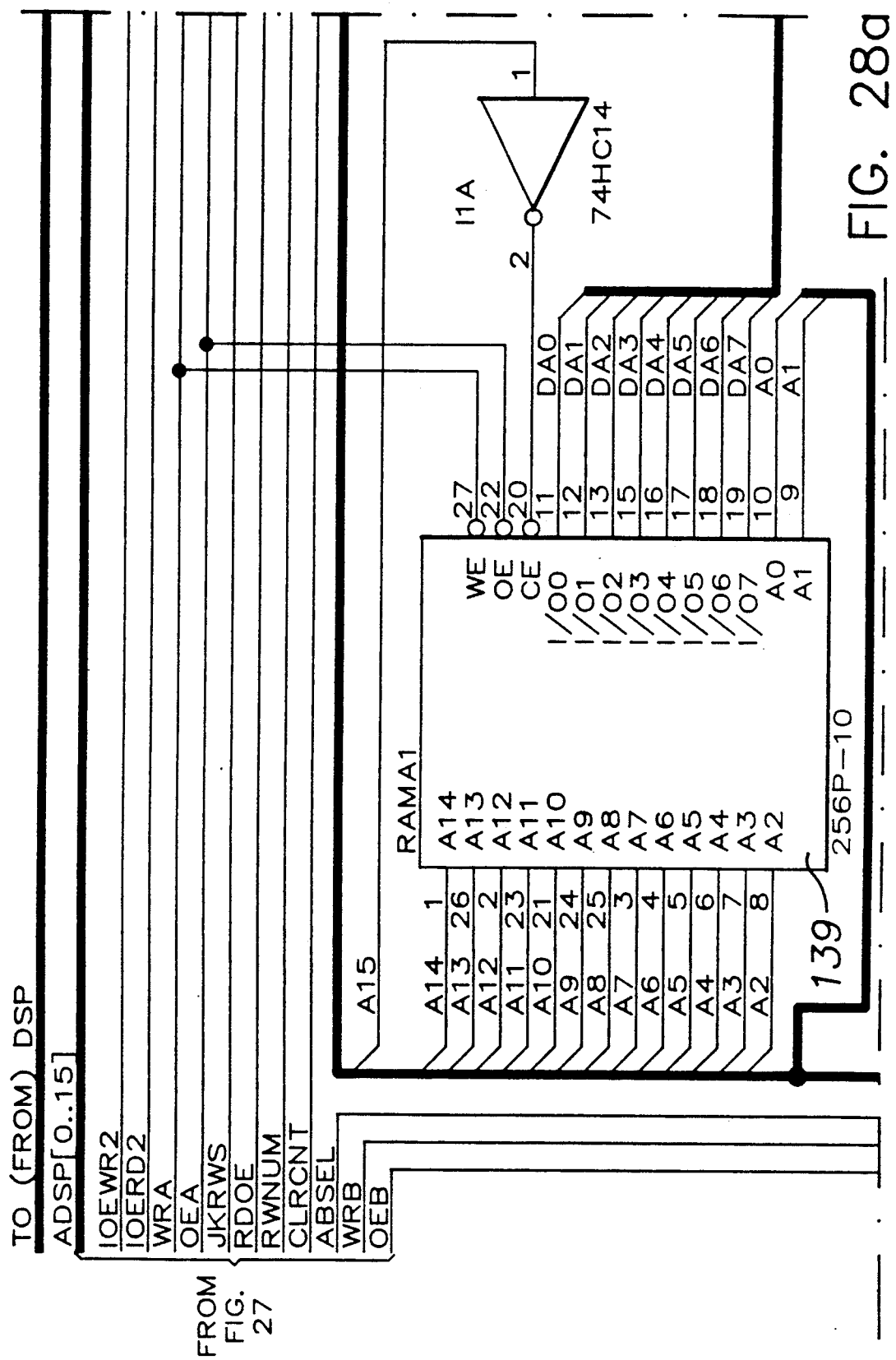
Figure 28B:
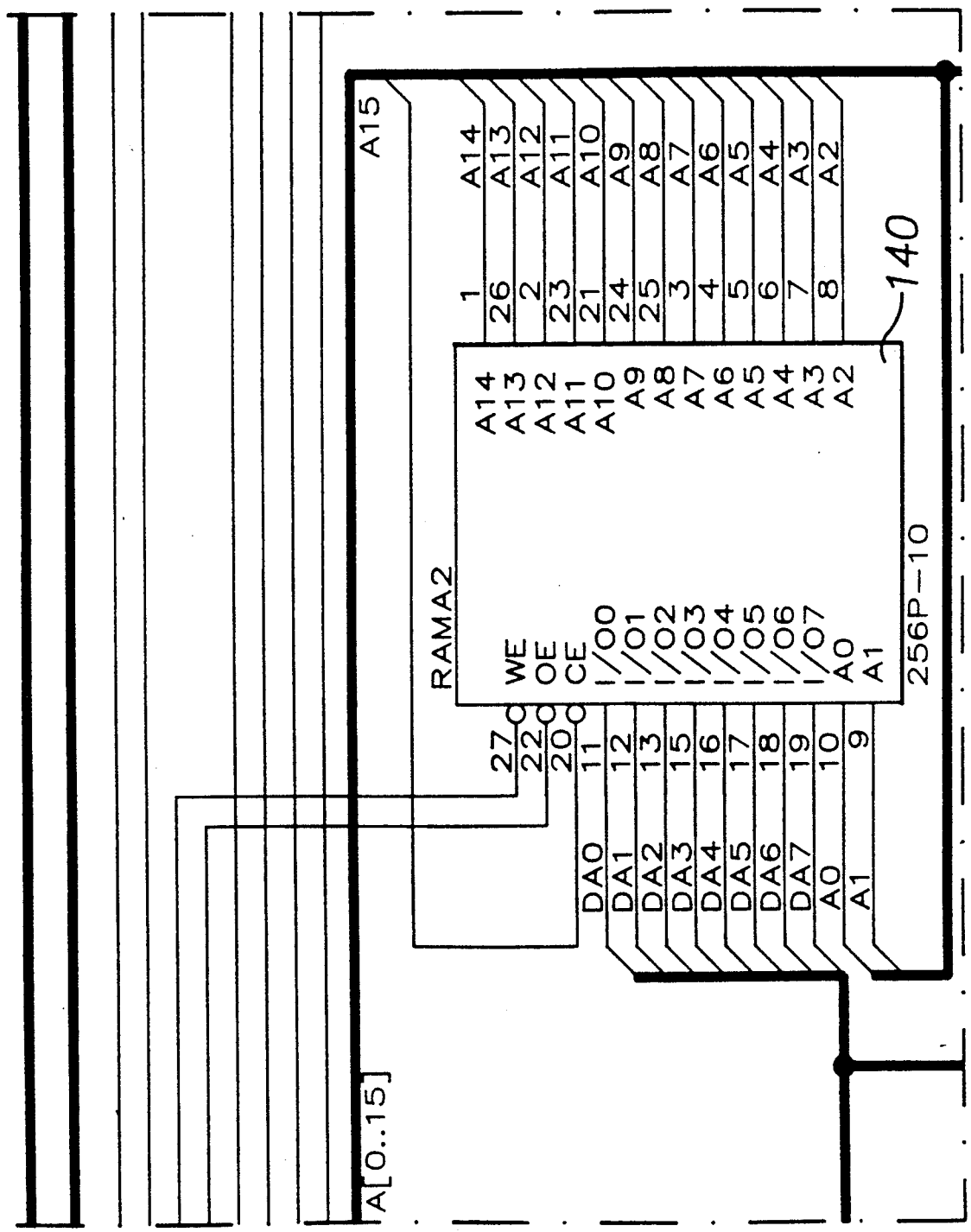
Figure 28C:
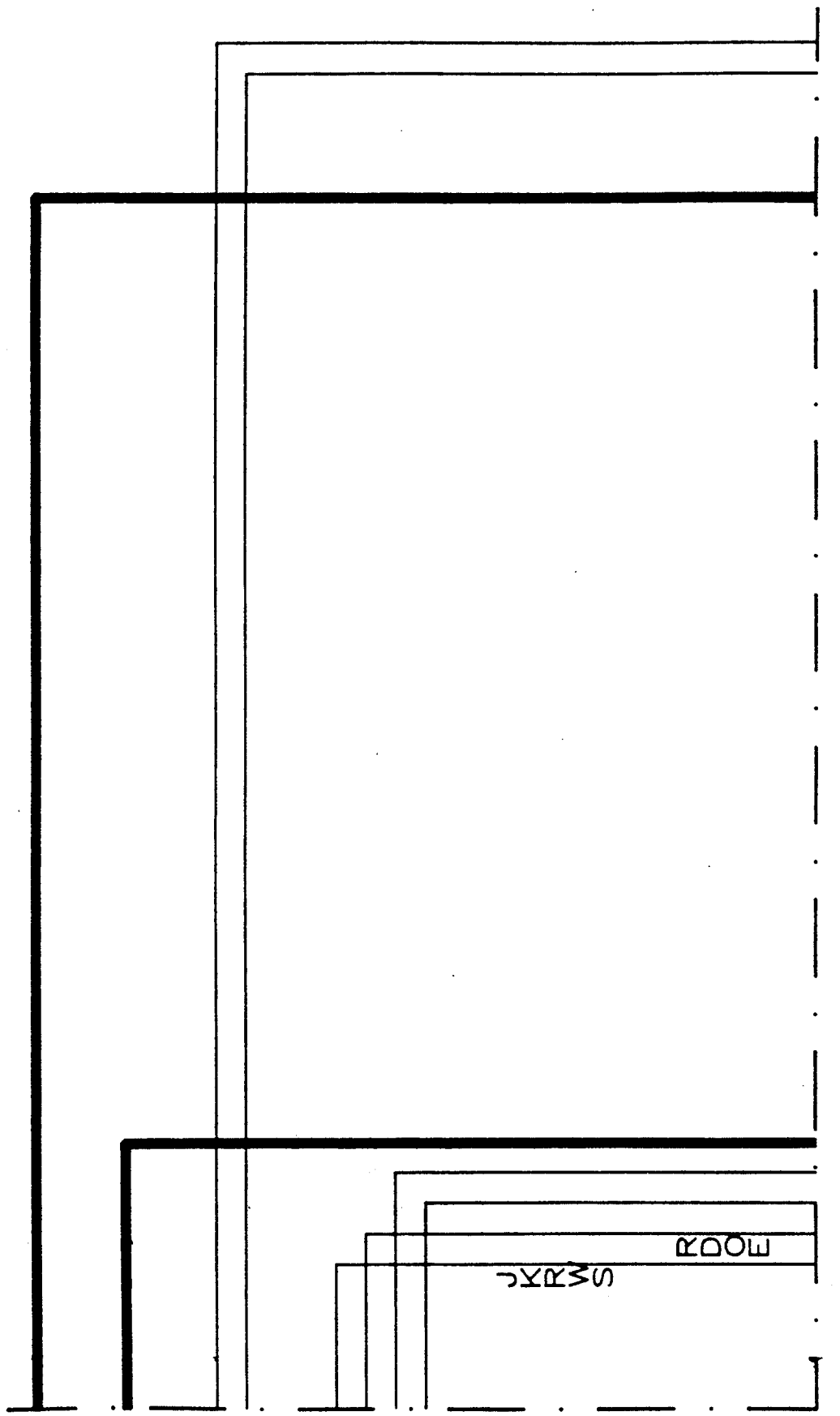
Figure 28D:
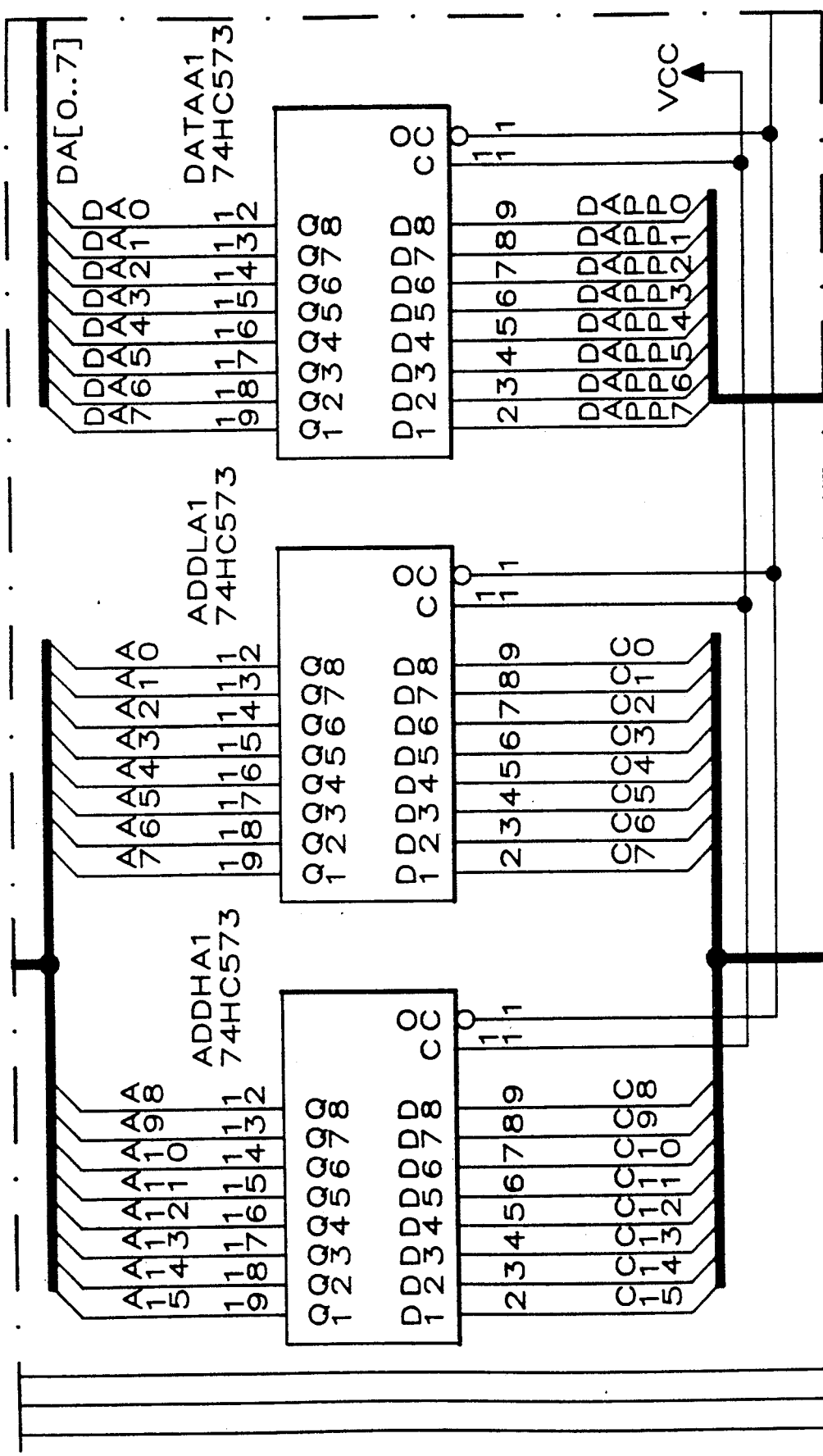
Figure 28E:
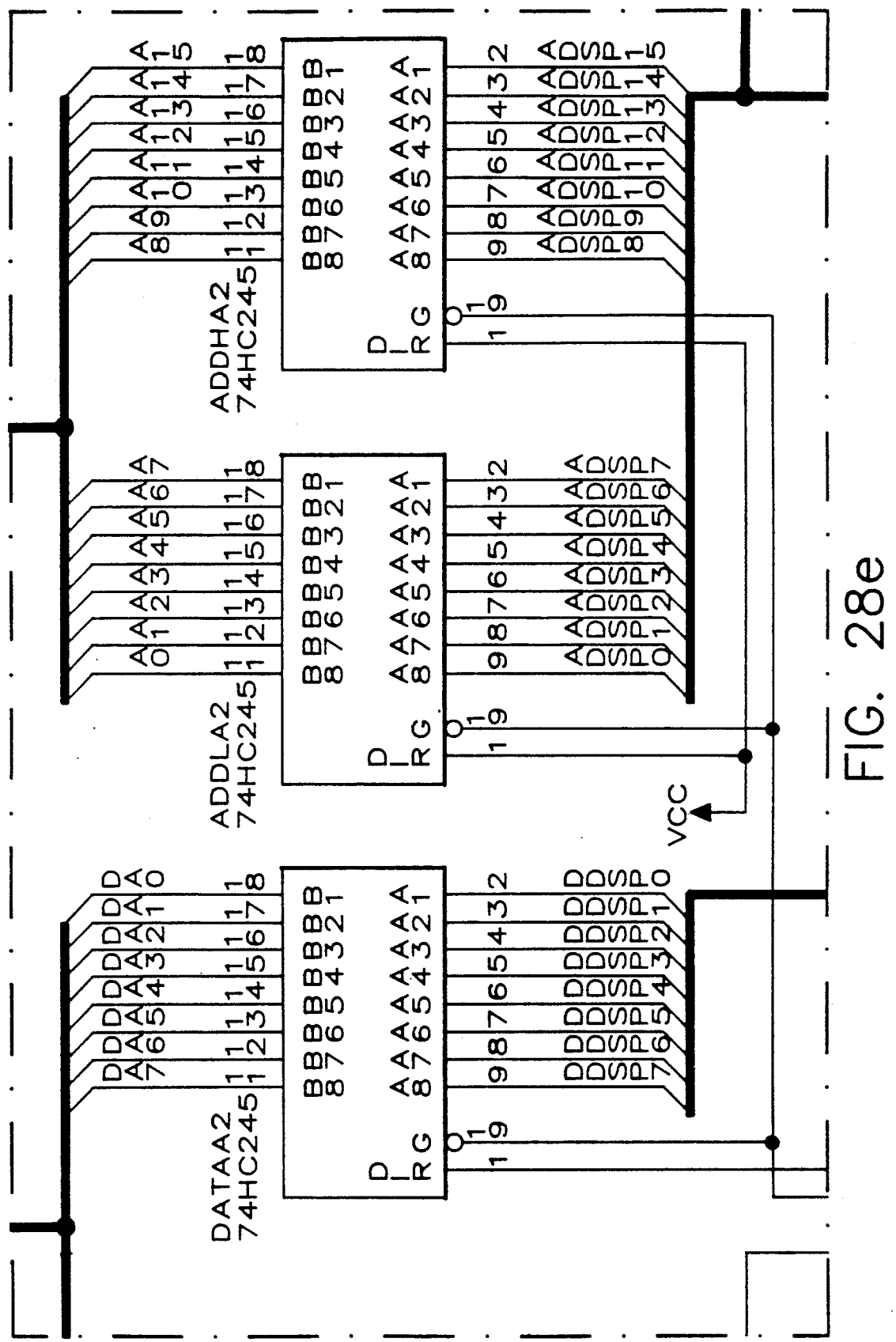
Figure 28F:
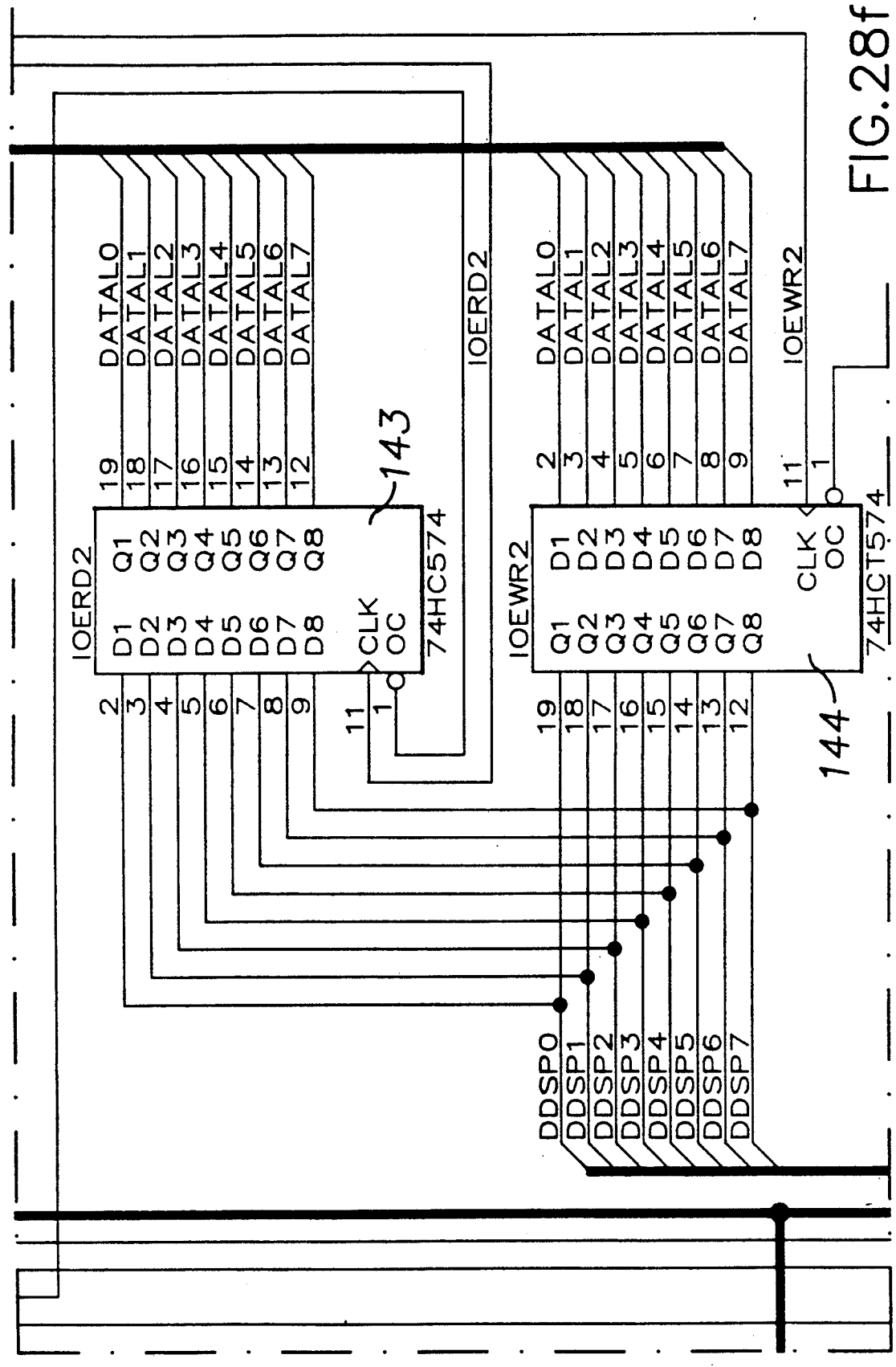
Figure 28G:
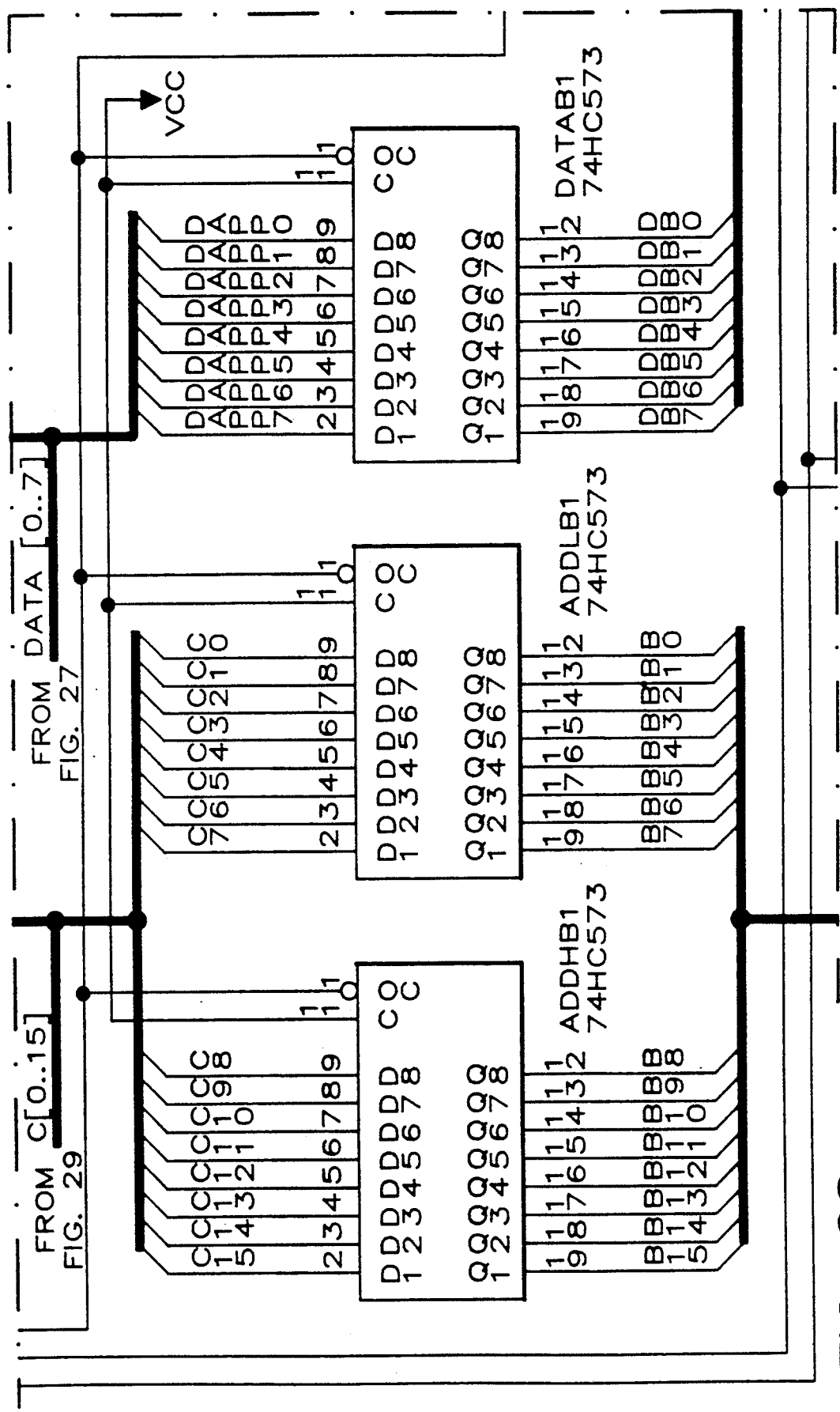
Figure 28H:
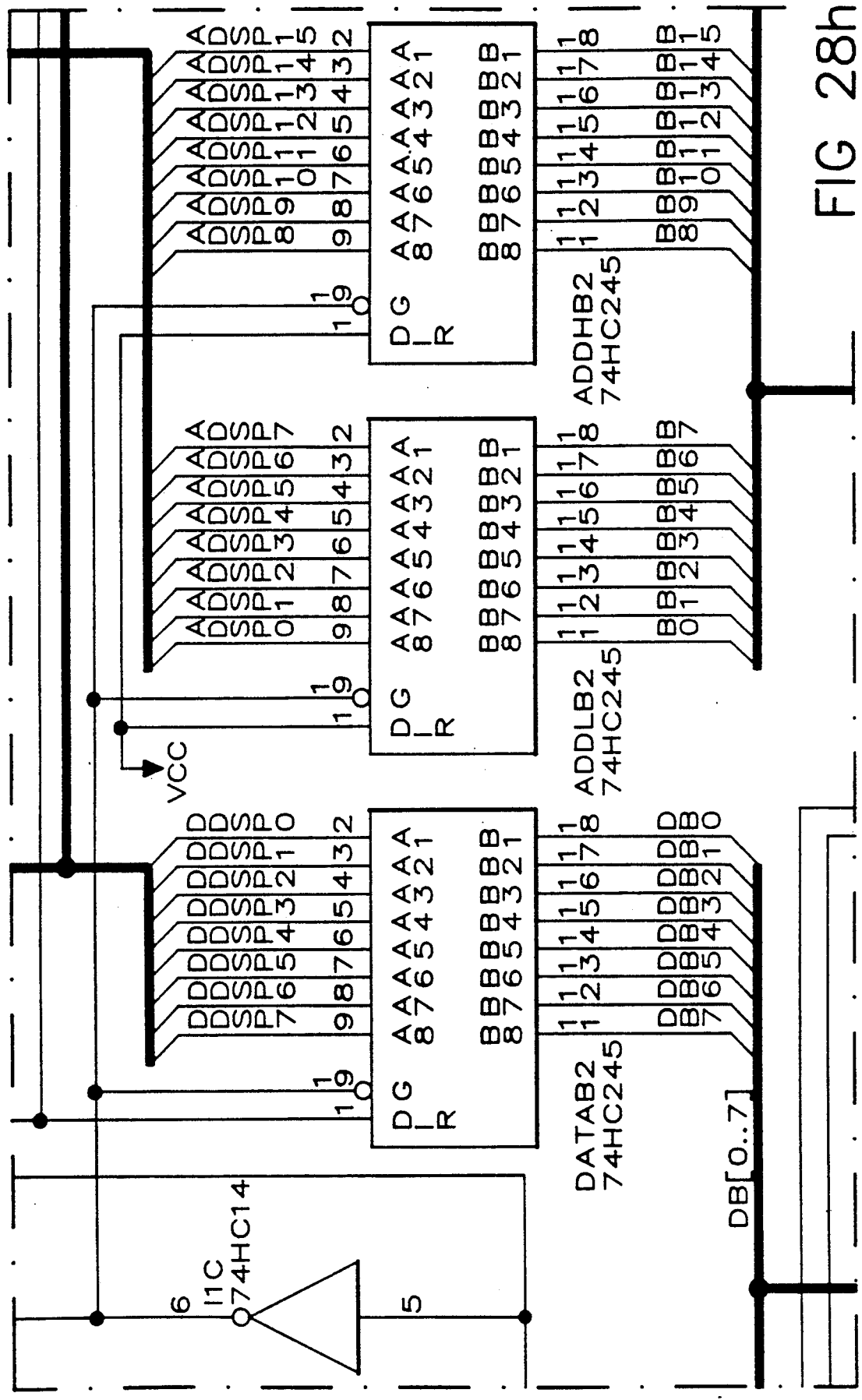
Figure 28I:
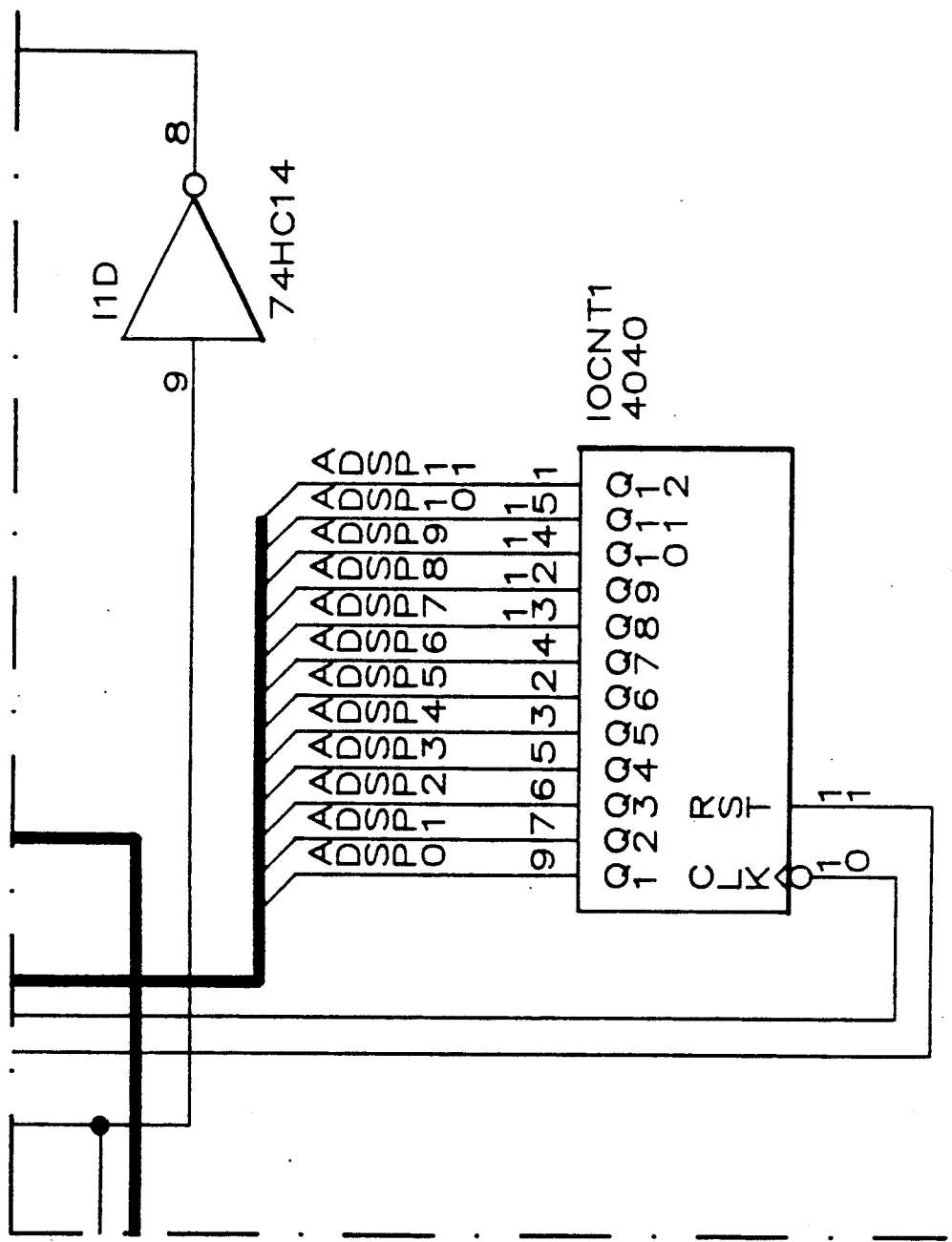
Figure 28J:
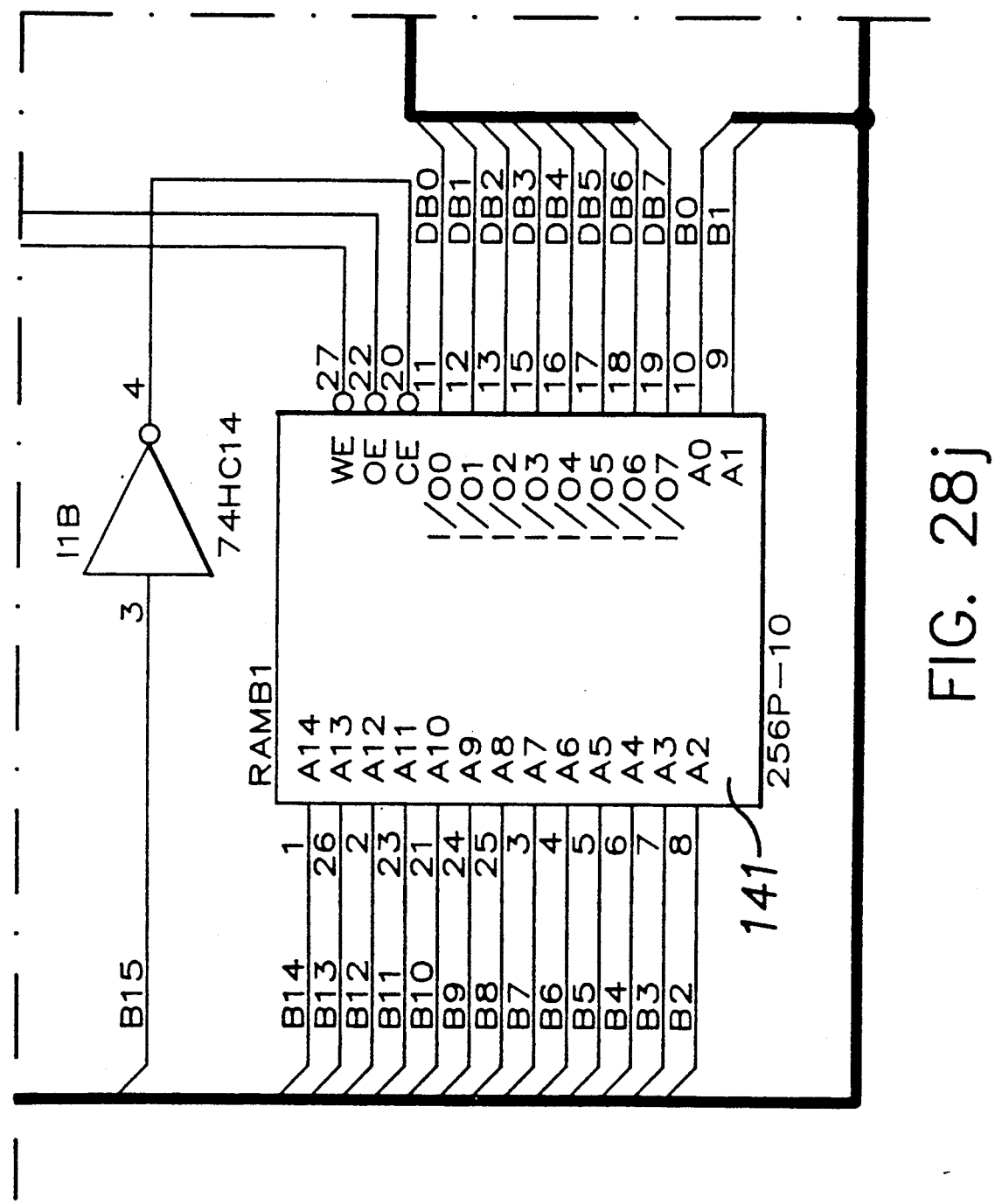
Figure 28L:
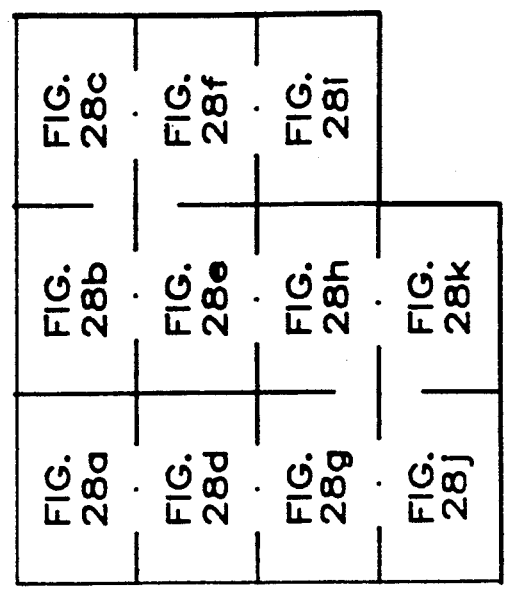
Figure 28K:
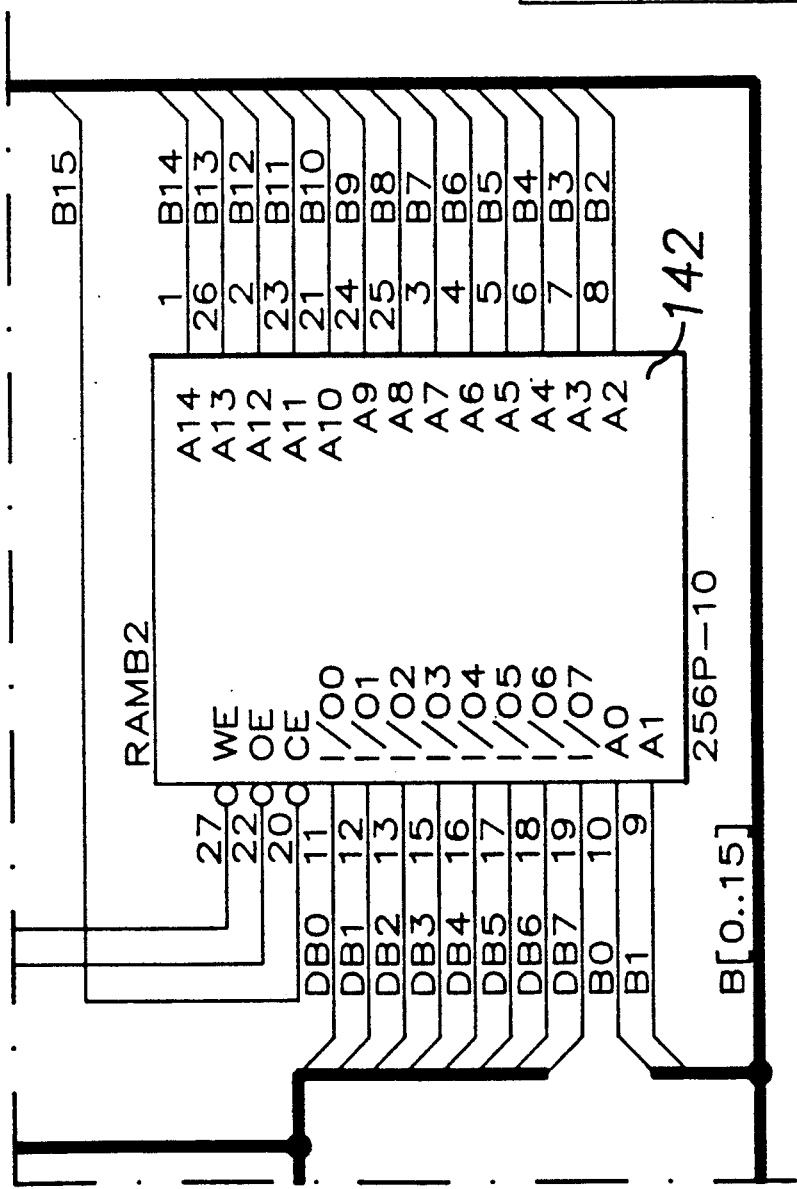

FIGS. 28a to 28k, assembled as shown in FIG. 28l, and collectively referred to herein as FIG. 28, show in more detail further circuitry to prepare data for the Digital Processing Means of FIG. 12; a dual port RAM.

Figure 29A:
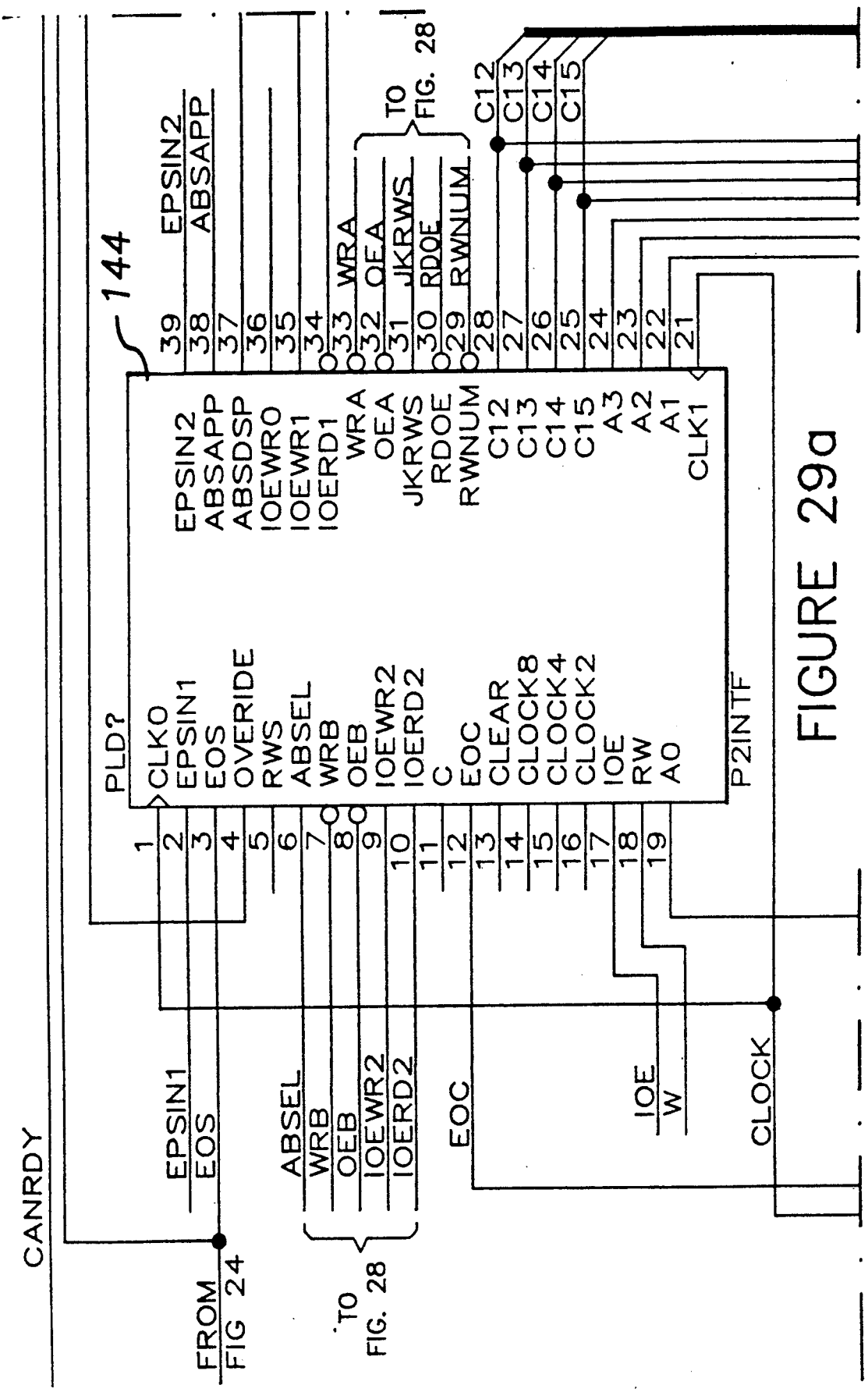
Figure 29B:
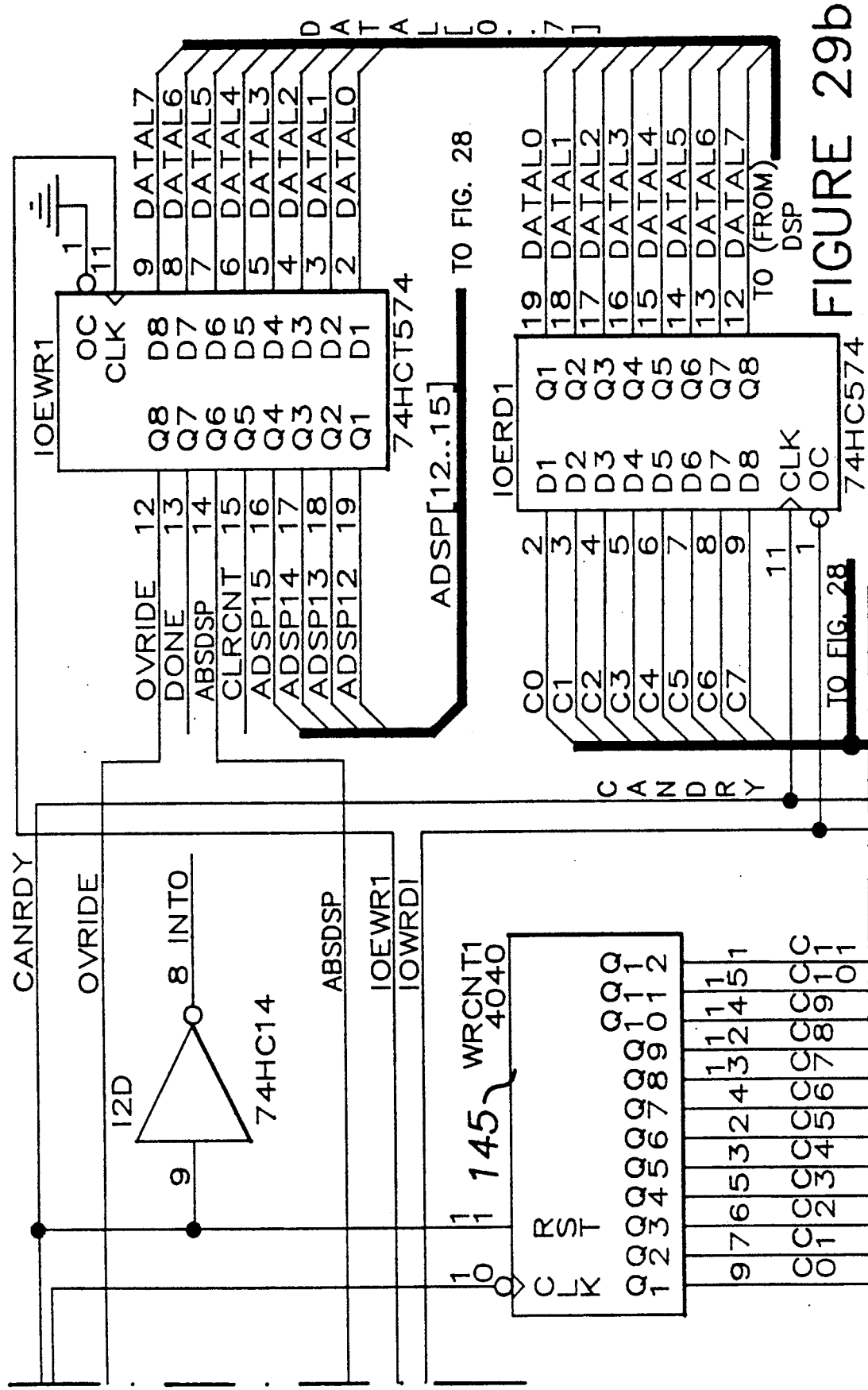
Figure 29C:
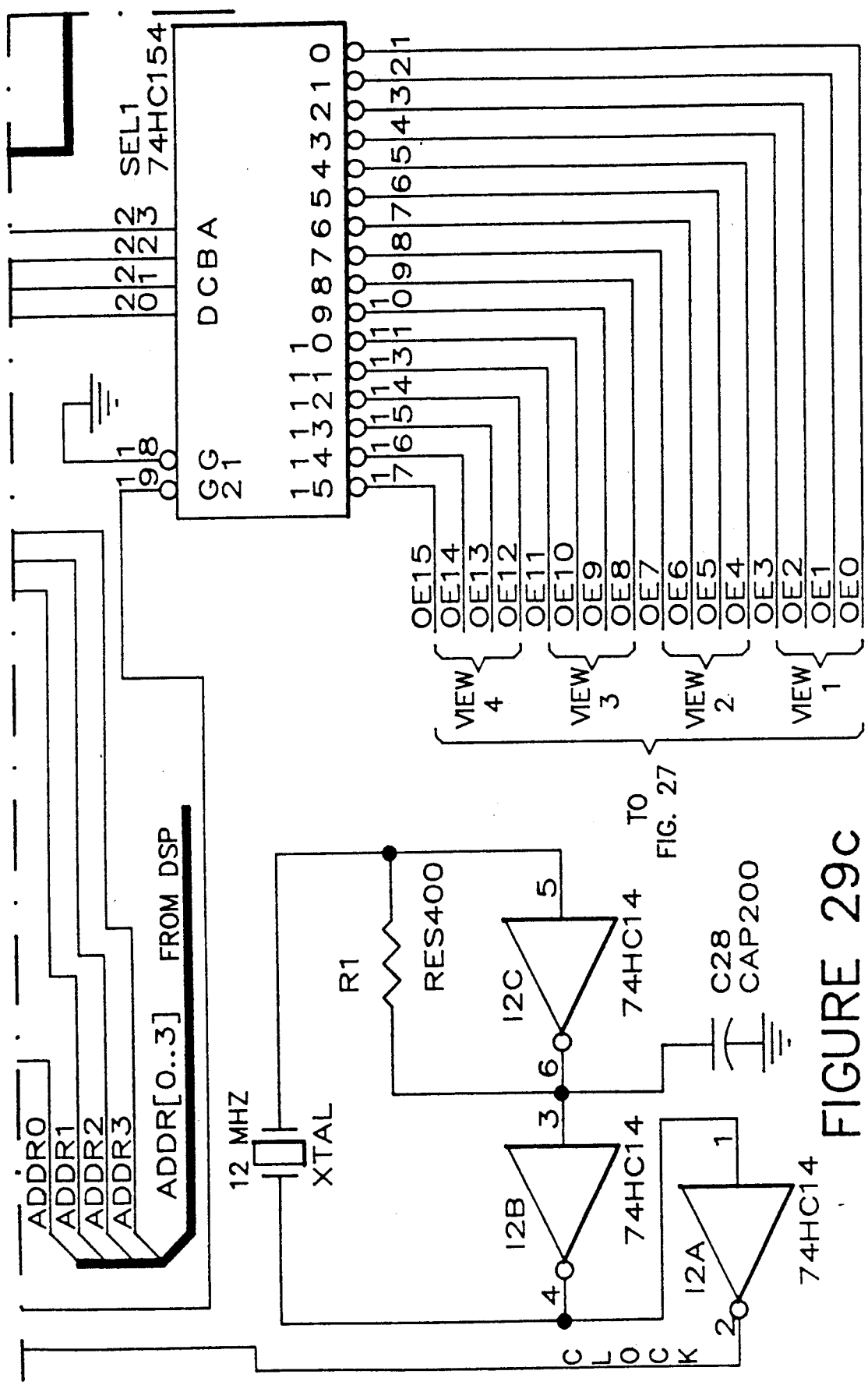
Figure 29D:
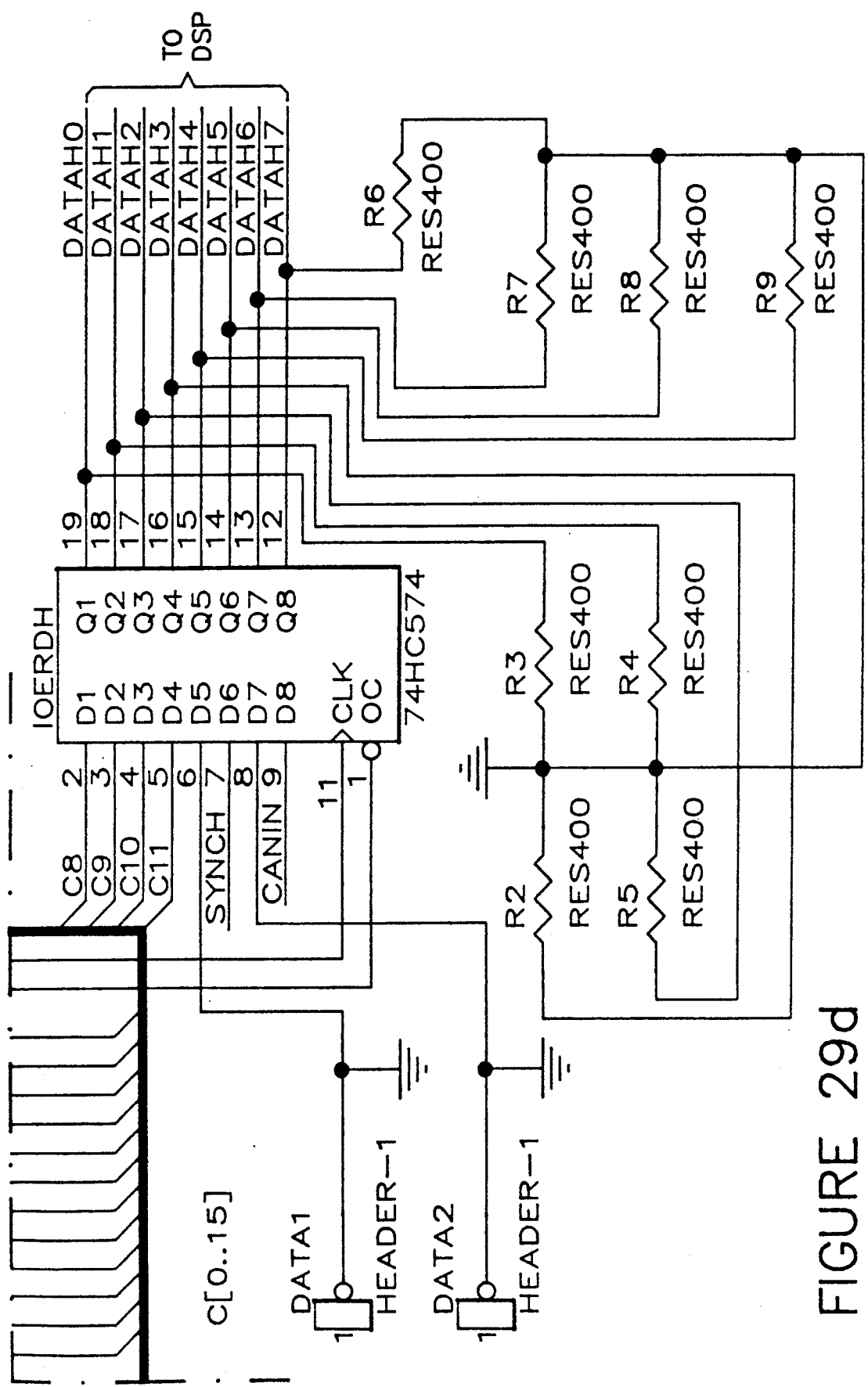
Figure 29E:
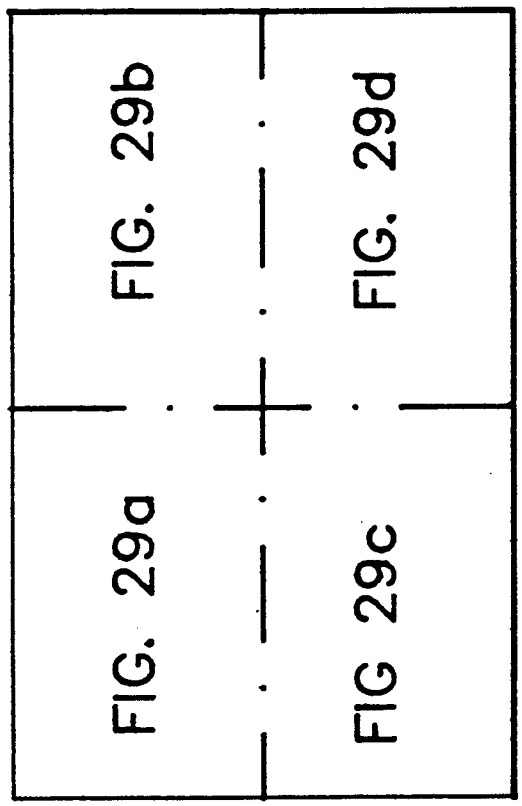

FIGS. 29a to 29d, assembled as shown in FIG. 29e, and collectively referred to herein as FIG. 29, show further circuitry associated with the dual port RAM of FIG. 28; circuitry to control the writing of data into the RAM.

Figure 30:
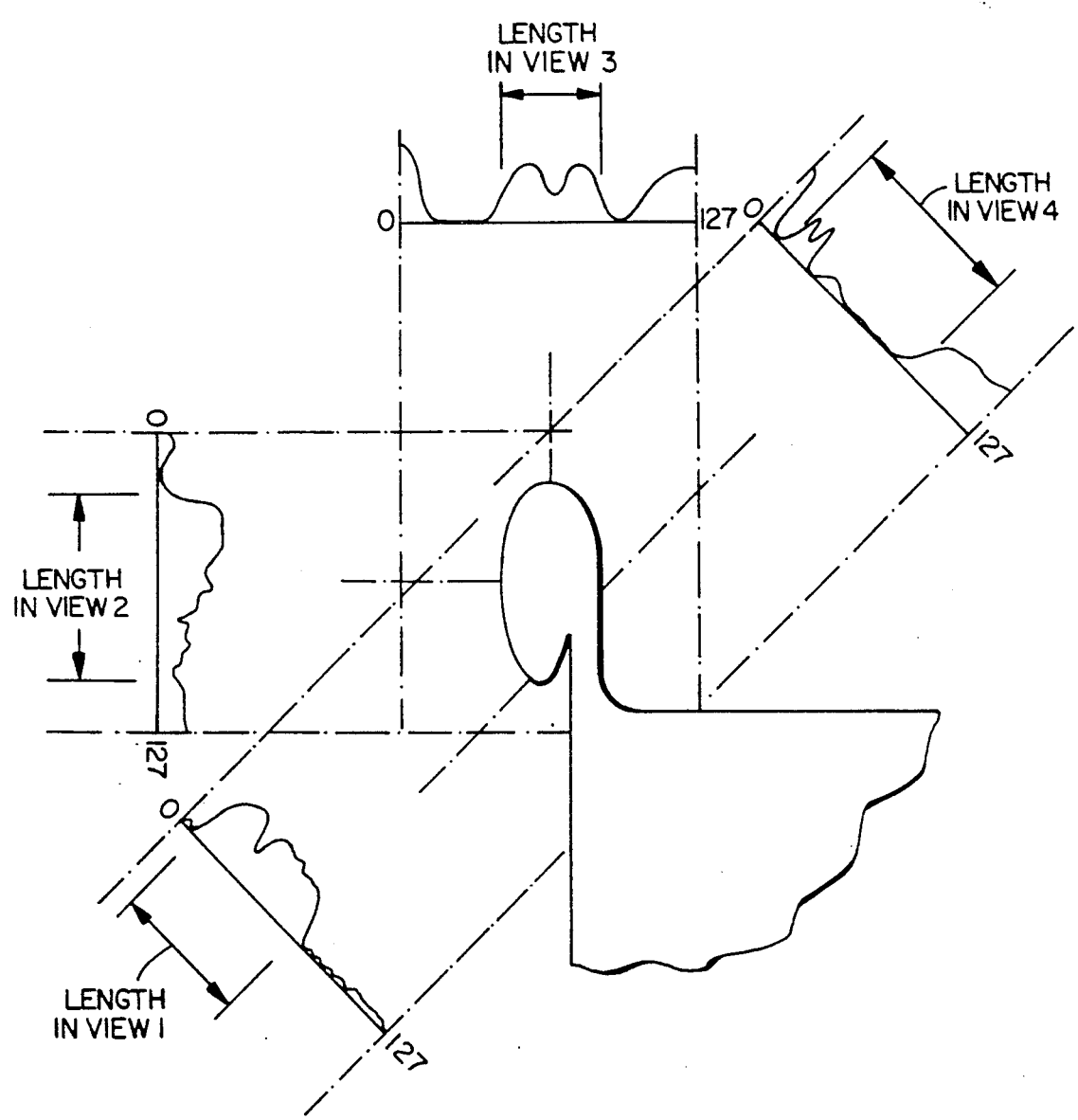

FIG. 30 is a cross section of a typical seam showing the four views used to image the seam. Typical CCD outputs for each view are shown.

Figure 31:
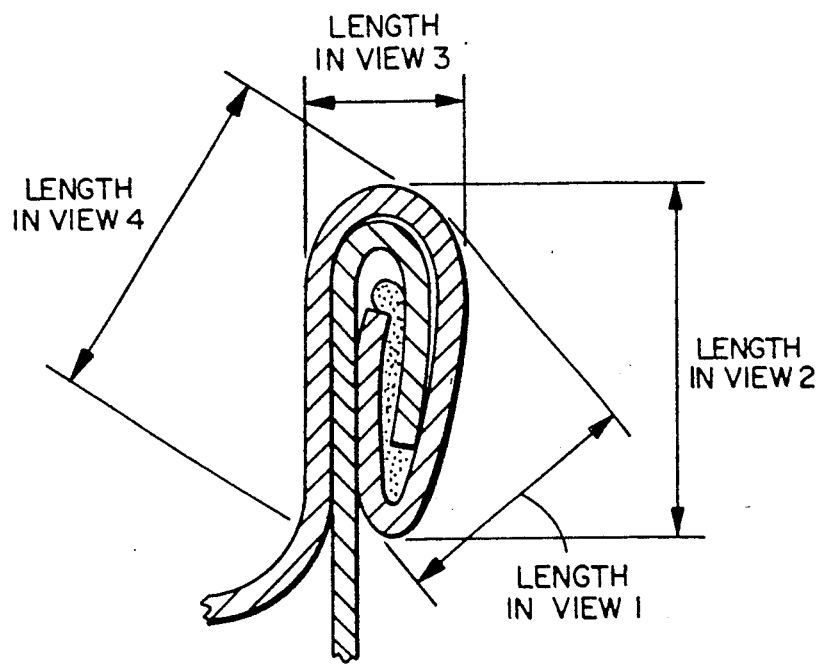

FIG. 31 is a curvate cross section of a typical seam showing the four views used to image the seam. The seam length as determined by these CCD outputs is shown.

Figure 32A:
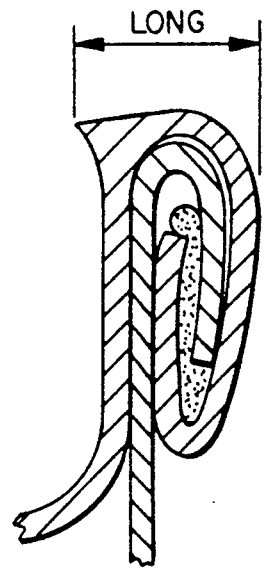

FIG. 32a is a curvate cross section of a double seam with a defect which produces a long dimension in one of the views.

Figure 32B:
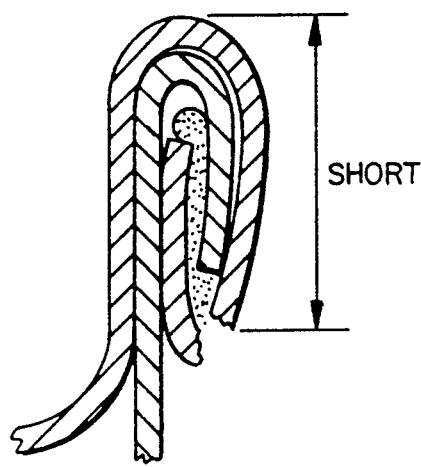

FIG. 32b is a curvate cross section of a double seam with a defect which produces a long dimension in one of the views.

DETAILED DESCRIPTION

The phrase 'length of the seam' will appear frequently in the following discussion. In normal discussions about a can seam such expressions would suggest that the circumferential length of the seam around the can was being spoken of. In what follows, unless noted otherwise, a seam length will refer to a dimension of the curvate cross section of the seam. See FIGS. 30 and 31 for clarification.

The accompanying drawings (FIGS. 1-FIG. 11) illustrate a preferred embodiment of the mechanical and optical aspects involved in the present invention.

Constraints imposed on the system are that (1) it should be able to operate at speeds found on canning and labelling lines in factories, (2) the complete circumference of the can double seam should be inspected.

Figure 1:
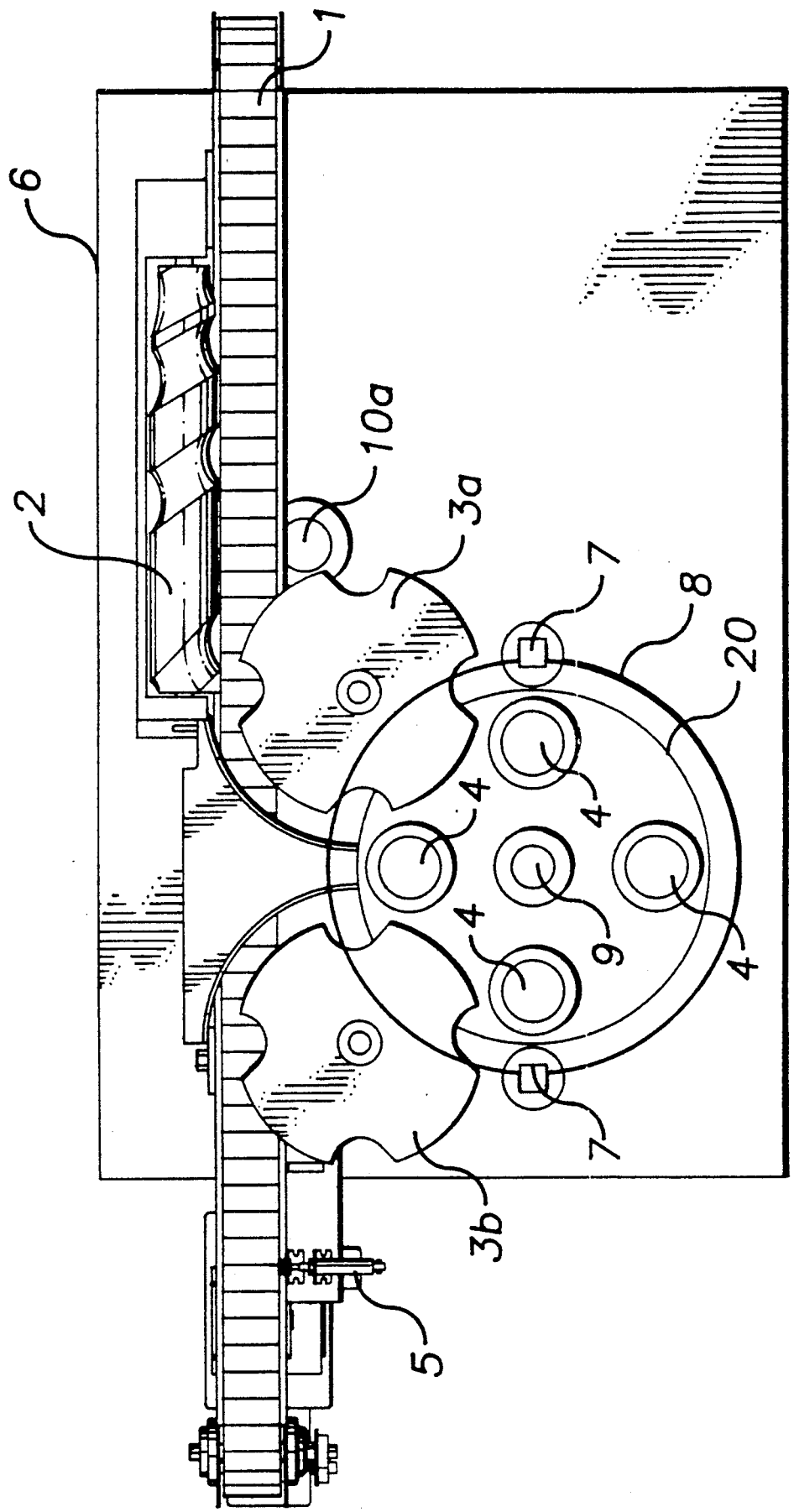
FIG. 1 is a plan view of the mechanical portions of a preferred embodiment of a machine for inspecting the seams of cans in accordance with the present invention.

As FIG. 1 shows, the conveyor (1), worm (2), and starwheel arrangement (3a & 3b) are conventional and compatible with normal factory operations. These elements are designed to provide a steady supply of cans to the inspection platforms (4). A can is fed from the conveyor (1) via the worm (2) into the input starwheel (3a) and deposited on an inspection platform (4). Subsequently, the can will be released to the output starwheel (3b) and delivered back to the conveyor.

An important item shown in FIG. 1 is the eject mechanism (5). When the electronic aspects of the preferred embodiment determine that the can seam is defective, this air powered piston will be activated to remove the undesirable can from the production line.

The rectangular item 6 of FIG. 1 is the base plate which supports the various mechanical items in their proper positions.

The two posts (7) serve to support the protective shroud (8). Item 9 is the central shaft of the inspection rotor. More precisely, it is the top view of that portion of the inspection rotor shown in more detail in FIG. 8.

Figure 2:
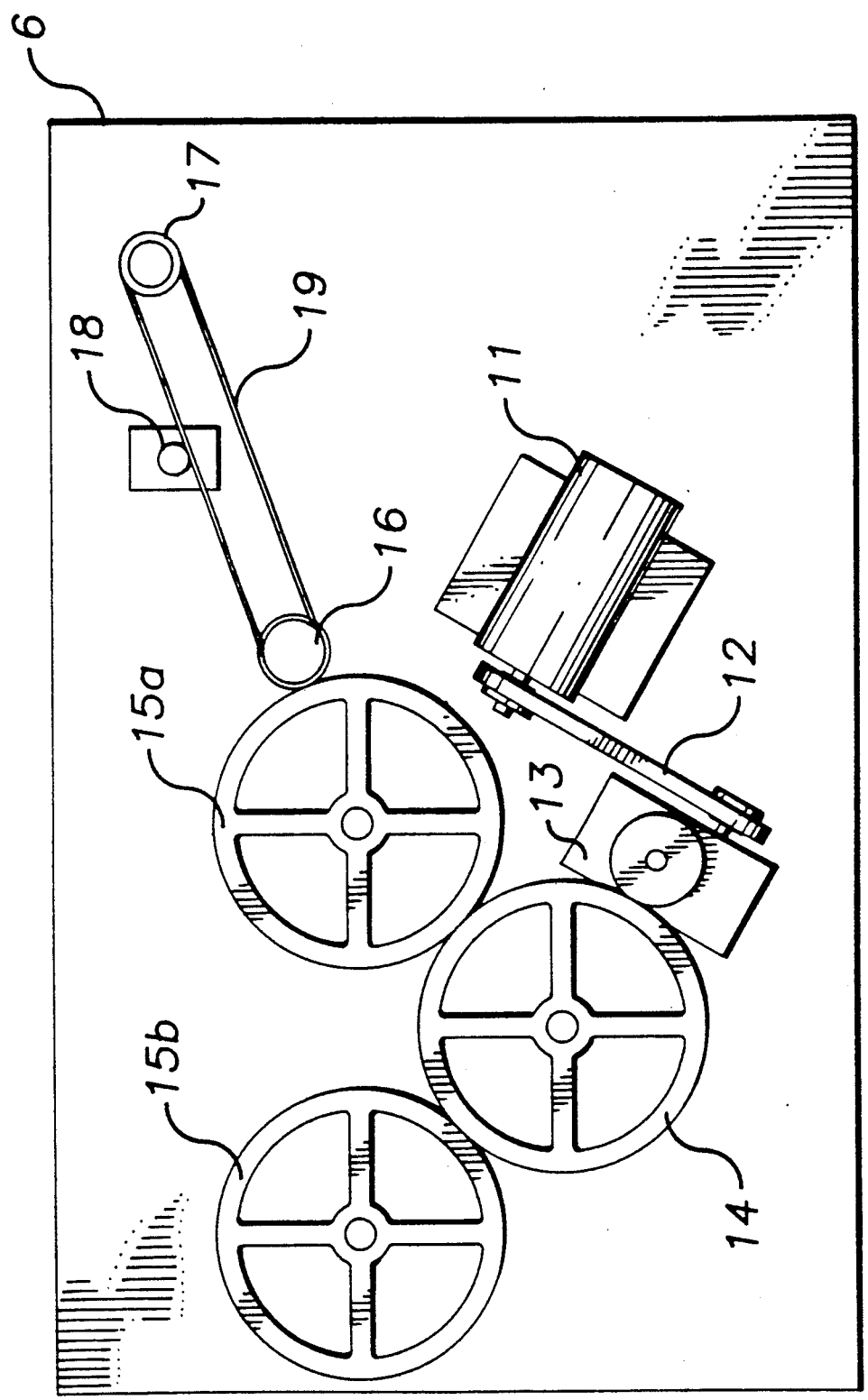
FIG. 2 is a plan view showing the arrangement for driving the major mechanical portions of FIG. 1.
Figure 7:
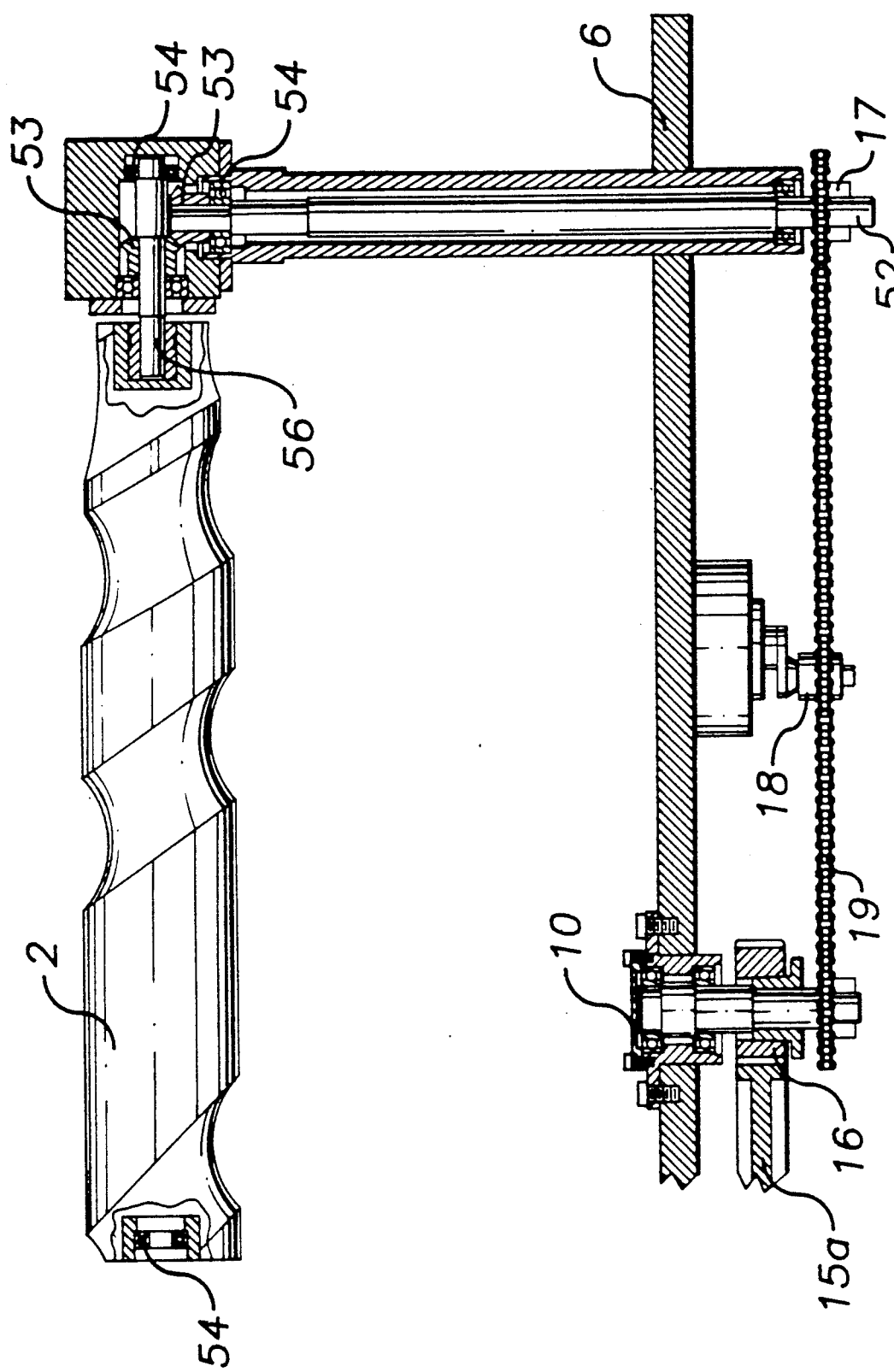
FIG. 7 is a cross section of the drive mechanism of the worm shown in FIG. 1.

Item 10 is the mount for the takeoff gear (16) shown in FIGS. 2 and 7.

FIG. 2 shows mechanical components used to power the various moving components of FIG. 1. The items shown in FIG. 2 are all suspended beneath the base plate (6). The electric motor (11) powers the gearbox (13) via the V-belt (12). (To keep the drawing simple, gear teeth are not shown on the various engaging components.) Gear 14 drives the inspection rotor shaft (21, FIG. 3), while 15a and 15b drive the starwheels 3a and 3b respectively. Power is taken off 15a by 16 and delivered, through chain 19 and sprocket 17, to drive the worm 2. Idler 18 provides chain tension. The worm drive is further detailed in FIG. 7.

Figure 3:
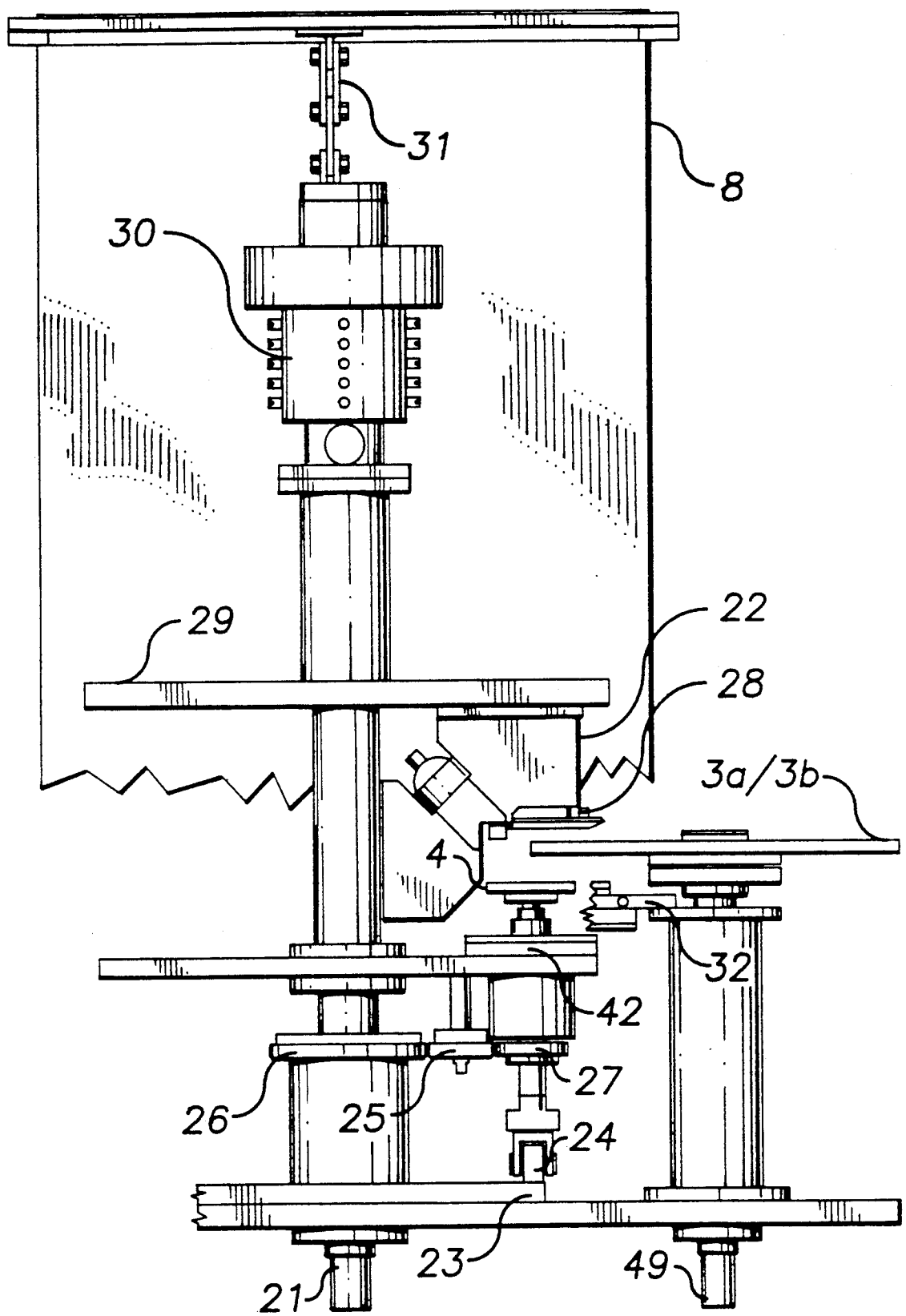
FIG. 3 is a side view of the inspection rotor, a can platform, and a starwheel of the preferred embodiment.

FIG. 3 shows, in side view, the relationships among the inspection rotor (20), an inspection platform (4), an optics module (22), and starwheel (3a or 3b). By way of convention the term 'inspection rotor' refers not just to the specific item labelled 20 in FIG. 3 but to the whole group of items that rotate around the same central shaft (21) as does plate 20. The inspection platform (4), is thus part of the inspection rotor, as is the optics module (22).

Referring now to both FIGS. 1 and 3, more details of the mechanical movement may be given. The anti-clockwise rotating starwheel 3a devivers a can to inspection platform 4 (the gear arrangement of FIG. 2 must provide appropriate synchronization). The inspection platform (4), as part of the inspection rotor (20) moves in a clockwise direction around shaft 21 which is driven by gear 14. At the same time, the sun gear (26), idler gear (25) and planetary gear (27) cause the inspection platform (4) to rotate in a counterclockwise direction about the center of its own support shaft (see FIG. 5). This arrangement of counter rotating the can platform (4) as it moves in a clockwise sense from input starwheel (3a) to output starwheel (3b) is used to minimise the shearing forces that the contents of cans undergoing inspection are subject to. For some food products large centrifugal forces may reduce product quality.

The gearing of rotating elements is such that as the entire inspection rotor rotates 180 degrees in the clockwise direction the inspection platform and can rotate in the opposite direction by (slightly more than) 180 degrees. The result of these two motions is to present in excess of 360 degrees of the can seam to the optics with minimum rotation of the can and contents (relative to the fixed frame). Given the pickup and drop off points of cans on the starwheels 3a and 3b this also provides adequate time for the can to be fully seated on a platform 4 before imaging actually begins, and gives time for somewhat more than 360 degrees of the can circumference to be examined before the can is dropped off.

Also shown in FIG. 3 is a cam track (23) and cam follower (24). A can sitting on can platform (4) would tend to slide off the platform as the inspection rotor moves it from starwheel to starwheel. This is prevented by lifting the can and platform, via the underlying cam (23), so that the double seam of the can is pressed against seam rollers (28, also labelled 70 in FIG. 9) situated above the can platform.

Figure 9:
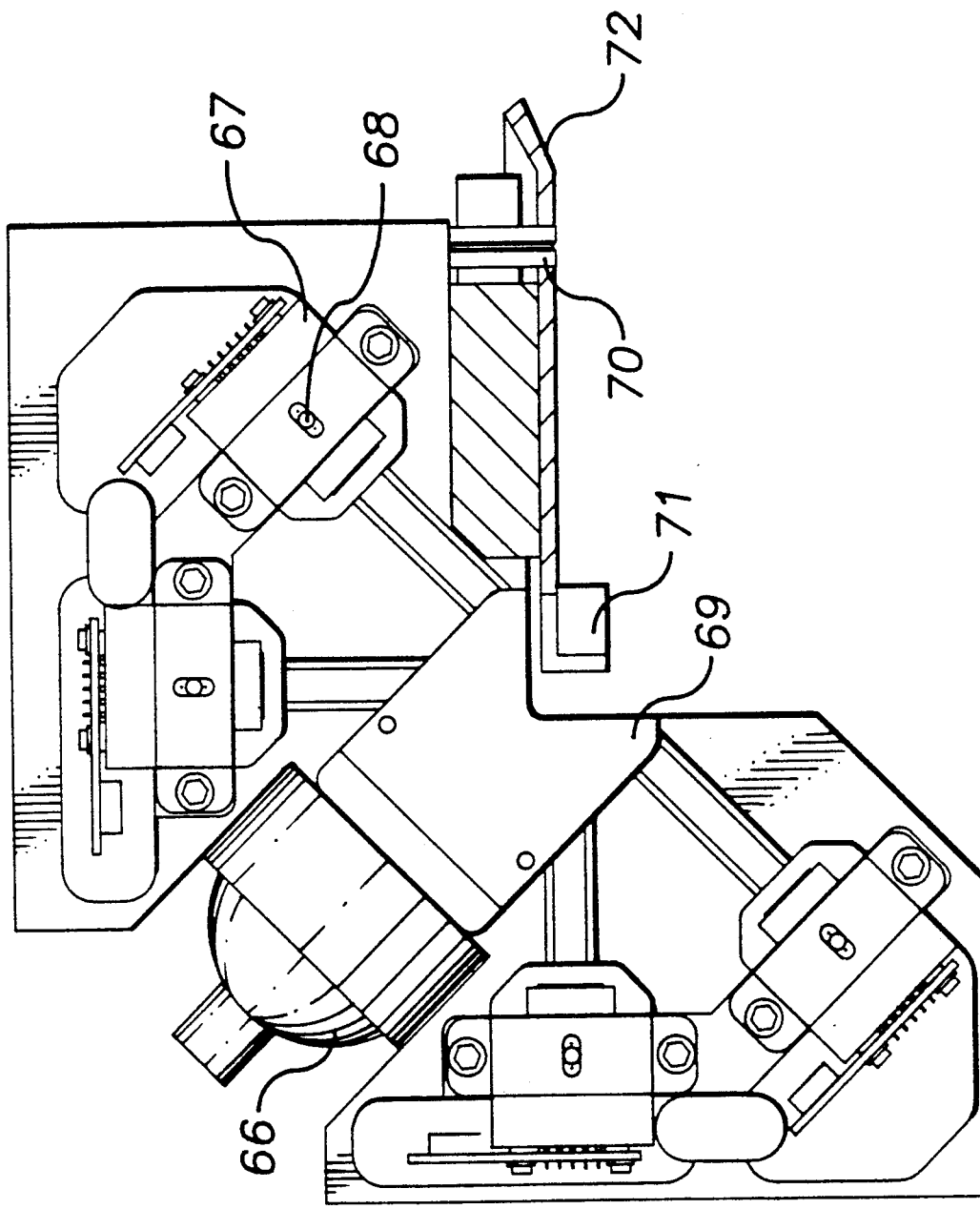
FIG. 9 is a side view of one of the optics modules outlined in FIG. 3.

The raising of the platform and can against the rollers, besides restricting unwanted motion, also serves to locate the double seam in a position suitable for viewing by the optics system (FIG. 9).

As shown in FIG. 1, the inspection rotor (2.6/1.6) of the present embodiment has four inspection platforms. There is an optics system associated with each. Signal processing circuitry before multiplexing is divided into 2 similar parts. Each part handles data provided by a pair of optical heads opposite each other on the rotor. For such a pair of optical heads, just as one can is about to be examined, its predecessor is being finished. Since there is no overlap in the signals coming from the paired heads the analog multiplexer of figure need only merge the signals from two cans at any one time.

Item 29 of FIG. 3 is part of the inspection rotor and revolves with shaft 21. The four optics module of the preferred embodiment are suspended beneath plate 29. Not shown in FIG. 3 are the electronic components that are represented by blocks 12.1 and 12.2 of FIG. 12. The signal processing required to prepare and transmit the gathered data over the fibre optic link to the stationary outside world is performed by electronic components located in card cages mounted on top of plate 29.

Figure 8:
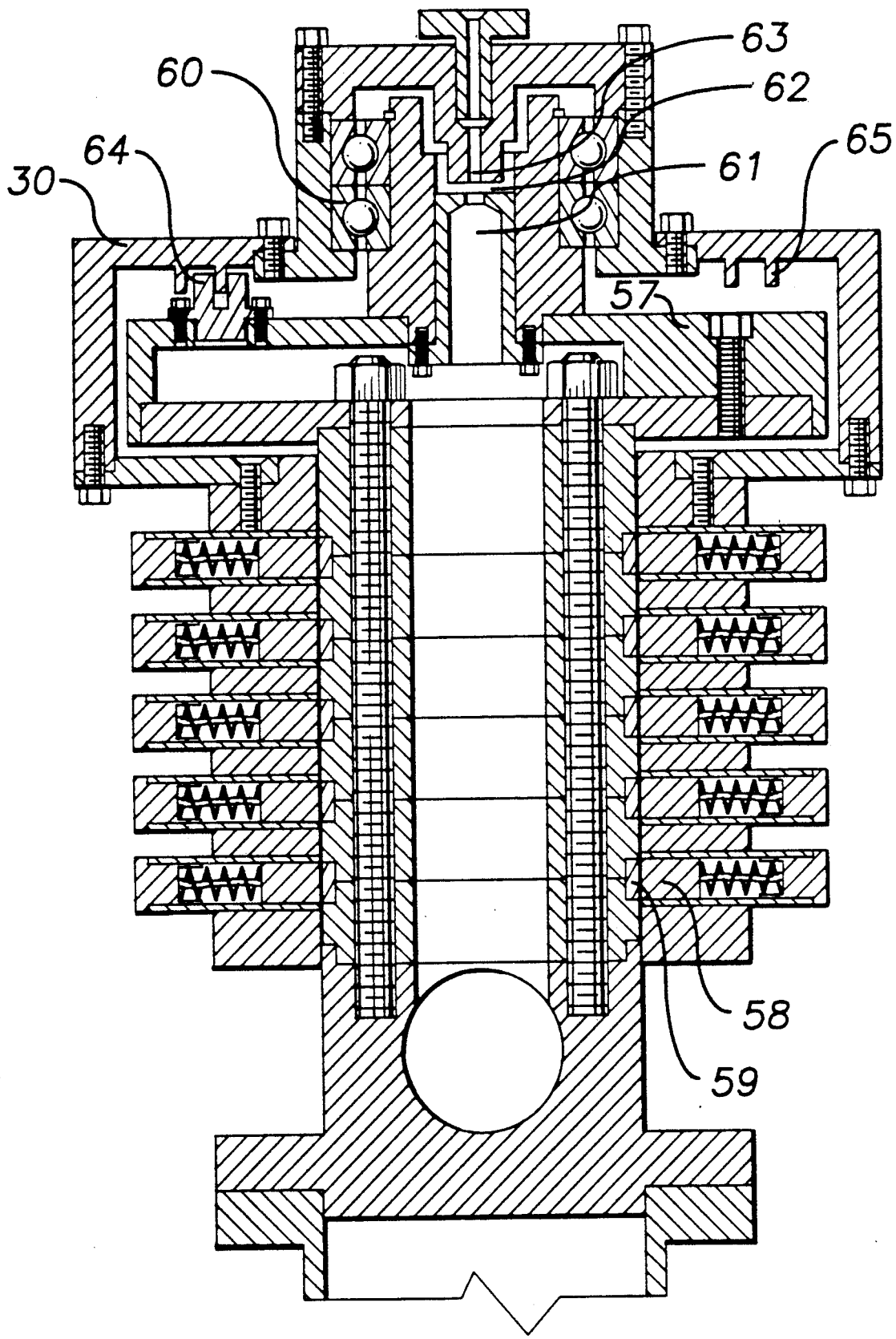
FIG. 8 is a cross section of the top section of the inspection rotor showing the electrical connections and provision for the fibre optic link of the preferred embodiment.

Item 30 is further detailed in FIG. 8. It performs two functions. First, it has a slip ring arrangement for bringing electical power to the rotating electronics. Second, it provides a fibre optic link for data to move between the rotating and stationary parts of the system (see the explanation of FIG. 8). The torque arm 31 prevents item 30 from acquiring the rotation of the inspection rotor.

One further detail of FIG. 3 should be mentioned. Cans being moved from/to the conveyor, by the starwheels, will slide over skid plate 32 on their way to/-from the inspection platforms.

Figure 4:
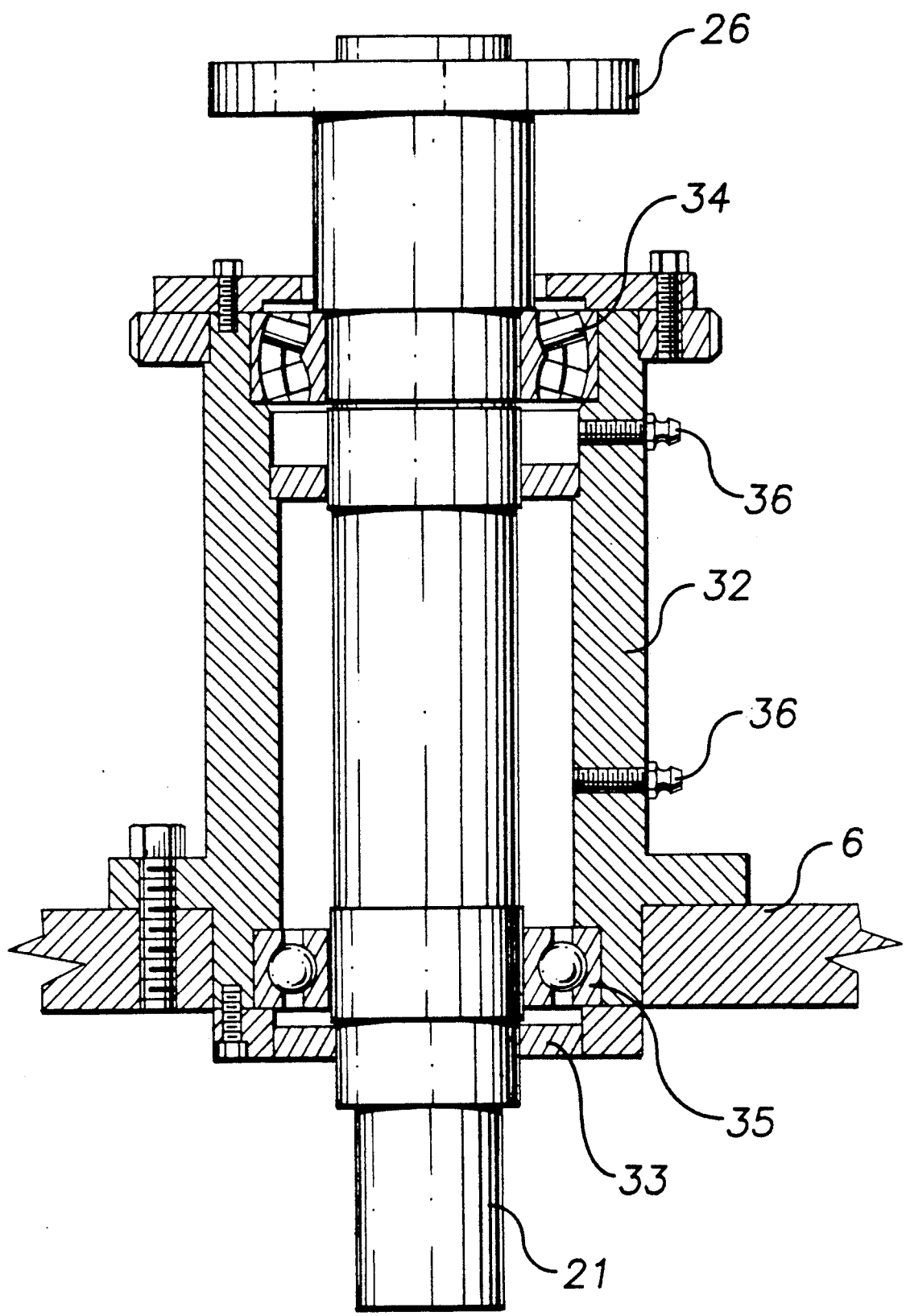
FIG. 4 shows in more detail a cross section of the lower portion of the inspection rotor.

FIG. 4 shows some detail of the inspection rotor shaft 21. The rotor shaft housing (32) is suported by baseplate (6). Self-centering bearings (34) and bearings (35) allow for rotation of the shaft. Provision (36) is made for lubrication the appropriate areas. Items 33 are seals. Gear 26 is the sun gear of FIG. 3 which provides the counter-rotation of the inspection platforms (4). Drive gear 14 of FIG. 2 mounts to shaft 21.

Figure 5:
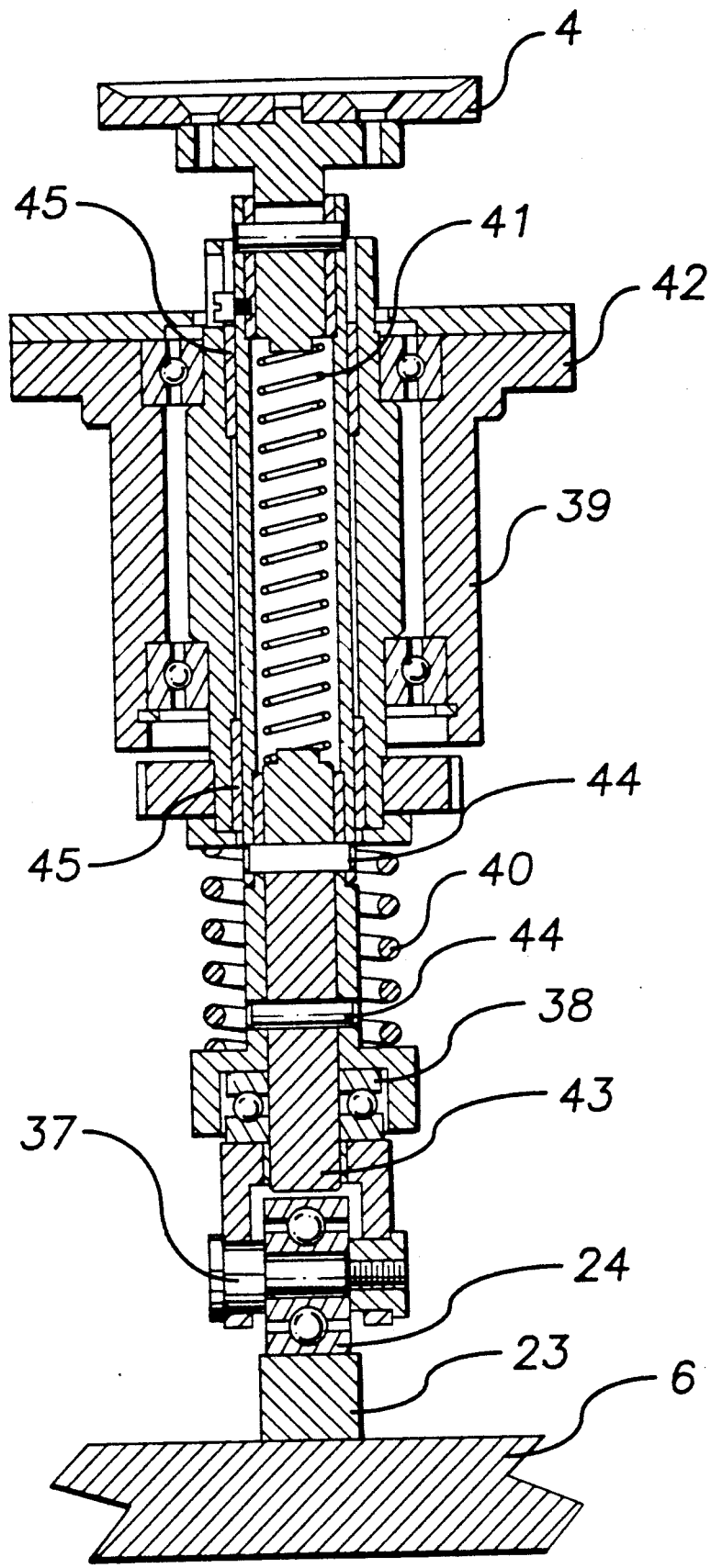
FIG. 5 shows in more detail a cross section of a typical can platform of the preferred embodiment.

FIG. 5 shows some detail of the support mechanism for the can platforms (4). A rotating cam follower (24)

moves along the cam surface (23) which is mounted to the baseplate (6). The cam surface is shaped so that the roller (24), shaft (43), and hence platform (4) is in a low position between the output starwheel (3b) and the input starwheel (3a). As the can platform (4) is moving past the input starwheel (3a) a can, if available, is deposited on the platform, and the platform and can are raised by the cam mechanism so that the top double seam of the can is pushed against the seam rollers (28, FIG. 3; 70, FIG. 9) attached to the optics modules. The can platform and can are lowered as the output starwheel is reached.

The large spring (40) serves to keep the cam follower (24) pressed against the cam (23). Upward movement of gear 27, housing 39, and bracket 42 is prevented because bracket 42 is attached to plate 20 of FIG. 3. The light spring (41) allows the natural variation in nominally identical cans to be compensated for so that each can is securely, but not harshly, pressed against the seam rollers (28,70). (The upward movement of shaft 43 compresses spring 41 to seat the can.)

The movement of the mechanisms of FIG. 5 is complex. First, the whole unit revolves with the inspection rotor in a clockwise direction about shaft 21 (see FIG. 3, FIG. 1). Second, due to the underlying cam, the thrust bearings (38), shaft (43), springs (40 and 41), and inspection platform (4) move up and down at regular intervals. Third, the planetary gear (27) provides for the counter clockwise rotation of the can platform (4) about its own center. Bushings (45) permit this motion.

Figure 6:
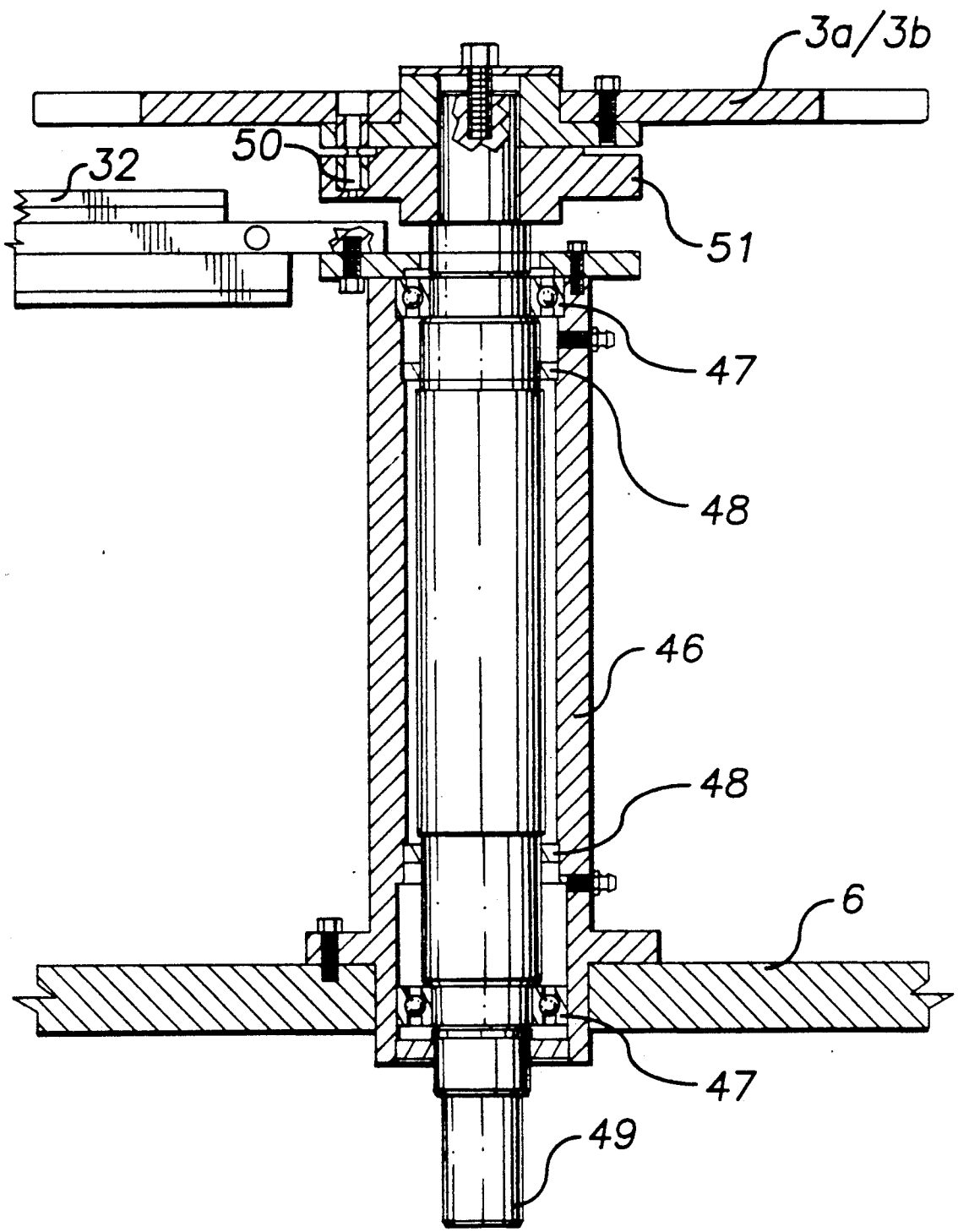
FIG. 6 shows in more detail a cross section of a starwheel of the preferred embodiment.

FIG. 6 shows some detail of one of the two starwheel assemblies. The housing (46]is mounted to the baseplate (6) and has thrust bearings (47) and seals (48) to allow the starwheel drive shaft (49) to rotate. Gears 15a or 15b attach to the lower end of the shaft (49). The starwheel (3a or 3b) is mounted to the starwheel hub (51) using a shear pin (50) to prevent damage should a misfeed occur. Also shown in FIG. 6 is part of the previously mentioned skidplate (32) which allows a can to be transferred to/from starwheel/can platform.

The cross section shown in FIG. 7 provides more detail of the drive mechanism for the worm. Gear 16 which is supported beneath the baseplate (6) by the support (10) is driven by gear 15a. The chain 19 tranmits the power to gear 17 mounted to shaft 52. The idler gear 18 provides chain tension. Bevel gears (53) at the top of the shaft (52) tranfer the torque to the worm shaft (56). Various bearing (54) allow easy rotation.

FIG. 8 shows some inner details of item 30 of FIG. 3. The central section (57) rotates as part of the inspection rotor. The outer section (30) is stationary. Sliding contact is made between the brushes (58) mounted in the stationary section, and the copper slip rings (59) mounted on the rotating central shaft (an extension to shaft 21). Electrical power can thus be brought to the electronic components mounted on the rotating sections of the machine. The outer section (30) is prevented from rotating by a torque arm (31) not shown in FIG. 8 but found in FIG. 3. Bearings (60) allow free relative movement of the two sections.

Many electronic signals are generated by the electronics located on the rotating components of the machine. An infrared transmitter is located in cavity (60) on the center line of rotation. Across the small air gap (62), in the stationary section of FIG. 8, is located the end of a fiber optic cable (63). Signals transmitted across the gap are processed by circuitry located in the stationary frame.

One further feature shown in FIG. 8 is the optical switch (64) which is one of four mounted on the rotating section. The switch is activated every revolution by the protusions (65) of the stationary section. A signal relating to frequency of revolution is thus available. Rotor position can also be determined.

Figure 10:
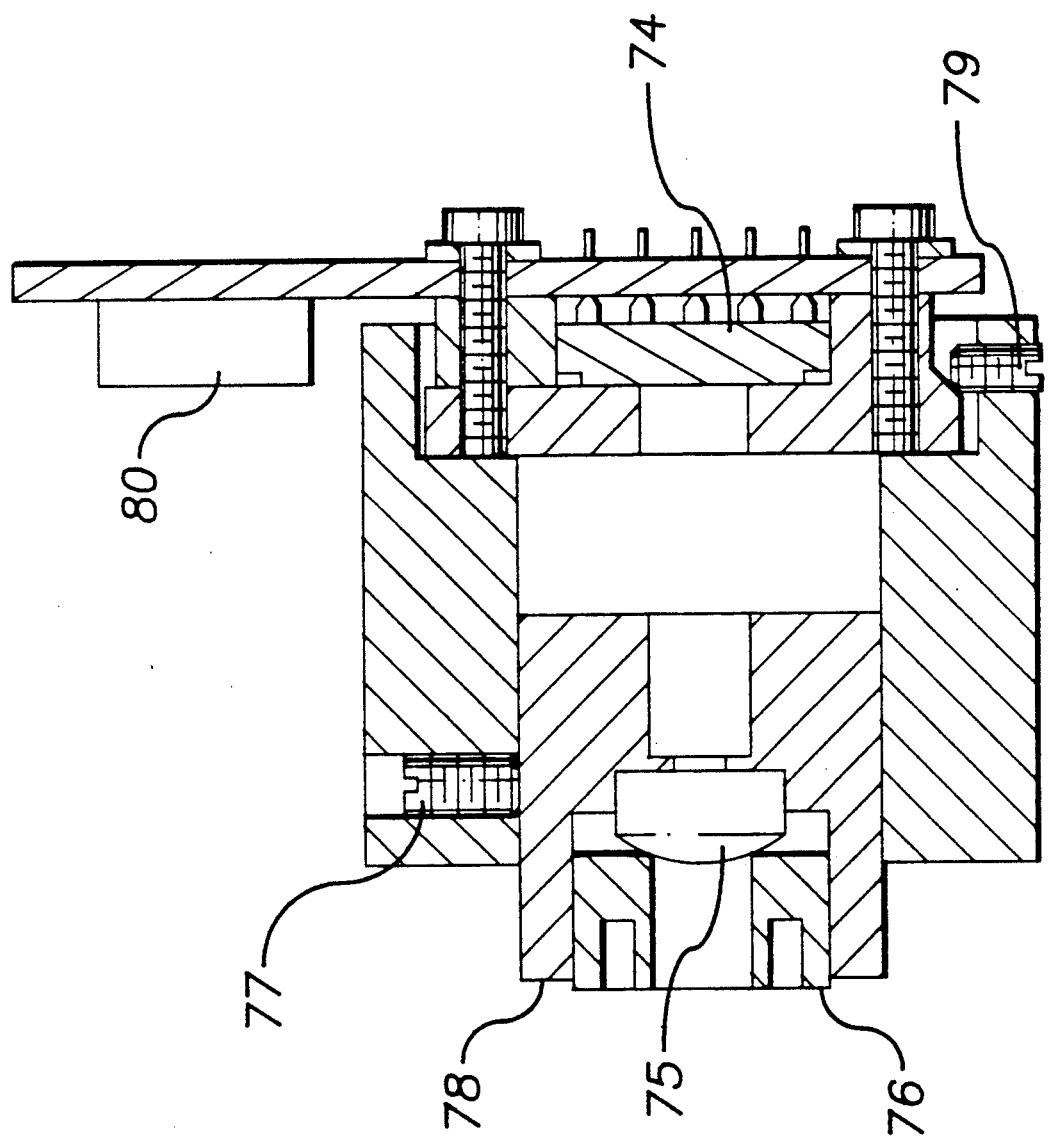
FIG. 10 is a cross section of one of 4 cameras found in the optic module of FIG. 9.
Figure 11:
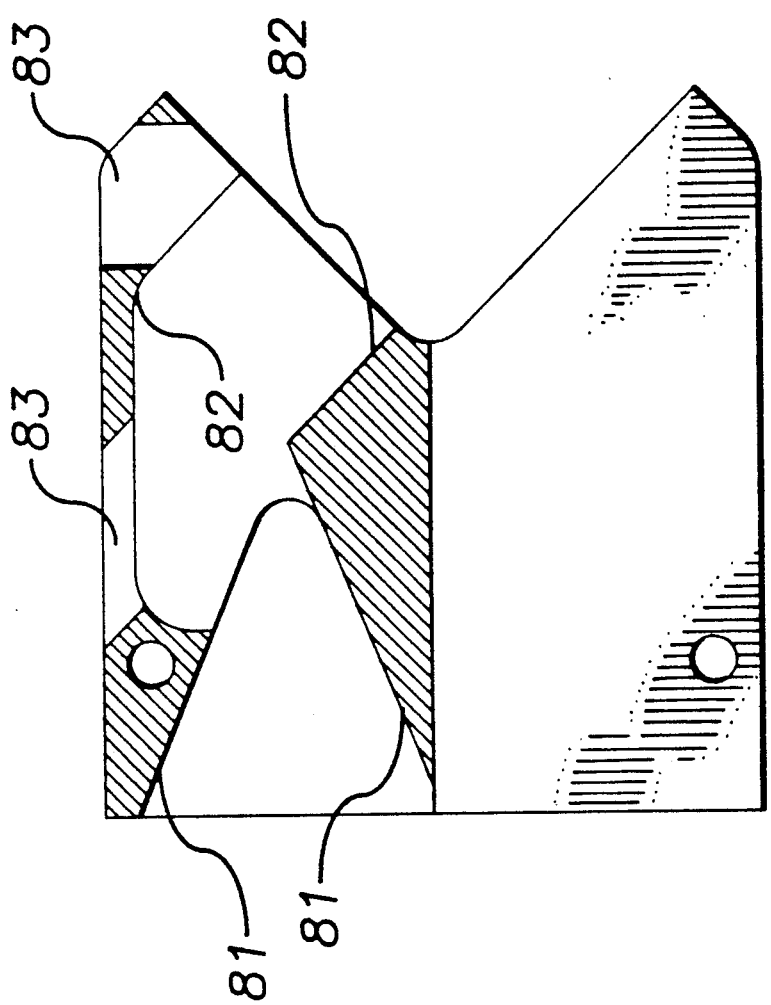
FIG. 11 shows a half section of the light cavity of FIG. 9.

FIGS. 9, 10, and 11 give details of the optics modules (22). Each of the four optics modules of the preferred embodiment has camera systems (67) giving four views of the imaged seam. A light source (66) provides illumination. In the preferred embodiment this light source is a 75 watt quartz-halogen bulb with infrared suppressing coating. Item 69 is a reflecting and diffusing chamber which distributes the light properly and which provides appertures through which the cameras may view the seam.

Each of the camera systems (67) may be moved towards and away from the seam with dowel pins (68) providing a guide. The cross hatched section of FIG. 9 is a cross section of a can guide that serves to correctly position the cans. In planview the guide would be essentially circular. It has an upturned circumferential edge (72) to help guide cans from the input starwheel (3a) to the can platforms (4). A tab (71) at the rear of the guide prevents cans from moving too far in that direction. As previously mentioned, cans on the can platforms (4) are raised against seam rollers and rotated in front of the cameras. One of three such equally spaced seam rollers (70), with its supporting post (73), is shown in FIG. 9 (the other two rollers do not show in the section view). A detail of the seam rollers is of importance. A small grove is provided in the surface of each roller. They are positioned so that the can seam is located in the groves during inspection. Unwanted can movement is therby prevented.

FIG. 10 is a close up of an individual camera. The imaging element is the CCD (charge coupled device)(74). An appropriate lens (75) is retained by ring (76) in mount (78). This mount may be moved towards and away from the CCD to provide proper focus, and locked in position by a set screw (77). A group of three set screws (79), only one of which shows in FIG. 10, is distributed around the CCD. These may me adjusted so that the seam image falls on the centerline of the CCD. The box (80) represents the circuits that are required to drive the cameras and which should be located close to the cameras.

FIG. 11 is a half section of a light chamber (69). Walls (81) are highly reflective, while walls (82) are diffusive. Two appertures (83) through which light can be reflected from the seam to the camera are visible.

FIG. 30 shows a representation of the curvate surface cross section of a can double seam and the four angles from which the seam is viewed by the CCDs. As can be seen, all or substantially all of the curvate cross section length of the seam falls within the combined field of view of the CCDs. FIG. 30 also shows typical output from the CCDs in each of the four views. More will be said about this diagram when discussing signal processing.

While the four views shown are preferred in-order to reliably detect flaws occurring anywhere on the seam, alternative arrangements for obtaining the seam image are certainly possible. In particular, still using the same CCDs and lens arrangements, fibre optic bundles could be used for structured lighting of the seam. Or, fibre optic bundles could direct reflected light to the four CCDs, bypassing the lens/mirror arrangements. Or, the reflected light could be directed to a single CCD and subsequent processing could divide the CCD output into four parts to mimic what is accomplished here. Each has advantages/disadvantages. The disadvantage of using fibre optic bundles is that the physical size of the presently available fibres and the size/shape of the seam preclude using a sufficient number of fibres to get the resolution that is desired. The largest disadvantage of directing images to one large CCD is that the output of the CCD is clocked out serially, so to achieve the same overall machine speed the circuits would have to be driven four times as fast.

In any event, obtaining images of the full seam is desirable for two reasons:

(1) a fault could occur anywhere on the seam and a view from a single angle would not necessarily capture it;

(2) testing has revealed that a fault commonly has an effect in more than one region of the seam—the relationship between the faults observed in different views allows the type of fault (and probable cause) to be classified.

To clarify, the following should be said. It is possible that the metal of the double seam contains a pin hole type of fault or perhaps a small dent. Detecting such perforation or dents would be like detecting faults which occur in bottles on bottling lines or sheet metal on rolling lines and which can be detected by any number of mechanisms disclosed in the literature. A well defined defect such as this produces variations in reflected (or transmitted) light which is easy to monitor if the cameras used are arranged to look at the areas of interest.

On the other hand there is another class of inspection problems, such as the can double seam, where such localization is not the norm. Most faults that occur in double seams are not a result of material imperfections but, rather, a result of an improper joining of the two good pieces of metal. For example, a double seam may be unacceptable because the seam rollers in the canning machine exerted too much pressure when forming the seam. The seam could appear fine in the sense that no pits, gouges, dents or other blemishes are present. Nonetheless, the overly high stress in the metal may lead to later failure. This sort of problem is detected in the present invention by noting that the seam dimensions, in certain views of the seam, will be abnormal. Given the manner in which the double seam is constructed there will commonly be a causal relation between the structure of the seam as viewed from one angle and the same area of the seam viewed from another (that is, the same location around the circumference of the can but in view 4 (say) as opposed to view 3 (say) of the double seam). The problem is to find the correct way to characterize the seam structure so that a machine can determine not only that the structure is out of normal bounds (i.e. a defect is present) but also how it is out of bounds (i.e. characterize/classify the defect).

As is disclosed herein, detection and classification of defects of the double seam can be carried out by measuring the length of the seam in each of the four views and performing appropriate signal processing.

It should be noted that although the present embodiment employs four views of the double seam, the same approach would work if a greater number of views were obtained and possibly if fewer were used (as long as the full length of the seam were scanned).

FIG. 12 gives a block diagram of the preferred embodiment of the electronic aspects of the present invention.

Figure 13:
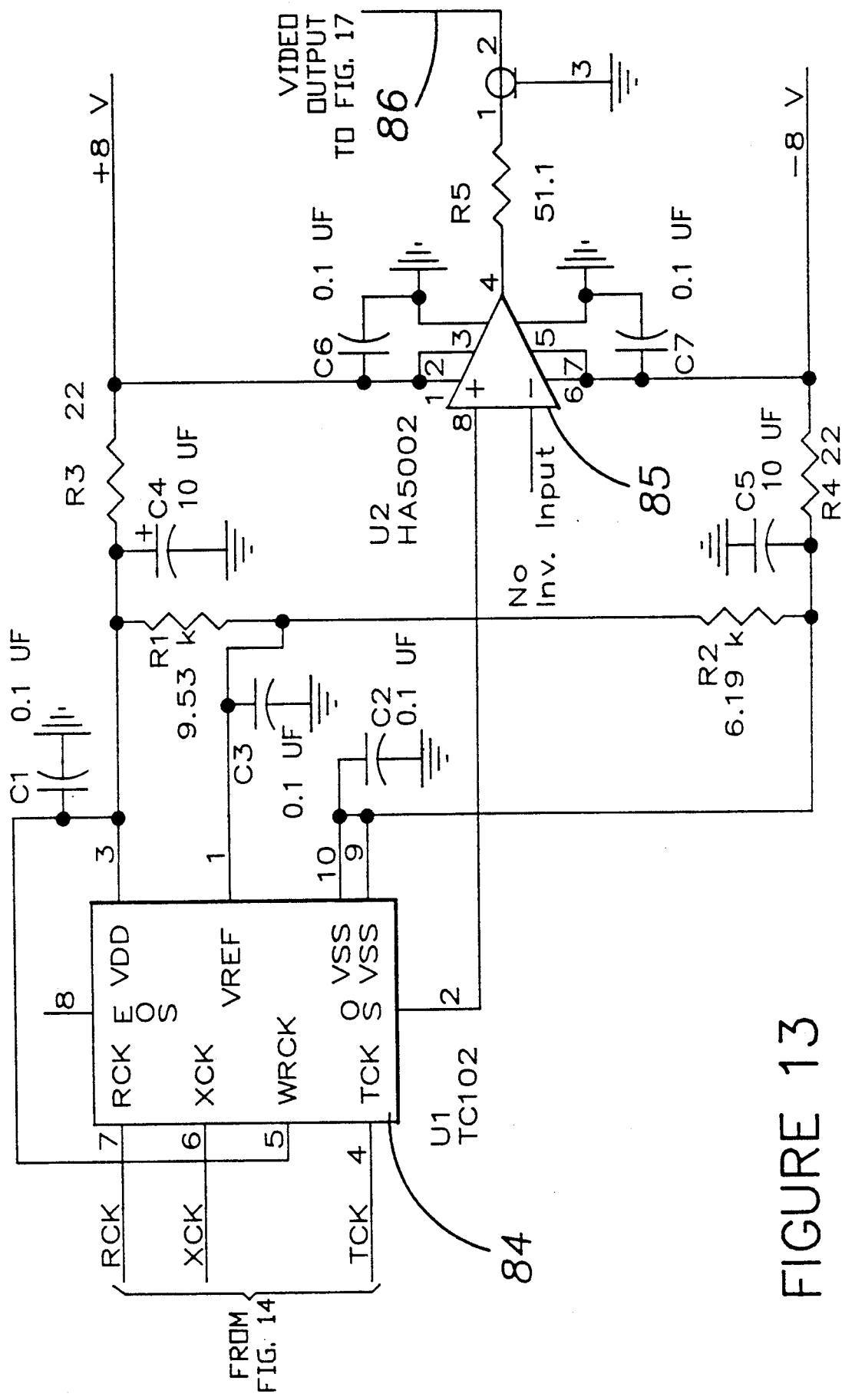
FIG. 13 shows in more detail part of the Signal Prodcution Means of FIG. 12; a CCD and associated output buffer.

The signal production means (12.1) is further detailed in FIGS. 13 to 16. Linear CCDs are used to image the seam of interest. Clock signals appropriate to drive the CCDs of FIG. 13 are provided by circuits of FIGS. 14, 15, and 16.

Information regarding the double seam is coded in the CCD signals. The circuits which extract the appropriate information and which make decisions regarding seam quality are found within blocks 12.4 and 12.5. In the present machine such circuits are located in a reference frame that is stationary, while the optical system and blocks 12.1 and 12.2 rotate. Although more of the circuitry presently depicted to the right of the link in FIG. 12 could be located on board the rotating platform, it was desirable to have such circuits on the stationary frame to simplify troubleshooting during development of the system. It would be possible, in fact, to locate substantially all of the electronics on the rotating sections and still eject faulty product. However, if real time monitoring of events is desired (for example, to help keep machinery in adjustment so defects are prevented) some signals would still have to be sent to the stationary frame.

In the present embodiment, Signal Conditioning Means 1 is needed to prepare the signals for transmission over an optical link, and Signal Conditioning Means 2 is needed to prepare the received signal for subsequent feature extraction on the receiving side of the link.

If the can handling were sufficiently modified (i.e. cans were rotated at a fixed position in front of stationary cameras) the rotating link, and thus Signal Conditioning Means 1 and 2, would be avoided. However, due to the high speed of modern processing lines it was considered more difficult to bring each can to temporary rest in front of a camera. The optical link could also be avoided in a machine designed for the inspection of other sorts of seams or objects. A flat object with a seam running its length should obviously not be rotated with respect to the camera system.

Signal Conditioning Means 2 receives a high speed serial digital signal over the fibre optic link and supplies demultiplexed signals to circuitry of 12.4. Further details are found in FIGS. 23 and 24. The features extracted by 12.4 are seam lengths and seam start/stop positions. The values of these items are passed to the Digital Processing Means of 12.5 for decision making regarding seam quality.

The Ejection and Statistical Means 12.6 is rendered in an AT compatible computer. If digital processing means 12.5 finds a can to be defective, it sends a signal to the computer (with which it share a bus) which will, at the appropriate time, cause the eject mechanism (5)to remove the can from the processing line. An AT compatible computer has sufficient capability for overall monitoring of machine status but at the same time is relatively inexpensive and well understood. Statistics may be kept regarding items such as eject rates and average seam dimensions and this information is readily transferred from the AT via commercially available networks.

In the detailed description that follows reference may be made to local and remote circuits. The four optics modules (22, FIG. 3) found in the preferred embodiment are equally spaced around the inspection rotor.

They are considered to form two pairs of optics modules, where the two members of a pair are at opposite ends of a rotor diameter. The circuitry required to perform the signal processing for one pair of modules is essentially duplicated by circuitry required to process the signals for the other pair. However, some signal processing is not duplicated. For instance, there is only one TAXI chip (FIG. 19e) to handle the signals from all four modules. Physically, these unique components (such as the TAXI chip) are located on the PCB boards that process data from one of the optical module pairs. That pair of modules, the associated circuitry, and the PCB boards are deemed to be 'local'. The other pair, and their circuits and boards are called 'remote' (since they send signals to the unique circuits located on the local boards). The two modules forming a pair are further specified as module (or head) A, and module (or head) B.

FIG. 13 shows one of the sixteen Charge Coupled Devices (84) used in the machine (four optics modules×4 CCDs per module). The CCDs used are the TC102 manufactured by Texas Instruments with 128 pixels in a linear array.

Associated with each is a Harris Semiconductor HA5002 buffer (85) which protects the CCD and drives the CCD output over relatively long coaxial cable (86) to the analog circuits of FIG. 17.

The clock signals (RCLK, XCLK, TCLK) arrive via the driver circuits of FIG. 14. WRCK is not used in this implementation.

The clock signals XCLK, TCLK, and RCLK which are used to coordinate data read in the CCDs (84) are produced by the CCD controller circuits of FIG. 16 and passed to the CCDs via the circuits of FIGS. 15 and 14.

The CCD controller (87, FIG. 16a) is an EPLD (Erasable Programmable Logic Device) manufactured by Altera and called by them the EPf900DC. Listing 1 provides the information necessary to duplicate the EPLD structure used here. From an original clock signal (CLOCK) produced by FIG. 20, this chip produces X, T, & R CLK signals with the correct shape and timing for reading data from a CCD (84). These signals are then operated on by the rotating latches (88) of FIG. 15 to provide the properly timed signals for reading all four CCDs of a given optical module (22).

EPLD 87 also generates the low frequency clock pulses START and STOP which are used by the data encoder (89) of FIG. 18b.

FIG. 14 shows the final circuits required to make the various clock signals output from FIG. 15 suitable for driving the CCDs. Two functions are performed—level shifting and driving of the high impedence clock inputs. One such circuit is needed for each CCD.

Returning to FIG. 16, the EPLD (87), in conjunction with latch 91, generates the 4 strobe signals (STRB1, . . . , STRB4) which are provided (for FIG. 17) to maintain the video signals on a constant DC level corresponding to the level of the black level pulses.

A further feature revealed in FIG. 16 is the clock signal (ADC CLOCK) used by the Analog to Digital converter of FIG. 18. It is provided by a digital delay device from Dallas Semiconductor (93) (item DS1000). Through jumpers, adjustments can be made for various signal propagation times that characterize nominally identical machines. It is used to control the analog to digital converter (90), data encoder (89) and some latches of FIG. 18. It is desirable that the timing signals be such that the CCD output arrives at the ADC during the low phase of the clock. This insures that the ADC sees the input data when it is stable and allows the use of a cheaper ADC than would otherwise be the case.

Another digital delay device (92) provides the FFWR signal for the fifos (194) of FIG. 19a pins labelled _WR).

Finally, two signals CLKA and CLKB are provided by the buffers 94. These are the CLK inputs for the latches (88) of FIG. 15. A and B signify signals for the local and remote heads respectively.

The CLK signal of FIG. 15, and the ADC CLOCK signal of FIG. 16 are derived from the system clock signal (CLOCK) of FIG. 20. The voltage controlled oscillator (95) provides a clock signal dependant upon the voltage supplied to the device (some wave shaping is applied to the output signal). The voltage supplied is determined by the digital to analog converter (96) which has inputs supplied by the PROM (97). The relationship between machine speed and proper clock rate is non-linear and the PROM is used to contain the required mapping, which can be found in Listing 2 (the PROM is a 2716, 4K in size). Inputs to the PROM are via the latch (98). The digital values supplied to the latch, and PROM, may originate in one of two ways.

First, in normal operation, the EPLD (99) (see listing 3) will supply the values. It has its own clock (100) and an input (SPEED) from the optical switch (64) of FIG. 8 which counts revolutions of the machine rotor. In this way, the value of CLOCK is related t the operating speed of the machine.

The alternative method of supplying values to the PROM (97) is via the DIP switches (101). By setting the overide swithces (101a) the EPLD (99) will not provide data and the values given to the PROM will be determined by the DIP swithces (101).

The reason for having the two sources of input to the PROM is as follows: The EPLD (99) provides values that depend upon actual machine speed. When the machine rotor is stationary no value is output and the system clock does not operate. However, for trouble shooting purposes it may be desirable to insert a can into the stationary machine and examine the data that would be gathered if the clock were operational. The DIP switches allow this to be done. Of course, if the machine, in operation, is used at only one speed the flexibility provided by the EPLD (99) is not required.

One further feature of FIG. 20 should be mentioned. The NEWCAN signal allows the latch 98 to release its data only when a can is actually in front of the cameras.

FIG. 21 shows the origin of this NEWCAN signal. In FIG. 21, the CCD DATA is the digital data from the view 2 camera (see FIG. 30). It is compared (102) to a preset threshold value to determine the presence of a can (a can in place produces more reflection than the empty space). The EPLD (103) (see listing 4) provides the NEWCAN signal to FIG. 20a and the CANIN (and AORB) signals to FIG. 19. The AORB signal codes whether the data comes from the local or remote inspection heads.

Return now to FIG. 17. The circuit shown can be divided into two parts. The initial analog part is duplicated 7 more times to handle the 8 cameras that may be in use at any one time. The input signal VID1 is the output from one of the CCDs. Each of the 8 channels inverts and amplifies the video signals coming from a CCD. Each channel also has two other inputs. Gain control (AGC1) is provided via the circuit shown in FIG. 22. Black level restoration is provided via the STROBE1 signal originating in FIG. 16.

The second part of the circuit shows the 8 filters and the analog multiplexor (104) that is used to multiplex signals from the 8 channels. The output analog video signal is amplified on its way to FIG. 18.

FIG. 18 shows the multiplexed video signal of FIG. 17 being amplified (105) before passing to an analog to digital converter (90). The ADC CLOCK controlling the converter, and following latch, comes from FIG. 16 and ultimately from the system clock of FIG. 20.

EPLD (89) is a data encoder which serves to add start and stop bytes to the data train. Listing 5 provides the code for this EPLD (89). The START and STOP pulses controlling this device are generated by EPLD (87) of FIG. 16a.

The data encoder reserves values '00' and 'FF' for control bytes. Input data that has the value '00' is given the value '02'. Similarly, input data 'FF' is set to 'FE'. The EPLD will set the output data to 'FF' only when the STRT input is high.

The original CCD output has now been multiplexed and converted to an 8 bit wide digital stream. FIG. 19 shows the final preparation before delivery to the fibre optic link.

The principal components of FIG. 19 are the TAXI chip (106)) and the EPLD (107) which controls it. The TAXI is an AM7968 produced by Advanced Micro Devices. As input it receives the 8 bit parallel data from latch (108); as output it produces a serial stream for the line transmitter (108b). Output from this ECL device is sent to the infrared transmitter located in cavity (61) of FIG. 8.

Input to the latch (108) comes from one of four sources. As previously mentioned, the four inspection heads of the machine are divided into two pairs. Due to the machine geometry, only one inspection head of each pair may be examining a can at any given time. Data from either of the 'local' heads arrives through one of the FIFOs (194); data from the 'remote' heads through the other FIFO (194).

The latches (109) provide the other two sources of input: diagnostic signals form either the remote of local boards. A full byte is available for such diagnostics but in the present embodiment only two bits are used—AORB and CANIN. The AORB switch indicates for each pair of optical heads (local & remote) which optical head is providing data. The CANIN bit indicates whether or not a can is actually in front of the cameras. Both signals are provided by EPLD (103) of FIG. 21.

The EPLD (107) has to determine which of the 2 fifos or which of the 2 latches to enable. The enabled device gets to clock its contents into the TAXI (106). The enabling is done according to a fixed sequence. The cycle for the EPLD is (1) put out command bits (COM00 to COM03) (2) read the diagnostic latches (3) read the fifos. The NEWCAN signal (NEWCAN 0 for local heads, NEWCAN 1 for remote heads) is used to begin the cycle. This signal comes from FIG. 21.

The TAXI (106) will send commands if either C0, C1, or C2 is active. The TAXI receiver EPLD (115) will detect the command sequences in the data stream and react appropriately.

One further circuit before the fibre optic link is of importance. FIG. 22 shows the gain control circuits for one pair of optic modules. The output signals are used by the analog circuits of FIG. 17a. Potentiometers (110) may be manually adjusted to vary the DC voltage levels. In future the potentimeters will be replaced with circuits to provide automatic adjustment of the gain.

This completes the discussion of the Signal Production Means and Signal Conditioning Means 1 of FIG. 12. The image data is now in the form of a multiplexed high speed digital serial stream. Details of the infrared transmitter and receiver that form the optical link are not shown but are of standard design.

FIG. 23 provides for the high speed serial data which has been transmitted over the link, to be converted back to a parallel form. Item 111 is a MECL receiver (MC10116) and 112 is the TAXI receiver (AM7969) which actually produces the parallel data from the input serial stream.

There are two pairs of latches to which the data may be directed under the control of EPLD 115 (see listing 7). Latches 113 receive the diagnostic data for the local and remote cameras. Latches 114 receive the image data for local and remote cameras.

When data bits are on D0–D7, then DSTRB tells EPLD (115) to clock the data. Similarly, when command bits are on D0–D7 then CSTRB causes the command data to be clocked.

FIG. 24 performs two functions. First, it demultiplexes the data coming from FIG. 23. The demultiplexer (116) monitors the data stream. The data encoder 89 of FIG. 18b reserves 'FF's for marking the beginning of scan lines and '00's to mark the end. Upon detection of an 'FF' in the data the demultiplexing cycle begins. Data is encoded in the order view 1, view 2, view 3, view 4. More precisely the data is in the order: pixel 1 of view 1, pixel 1 of view 2, . . . , pixel 1 of view 4, pixel 2 of view 1, . . . , pixel 2 of view 4, . . . , pixel 128 of view 4. The data is read into the four latches (117) under control of the demultiplexer (116), with all data for a given view going to a particular latch.

The counter (118) is used to count the number of pixels passed to the latches (117). The comparator (119) and associated DIP switches are provided to control the number of pixels passed to the latches. The normal setting is 128.

The second function of the FIG. 24 is to provide the delay clock that is used to produce the delayed signal (FIG. 25) that is subsequently used by the edge detection circuits of FIG. 26.

FIG. 25 shows the simple circuitry which takes data from one of the ouput latches (117) (i.e. the data for one view) of FIG. 24d and provides two signals to the following analog circuitry of FIG. 26.

The arriving data is passed through a direct register 121 and also the delay providing registers 122. The delay registers used can handle only four bits so a pair of them is needed.

The delay registers 123 produce a delayed signal which could be used by subsequent analog circuits for the extraction of curvature information from the data. In the present embodiment, such information is not used in the decision about seam quality. It is anticipated that a future version of the machine will make use of such data.

The required clock signals are provided by EPLD 116 of FIG. 24a. In particular PIXCLK determines how much delay to provide.

The direct and delayed signals from a given camera (ie one view) are each passed through digital to analog converters 124 of FIG. 26. The two signals are 8 bits wide and of identical shape and amplitude. They differ only in phase.

Each analog signal is acted on by a low pass filter 125, and amplifier 126. This latter item also acts as a 'super diode', cutting off any negative parts of the signal. A voltage follower 127 acts on the delayed signal only.

The differential amplifier 128 subtracts the two signals. The signal appearing on this amplifiers output contains both positive and negative parts which correspond to rising and falling edges in the original video signal. The comparators 129 and 130 produce standard logic pulses from the amplifier output. Potentiometers 131 allow the thresholds for the comparators to be adjusted.

As is indicated by the dotted boxes of FIG. 26, the circuits for producing the COMPB pulse for views 2 and 4 differ slightly from those used with views 1 and 3. The reason for detecting rising and falling edges in two views but only rising edges in the other two wi 1 be made clear in the later discussion of FIG. 30.

One further feature of FIG. 26 should be mentioned. The two video signals are kept on a common DC level, corresponding to a minimal value of the non-delayed signal, by 132 acting (in a peak detector configuration) in conjunction with amplifiers 133.

FIG. 27 shows an EPLD (134) and a set of latches which together provide data to subsequent digital processing circuits. The COMPA and COMPB signals from the preceeding analog edge detection circuits are inputs to the EPLD. The function of the EPLD is to determine the start and stop locations of the seam edges (ie at which pixel, of the 128, the seam begins and ends), and to determine the length of the seam, at each scan position.

The start positions are latched out through 135 to FIG. 28. Similarly stop positions are passed through latches 136 and the lengths through 137. Latches 138 anticipate future development when curvature information will be used in the decision making. In the present embodiment the length (length of the seam in pixels) is the critical component of the digital processing scheme.

Listings 9a–9d provide the information required to program the four different EPLDs required for the four different views. Since the data from each view has a different characteristic shape (see FIG. 30) different devices are required to detect the correct rising/falling edges.

Consider at this time FIG. 30. It shows the outline of a double seam. It also shows typical CCD output for each of the four views of the present embodiment. The analog edge detection circuits of FIG. 26 produce pulses with each significant rise and fall of CCD output, but seam lengths can be extracted from the data only if the correct edges are dealt with. It is quickly apparent why there were two variations of the analog circuits in FIG. 20. In view 1 a strong rising edge is characteristic of the beginning of the seam and a strong falling edge is characteristic of its end. Similarly with view 3. In view 4, on the other hand, although a strong rising edge marks the start of the seam, it is only the rising edge that results from reflection off the bottom of the countersink that can be readily detected. The length in view 2 is similarly marked by two rising edges. The long slow decline in light levels as we pass down the seam is quite unsuitable for reliably triggering circuits. There is, fortunately, a small but significant increase in light level as we pass to the flat surface of the can body.

The digital controller of FIG. 27 (EPLD 134) is programmed to 'close its eyes' to edges in certain areas. Consider view 3 of FIG. 30 and assume that the risign egde characteristic of the outside edge of the seam has been detected. Since the seam has a characteristic width, the falling and rising pulses that mark the top of the seam can be ignored. The controller will only start looking for a falling edge when it is dealing with pixels that are safely passed the region marking the seam top.

In any event, each view has its own characteristics and it is only experience with a particular type of can that will reliable determine what sorts of thresholds to use.

FIG. 28 shows the interface between the output of FIG. 27 and a commercially available digital processing board which operates upon that output. This interface is essentially a dual port RAM with two banks of memory.

Data from FIG. 27 arrives via the 8 bit data bus and is temporarily stored in one of two 64K memory sections (139+140 or 141+142). The incoming data is the series of start and stop positions and lengths for each of the approximate 2000 scan locations, for each of the four views, for each can. The structure of the data is: starting pixel of scan line n, stop pixel for scan line n, length of scan line n, no signal (or curvature), starting pixel for scan line n+1, . . .

The memory bank to which the data is directed is controlled by the ABSEL signal from the controller chip 144 of FIG. 29a. This same EPLD also determines the addresses in which the data will be temporarilly placed. Lines C12–C15 (of EPLD 144) select the most significant bits for the address and the counter 145, running at 1/16 the rate, determines the least significant bits.

The essential operation of FIG. 28 is as follows: incoming data is sent to a given memory bank such that view 1 and view 2 data are placed in RAM 140 and view 3 and view 4 data is placed in RAM 139. Within the view 1 data, the 2000 or so start positions are contin-guous. Similarly the 2000 or so end positions and 2000 or so lengths are stored together. Similarly for each of the other views.

When data from the next can arrives, as indicated by ABSEL, it is directed to the the other memory bank (141 & 142). Simultaneously, the DSP board may access the data from the previous can (stored in 139 &140) via its own bi-directional bus and port 143. (To perform a memory test the DSP board may write into the dual port RAM via port 144). Because of the contiguous blocks of memory, the DSP can get the information it needs (ie the length values) very rapidly once access is begun.

Listing 10 gives the code used to program EPLD 144.

The output data flow from FIG. 28 is an 8 bit wide stream. For any given can, the starting pixel for each of the approximately 2000 scans is transmitted, then the ending pixel for each scan, and then the length (in pixels) for each scan. Provision is also made for further information curvature) to transmitted. After all the information for view 1 is transferred, views 2, 3, and 4 are handled in turn.

The digital processing board that uses this data is a commercially available unit called the TMS320C25 and available from SPECTRUM Signal Processing Inc. The board has built-in A/D interfaces which are not used in the present project. It plugs into any PC expansion bus. Details regarding the board can be obtained from the vendor.

The function of the board is to analyze the incoming data and determine when seam conditions are abnormal. None of the decision procedures so far implemented on the DSP board uses the absolute start and stop position data. Adequate results have been obtained using only the length of each scan line (which of course depends upon the relative start/stop positions.

A significant amount of processing is done to change this length information into decisions about seam quality. The general procedures of the program coded into the DSP board are outlined below and anyone skilled in the art will be able to duplicate the functions. However, depending on production line speed, it may be noted that assembly language coding may be required.

The process begins when the DSP board receives an interupt signal from the APP to indicate that data is ready.

If the status of the APP indicates that there is no can in the inspection module (CANIN is low)
Then the DSP interrupts the PC to indicate a NO CAN signal, and the DSP enters IDLE mode;
Otherwise (there is a can present), the DSP reads the Number of Scan Lines value from the APP.
If the Number of Scan Lines does not fit within a pre-defined tolerance
Then the DSP interupts the PC with a TOO MANY or TOO FEW scanlines signal;
Otherwise (the number of scan lines is acceptable), the DSP will read in all of the scan lines from all 4 views from the APP.

Once all of the scan lines have been read into memory, there is no further communication between the APP and DSP during that can's analysis.

All of the scan line values are now available in RAM. The initial stage of analysis treats the data from each of the 4 views seperately. The notation s(v,i) indicates the scan line value in view v at position i where v ranges from 1 to 4, and i ranges from 0 to the total number of scan lines for that view it is somewhat larger than 2000 in the present embodiment).

Well localized spikes in the data are considered to be noise and are eliminated using the following procedure:

If $ABS\{s(v,i) - s(v,i+1)\} >$ noise threshold Then
$s(v,i) = \{s(v,i-1) + s(v,i+1)\}/2$ where ABS indicates the absolute value, and the noise threshold is a constant. The value of this constant, and others below, is best determined by experience with particular cans in a praticular machine.

Next, the scan line data from each view is smoothed to eliminate the high frequency component of the signal. The following low pass filter is applied to the data for each view independently.

$sms(v,i) = s(v,i)*(exp(k) - 1) + sms(v,i-1)*exp(k)$ where sms(v,i) indicates the value of the smoothed signal at position i, in view v and where k is a predefined constant. To minimize the time required for calculation, the values of exp(k) are found using a look up table.

A running average for the scan line value, at each scan line position, is now determined. rav{v,i} indicates the value of the running average in view v at scan line i. Then $rav(v,i) = \{SUM[\text{from } i-512 \text{ to } i] \text{ of } sms(v,i)\}/512$ where SUM[from ... to ...] indicates a summation over the specified limits. 512 lines are used to provide the running average because it is of reasonable size and for the particualr DSP board used, division by 512 is a simple register shift to the right. To get the process started a header of 512 scan lines (the last 512 scan lines) is tacked to the front of the list of scan lines.

Our data for each view has now been noise reduced and smoothed and we have a value for the running average of the seam length at each of the inspection locations (in each of the views). We now create a 'defect vector' corresponding to significant variations of the seam lengths from the running average of the lengths.

Consider one view and assume that 2000 images have been captured around the seam circumference. For each of these 2000 locations we have values for the seam length (smoothed) at that location and for the running average at that location. Assume that for the view under consideration a deviation in these two quanities of 10 or more pixels has been found to be significant (i.e. normal scratches and dirt generally produce smaller deviations). Assume that the first location where a significant deviation occurs is at scan line 300. This value is the 'start position' of our first defect. The 'peak value' is set to the deviation of the scan line length from the running average length at this position. The 'end position' has the same value as the 'start position'. As each subsequent line is examined it will be found either to exceed the 10 pixel threshold or not. If the threshold is still exceeded, the end position component of the defect vector is changed to the new scan line position. The peak value component is updated if the latest scan line deviates from the average more than the previous lines did. At some point, let us say at scan line 400, the deviation will drop below the chosen threshold value and the defect vector is complete. In this case, defect vector #1 is the 3-tuple (peak, 300,400) where peak is the maximum deviation of the seam length from the running average of the seam lengths. That is, for the view under consideration, there is a 'defect' extending between scan line 300 and scan line 400 and it has a maximum deviation of 'peak' pixels. This process of creating defect vectors continues until all 2000 scan lines have been processed. The result is a set of zero or more vectors that represent possible defects. More processing is performed before the final decision regarding the existence of defects is made.

The present embodiment is designed such that if the number of defect vectors for any view is greater than 32 then the PC will be interupted and a processing of that can will stop. Such a large number of defect vectors indicates a badly damaged seam; or else there is too much signal noise—in either case processing ceases and the can is ejected by the air powered piston of FIG. 1.

The original defect vectors are now 'merged'. That is, defects that are within a predefined distance of each other are considered as part of one larger defect. In particular, if the difference between the start component of one defect vector and the stop component of the following defect vector is less than a predetermined threshold, then a new vector replaces the two. The peak component of the replacement vector is the larger of the two contributing vectors. The start component of the new vector is the start position of the first vector; the end component of the new vector is the end position of the second vector. This merging of the defect vectors continues until all of the original defect vectors have been considered.

The next stage of processing is to compare the lengths and peaks of the various merged defect vectors to predetermined minimum values. Defect vectors representing short lived variations, or longer lived but not extreme variations, are discarded. These minimum values, along with the various constants already mentioned, are obviously important to the decision making of the machine. The appropriate choice of constants can be made by educated trial and error. The values obviously depend upon the specifics of the machine. They may also vary with the type and size of can being used. Although tedious, experience with a range of defects, in a specific type of can, will provide reasonable values for the various constants.

We are now left with a set of defect vectors, one for each of the four views, which represent significant deviations from perfect seam construction. One further stage of processing occurs with these vectors. An attempt is made to align the defect vectors (and therefore the defects) of one view with those in another. The position of a defect is taken to be the middle of the defect (i.e. the scan line positon of the middle of the defect—scan line 350 using the numbers in the example above). If the position of a defect in view 1 is within a predetermined value of the position of a defect in view 2 then the defect vectors are probably the result of the same real defect. The defect vectors (and defects) are said to align. Similarly, an attempt is made to align defects that are observed in views 3 and 4.

The existence of even unaligned defect vectors may be sufficient cause to eject cans as defective. It may also be noted that the value of the peak component of the vectors can be positive or negative depending upon whether the deviation in seam length from the running average was due to abnormally short or abnormally long seam lengths. This immediately gives us some information about the type of fault that may be present in the can seam.

Consider FIG. 32 which shows cross sections of two different defects. In 32a the view 3 dimension is long as would be the case with cutovers. On the other hand if this dimension were shorter than normal it could indicate too much horizontal pressure was applied during seam formation.

FIG. 32b shows a fractured seam. The length in view 2 has been found to be shorter than normal because the edge detection circuitry has detected the edge at the beginning of the fracture.

However, it should be noted that seam defects normally affect the images in more than one view. One type of fault may produce a long seam length in views 1 and 2 and a short length in view 3. Another type of fault may produce a long vector in view 1 but short vectors in views 2 and 3. The DSP will classify the type of fault when it detects such characteristic combinations. It is difficult to give a mapping, in advance, from defect vector combinations to type of fault. A general procedure can be outlined for determining such mappings.

The DSP board has access to the following seam information: start positions of the seam, stop position of the seam, and length of the seam, for each scanning position, for each of the views. The DSP board resides on the PC bus. Anyone skilled in the appropriate art can use this information to produce graphical displays that are highly useful. For instance, a bar chart of the 2000 or so seam lengths can be displayed. This might be overlayed with defects that are determined from the DSP processing. The defects that are aligned by the DSP might be further highlighted. By examining such displays, especially when the corresponding can is available, it is possible to tune the machine for good performance. Changes made to the various thresholds may be evaluated.

This completes the description of the embodiment of the invention. No mention has been made of the value of the information gathered by the machine other than to say that cans with defective seams will be ejected from the processing line. It will be obvious to those skilled in the arts that having a machine which can accurately determine seam dimensions, at processing line speeds, is of inestimable value for controlling the double seaming process. For instance, as suggested above, computer displays showing average seam dimensions, in each of the views, can be generated from the data available. Such displays can alert plant personel to problems or trends before a serious problem actually arises. Charts showing defect rates over time is another area where the present invention provides far more timely data than any method available untill now.

The Listings 1 through 9 dicussed above are set forth in the following Appendix

Although the embodiment of the invention that has been described relies upon radiation signals within the visible light region, it will be apparent to those skilled in the art that non-visible radiation frequences within the visible light region were the optical characteristics of the CCDs that were readily available and inexpensive.

APPENDIX

LISTING 1

```
RICK SLAMKA
SENTINEL VISION INC.
FEBRUARY 5, 1988
1.00
A
EP900
P2CCD.ADF  TC102 CCD CONTROLLER FOR HEAD CCD CONTROLLER PCB
OPTIONS:TURBO=ON
PART:EP900

INPUTS:CLOCK1@1,
       CLOCK2@21,
       CLOCK3@22,
       ENABLE@2,
       CLEAR@3

OUTPUTS:QA@5,    %QAA% DELAYED BY ONE CLOCK CYCLE FOR ANALOG MUX%
        QB@6,    %QBB% DELAYED BY ONE CLOCK CYCLE FOR ANALOG MUX%
        QAA@30,  %ACTUAL COUNT LSB%
        QBB@31,  %ACTUAL COUNT 2ND LSB%
        Q0@7,
        Q1@8,
        Q2@9,
        Q3@10,
        Q4@11,
        Q5@12,
        Q6@13,
        Q7@14,
        EOC@15,
        !XCK@36,
        !TCK@35,
        !RCK@34,
        BLKLEV@33,
        STOP@28,
        START@27,
        FIFWREN@26,
        FIFWR@25,
        !STOP@29,   %DRIVEN THROUGH AC14 TO REMOTE%
        !START@16   %DRIVEN THROUGH AC14 TO REMOTE%
NETWORK:
        CLOCK1=INP(CLOCK1)
        CLOCK2=INP(CLOCK2)
        CLOCK3=INP(CLOCK3)
        ENABLE=INP(ENABLE)
        CLEAR=INP(CLEAR)

QB=RONF(QBd,CLOCK1,GND,GND,VCC)
        QA=RONF(QAd,CLOCK1,GND,GND,VCC)
        QAA,QAAf=TOTF(QAAt,CLOCK2,CLEAR,GND,VCC)
        QBB,QBBf=TOTF(QBBt,CLOCK2,CLEAR,GND,VCC)
        Q0,Q0f=TOTF(Q0t,CLOCK1,CLEAR,GND,VCC)
        Q1,Q1f=TOTF(Q1t,CLOCK1,CLEAR,GND,VCC)
        Q2,Q2f=TOTF(Q2t,CLOCK1,CLEAR,GND,VCC)
        Q3,Q3f=TOTF(Q3t,CLOCK1,CLEAR,GND,VCC)
```

```
Q4,Q4f=TOTF(Q4t,CLOCK1,CLEAR,GND,VCC)
Q5,Q5f=TOTF(Q5t,CLOCK1,CLEAR,GND,VCC)
Q6,Q6f=TOTF(Q6t,CLOCK1,CLEAR,GND,VCC)
Q7,Q7f=TOTF(Q7t,CLOCK1,CLEAR,GND,VCC)
EOC,EOCf=RORF(EOCd,CLOCK1,CLEAR,GND,VCC)

!XCK=RONF(XCKd,CLOCK2,CLEAR,GND,VCC)
!TCK=RONF(TCKd,CLOCK2,CLEAR,GND,VCC)
!RCK=RONF(RCKd,CLOCK2,CLEAR,GND,VCC)
BLKLEV=RONF(BLKLEVd,CLOCK2,CLEAR,GND,VCC)

STOP=RONF(STOPd,CLOCK2,GND,GND,VCC)
!STOP=RONF(SSTOPd,CLOCK2,GND,GND,VCC)

START=RONF(STARTd,CLOCK2,GND,GND,VCC)
!START=RONF(SSTARTd,CLOCK1,GND,GND,VCC)

FIFWREN,FIFWRENf=TOTF(FIFWRENt,CLOCK2,GND,GND,VCC)
FIFWR=CONF(FIFWRi,VCC)

EQUATIONS:
    QAd=QAAf;
    QBd=QBBf;
    QAAt=(ENABLE*/EOCf)
        +(QAAf*EOCf);
    QBBt=(ENABLE*QAAf*/EOCf)
        +(QBBf*EOCf);
    Q0t=(ENABLE*QAAf*/EOCf*QBBf)
        +(Q0f*EOCf);
    Q1t=(ENABLE*QAAf*/EOCf*QBBf*Q0f)
        +(Q1f*EOCf);
    Q2t=(ENABLE*QAAf*/EOCf*QBBf*Q0f*Q1f)
        +(Q2f*EOCf);
    Q3t=(ENABLE*QAAf*/EOCf*QBBf*Q0f*Q1f*Q2f)
        +(Q3f*EOCf);
    Q4t=(ENABLE*QAAf*/EOCf*QBBf*Q0f*Q1f*Q2f*Q3f)
        +(Q4f*EOCf);
    Q5t=(ENABLE*QAAf*/EOCf*QBBf*Q0f*Q1f*Q2f*Q3f*Q4f)
        +(Q5f*EOCf);
    Q6t=(ENABLE*QAAf*/EOCf*QBBf*Q0f*Q1f*Q2f*Q3f*Q4f*Q5f)
        +(Q6f*EOCf);
    Q7t=(ENABLE*QAAf*/EOCf*QBBf*Q0f*Q1f*Q2f*Q3f*Q4f*Q5f*Q6f)
        +(Q7f*EOCf);

XCKd=/((/Q0f*/Q1f*/Q2f*/Q3f*/Q4f*/Q5f*/Q6f*/Q7f)
    +(/QBBf*Q0f*/Q1f*/Q2f*/Q3f*/Q4f*/Q5f*/Q6f*/Q7f));

TCKd=Q0f;

RCKd=/(/QAAf*/QBBf);

BLKLEVd=( QAAf* QBBf*/Q0f* Q1f*/Q2f* Q3f*/Q4f*/Q5f*/Q6f*/Q7f) %43%
      +( QAAf* QBBf* Q0f* Q1f*/Q2f* Q3f*/Q4f*/Q5f*/Q6f*/Q7f) %47%
      +( QAAf* QBBf*/Q0f*/Q1f* Q2f* Q3f*/Q4f*/Q5f*/Q6f*/Q7f) %51%
      +( QAAf* QBBf* Q0f*/Q1f* Q2f* Q3f*/Q4f*/Q5f*/Q6f*/Q7f);%55%

EOCd=/QAAf* QBBf* Q0f*/Q1f* Q2f* Q3f* Q4f*/Q5f*/Q6f* Q7f;
```

```
STARTd=( QAAf* QBBf* Q0f*/Q1f*/Q2f*/Q3f* Q4f*/Q5f*/Q6f*/Q7f)    {71}
      +(/QAAf*/QBBf*/Q0f* Q1f*/Q2f*/Q3f* Q4f*/Q5f*/Q6f*/Q7f)
      +( QAAf* QBBf*/Q0f* Q1f*/Q2f*/Q3f* Q4f*/Q5f*/Q6f*/Q7f)
      +(/QAAf* QBBf*/Q0f* Q1f*/Q2f*/Q3f* Q4f*/Q5f*/Q6f*/Q7f)
      +( QAAf* QBBf*/Q0f* Q1f*/Q2f*/Q3f* Q4f*/Q5f*/Q6f*/Q7f)
      +(/QAAf*/QBBf*/Q0f* Q1f*/Q2f*/Q3f* Q4f*/Q5f*/Q6f*/Q7f)
      +( QAAf*/QBBf*/Q0f* Q1f*/Q2f*/Q3f* Q4f*/Q5f*/Q6f*/Q7f)    {77}
      +(/QAAf* QBBf* Q0f* Q1f*/Q2f*/Q3f* Q4f*/Q5f*/Q6f*/Q7f);   {78}

SSTARTd=/(( QAAf* QBBf* Q0f*/Q1f*/Q2f*/Q3f* Q4f*/Q5f*/Q6f*/Q7f)    {71}
       +(/QAAf*/QBBf*/Q0f* Q1f*/Q2f*/Q3f* Q4f*/Q5f*/Q6f*/Q7f)
       +( QAAf* QBBf*/Q0f* Q1f*/Q2f*/Q3f* Q4f*/Q5f*/Q6f*/Q7f)
       +(/QAAf* QBBf*/Q0f* Q1f*/Q2f*/Q3f* Q4f*/Q5f*/Q6f*/Q7f)
       +( QAAf* QBBf*/Q0f* Q1f*/Q2f*/Q3f* Q4f*/Q5f*/Q6f*/Q7f)
       +(/QAAf*/QBBf*/Q0f* Q1f*/Q2f*/Q3f* Q4f*/Q5f*/Q6f*/Q7f)
       +( QAAf*/QBBf*/Q0f* Q1f*/Q2f*/Q3f* Q4f*/Q5f*/Q6f*/Q7f)    {77}
       +(/QAAf* QBBf* Q0f* Q1f*/Q2f*/Q3f* Q4f*/Q5f*/Q6f*/Q7f));  {78}

STOPd=( QAAf* QBBf* Q0f*/Q1f* Q2f*/Q3f* Q4f*/Q5f*/Q6f* Q7f);  {599}

SSTOPd=/( QAAf* QBBf* Q0f*/Q1f* Q2f*/Q3f* Q4f*/Q5f*/Q6f* Q7f);  {599}

FIFWRENt=(/QAAf*/QBBf* Q0f* Q1f*/Q2f*/Q3f* Q4f*/Q5f*/Q6f*/Q7f
          */FIFWRENf)                  {76}
       +( QAAf*/QBBf*/Q0f* Q1f* Q2f*/Q3f* Q4f*/Q5f*/Q6f* Q7f
          *FIFWRENf);                  {601}

FIFWRi=/(FIFWRENf*/CLOCK3);

END$
```

LISTING 2

```
0000,
 FF FF FF FF FF FF FF FF FF FF FF FF FF FF FF
 FF FF FF FF FF FF FF FF FF FF FF FF FF FF FF
 FF FF FF FF FF FF FF FF FF FF FF FF FF FF FF
 FF FF FF FF FF FF FF FF FF FF FF FF FF FF FF
 FF FF FF FF FF FF FF FF FF FF FF FF FF FF FF
 FF FF FF FF FF FE FB F7 F4 F2 F0 ED EB E9 E7
 E3 E2 E0 DE DD DB DA D8 D7 D6 D5 D4 D2 D1 D0
 CE CD CC CB CA C9 C8 C7 C6 C5 C4 C3 C2 C1 C0

0080,
 BE BD BC BB BA BA B9 B8 B7 B6 B5 B4 B4 B3 B2
 B1 B0 B0 AF AE AD AD AC AB AA AA A9 A8 A8 A7
 A6 A5 A5 A4 A3 A3 A2 A1 A1 A0 9F 9E 9E 9D 9D
 9C 9B 9B 9A 9A 99 99 98 98 97 97 96 96 96 95
 94 94 93 93 92 92 91 91 90 90 90 8F 8F 8E 8E
 8D 8D 8D 8C 8C 8C 8B 8B 8B 8A 8A 8A 89 89 89
 88 88 87 87 87 86 86 86 85 85 85 84 84 84 83
 83 82 82 82 81 81 81 80 80 80 7F 7F 7F 7F 7E
```

0100,
```
7E 7E 7D 7D 7D 7C 7C 7C 7B 7B 7B 7A 7A 7A 7A
79 79 78 78 78 78 77 77 77 76 76 76 76 76 75
75 75 74 74 74 73 73 73 73 73 72 72 72 71 71
71 71 71 70 70 6F 6F 6F 6F 6F 6E 6E 6E 6E 6E
6D 6D 6D 6C 6C 6C 6C 6B 6B 6B 6B 6B 6A 6A 6A
6A 69 69 69 69 68 68 68 68 68 68 67 67 67 67
66 66 66 66 65 65 65 65 65 64 64 64 64 64 63
63 63 63 62 62 62 62 62 61 61 61 61 61 60 60
```

0180,
```
60 5F 5F 5F 5F 5F 5F 5E 5E 5E 5E 5E 5D 5D 5D
5D 5C 5C 5C 5C 5C 5C 5B 5B 5B 5B 5A 5A 5A 5A
5A 59 59 59 59 59 59 58 58 58 58 58 58 57 57
57 57 57 56 56 56 56 56 55 55 55 55 55 55 55
54 54 54 54 54 54 53 53 53 53 53 53 52 52 52
52 52 52 51 51 51 51 51 51 50 50 50 50 50 50
4F 4F 4F 4F 4F 4E 4E 4E 4E 4E 4E 4D 4D 4D 4D
4D 4C 4C 4C 4C 4C 4C 4B 4B 4B 4B 4B 4B 4B 4B
```

LISTING 3

```
DALE PERNER
SENTINEL VISION INC.
MAY 4, 1988
1.00
A
P2SPD.ADF
SPEED CONTROL - PROTO TWO

OPTIONS: TURBO = ON
PART:EP600

INPUTS:
        CLOCK1@1,       % from 4060 %
        OVERIDE@11,     % allows external manual selection of speed%
        SPEED@23,       % LP FILTERED SIGNAL FROM FLYING SAUCER, %
                        % 60 DEG BEFORE NEWPULSE%
        OVERDATA@14,    % externally set msb %
        CLOCK2@13       % same as clock1 %

OUTPUTS:
        SPDCNT1@3,
        SPDCNT2@4,
        EOC@5,
        QI@6,           % CLOCK FROM 4060 DIVIDED BY 2 %
        CNTLTCH@7,      % PULSE TO LATCH COUNT INTO 574 IN SYNCH %
                        % WITH CLOCK1 %
        IOVERIDE@8,     % INVERSE OF OVERIDE INPUT %
        Q8LATCHED@9,
        Q8@10,

Q7@22,
        Q6@21,
        Q5@20,
        Q4@19,
        Q3@18,
        Q2@17,
        Q1@16,
        Q0@15
```

NETWORK:

```
CLOCK1=INP(CLOCK1)
OVERIDE=INP(OVERIDE)
SPEED=INP(SPEED)
OVERDATA=INP(OVERDATA)
CLOCK2=INP(CLOCK2)

SPDCNT1,SPDCNT1f=RORF(SPDCNT1d,CLOCK1,GND,GND,VCC)
SPDCNT2,SPDCNT2f=RORF(SPDCNT2d,CLOCK1,GND,GND,VCC)

CNTLTCH,CNTLTCHf=TOTF(CNTLTCHt,CLOCK1,GND,GND,VCC)

IOVERIDE=CONF(IOVERIDEc,VCC)

EOC,EOCf=TOTF(EOCt,CLOCK1,GND,GND,VCC)

QI,QIf=TOTF(QIt,CLOCK1,GND,GND,VCC)
Q0,Q0f=TOTF(Q0t,CLOCK2,GND,GND,VCC)
Q1,Q1f=TOTF(Q1t,CLOCK2,GND,GND,VCC)
Q2,Q2f=TOTF(Q2t,CLOCK2,GND,GND,VCC)
Q3,Q3f=TOTF(Q3t,CLOCK2,GND,GND,VCC)
Q4,Q4f=TOTF(Q4t,CLOCK2,GND,GND,VCC)
Q5,Q5f=TOTF(Q5t,CLOCK2,GND,GND,VCC)
Q6,Q6f=TOTF(Q6t,CLOCK2,GND,GND,VCC)
Q7,Q7f=TOTF(Q7t,CLOCK2,GND,GND,VCC)
Q8,Q8f=TOTF(Q8t,CLOCK1,GND,GND,VCC)

Q8LATCHED=RONF(Q8LATCHEDd,Q8LATCHEDc,GND,GND,VCC)
Q8LATCHEDc=CLKB(Q8LATCHEDi)
```

EQUATIONS:

```
SPDCNT1d=SPEED;
SPDCNT2d=SPDCNT1f;

CNTLTCHt= CNTLTCHf* SPDCNT1f* SPDCNT2f
        +/CNTLTCHf*/SPDCNT1f*/SPDCNT2f;

IOVERIDEc=/OVERIDE;

QIt=CNTLTCHf*/EOCf
   + SPDCNT2f*/EOCf
   + /CNTLTCHf*/SPDCNT2f* QIf;
Q0t=CNTLTCHf*/EOCf* QIf
   + SPDCNT2f*/EOCf* QIf
   + /CNTLTCHf*/SPDCNT2f* Q0f;
Q1t=CNTLTCHf*/EOCf* Q0f* QIf
   + SPDCNT2f*/EOCf* Q0f* QIf
   + /CNTLTCHf*/SPDCNT2f* Q1f;
Q2t=CNTLTCHf*/EOCf* Q1f* Q0f* QIf
   + SPDCNT2f*/EOCf* Q1f* Q0f* QIf
   + /CNTLTCHf*/SPDCNT2f* Q2f;
Q3t=CNTLTCHf*/EOCf* Q2f* Q1f* Q0f* QIf
   + SPDCNT2f*/EOCf* Q2f* Q1f* Q0f* QIf
   + /CNTLTCHf*/SPDCNT2f* Q3f;
Q4t=CNTLTCHf*/EOCf* Q3f* Q2f* Q1f* Q0f* QIf
   + SPDCNT2f*/EOCf* Q3f* Q2f* Q1f* Q0f* QIf
   + /CNTLTCHf*/SPDCNT2f* Q4f;
Q5t=CNTLTCHf*/EOCf* Q4f* Q3f* Q2f* Q1f* Q0f* QIf
   + SPDCNT2f*/EOCf* Q4f* Q3f* Q2f* Q1f* Q0f* QIf
   + /CNTLTCHf*/SPDCNT2f* Q5f;
```

```
Q6t=CNTLTCHf*/EOCf* Q5f* Q4f* Q3f* Q2f* Q1f* Q0f* QIf
   + SPDCNT2f*/EOCf* Q5f* Q4f* Q3f* Q2f* Q1f* Q0f* QIf
   + /CNTLTCHf*/SPDCNT2f* Q6f;
Q7t=CNTLTCHf*/EOCf* Q6f* Q5f* Q4f* Q3f* Q2f* Q1f* Q0f* QIf
   + SPDCNT2f*/EOCf* Q6f* Q5f* Q4f* Q3f* Q2f* Q1f* Q0f* QIf
   + /CNTLTCHf*/SPDCNT2f* Q7f;
Q8t=CNTLTCHf*/EOCf* Q7f* Q6f* Q5f* Q4f* Q3f* Q2f* Q1f* Q0f* QIf
   + SPDCNT2f*/EOCf* Q7f* Q6f* Q5f* Q4f* Q3f* Q2f* Q1f* Q0f* QIf
   + /CNTLTCHf*/SPDCNT2f* Q8f;
EOCt=CNTLTCHf*/EOCf* Q8f* Q7f* Q6f* Q5f* Q4f* Q3f* Q2f
   + SPDCNT2f*/EOCf* Q8f* Q7f* Q6f* Q5f* Q4f* Q3f* Q2f
   + /CNTLTCHf*/SPDCNT2f* EOCf;

Q8LATCHEDd=/OVERIDE* Q8f
         + OVERIDE* OVERDATA;
Q8LATCHEDi=CNTLTCHf;

%CHANGES: JAN05,1988 DALE - CREATE FILE - COPY OF EP900CANIN.ADF %
%         JAN06,1988 DALE - MAKE CNTLATCH SYNC WITH CLOCK1 %
%         MAR09,1988 DALE - ADD CLOCK3, CORRECT MINOR ERRORS %
%         MAR14,1988 DALE - ADD EOC %
%         MAR15,1988 DALE - CHANGE NEWPULSE TO SPEED, ADD SPDPULSE%
%                          TO ALLOW EDGE TRIGGER BY SPEED, NOT LEVEL%
%         APR19,1988 DALE - NUKE SPDPULSE, CLRFLAG, CLOCK2 & ADD DCNTLTCH,%
%                          SPDCNT1, SPDCNT2, S.T. SPEED IS QUALIFIED LO OR HI %
%                          FOR TWO CLOCK PERIODS%
%         MAY04,1988 DALE - REMOVE DCNTLTCH, CHANGE COUNT RESET METHOD %

END$
```

*LISTING 4*

```
DALE PENNER
SENTINEL VISION INC.
APRIL 18, 1988
1.00
A
P2DAGC.ADF
CANIN DETECTOR FOR DEFAULT AGC - PROTO TWO

OPTIONS: TURBO = ON
PART:EP900

INPUTS:
     CLOCK1@1      % from speed control %
     ASIG@2,       % from opto sw on machine %
     BSIG@3,       % from opto sw on machine %
     QA@4,
     CLOCK2@21,    % from speed control %
     QB@37,
     START@38,     % from ccdctlr cct %
     DATA@39       % from comparator (active low) %

OUTPUTS:

Q0@5,
     Q1@6,
     Q2@7,
     Q3@8,
     Q4@9,
     Q5@10,
```

```
        Q6@11,
        Q7@12,
        WINDOW@13
        NEWCAN@16,
        V2TRUE@36,
        N0@35,
        N1@34,
        N2@33,
        N3@32,
        N4@31,
        N5@30,
        CANIN@29,
        AORB@27,
        AORBDEL@26

NETWORK:

CLOCK1=INP(CLOCK1)
        ASIG=INP(ASIG)
        BSIG=INP(BSIG)
        QA=INP(QA)
        QB=INP(QB)
        CLOCK2=INP(CLOCK2)
        START=INP(START)
        DATA=INP(DATA)

Q0,Q0f=TOTF(Q0t,CLOCK1,QRST,GND,VCC)
        Q1,Q1f=TOTF(Q1t,CLOCK1,QRST,GND,VCC)
        Q2,Q2f=TOTF(Q2t,CLOCK1,QRST,GND,VCC)
        Q3,Q3f=TOTF(Q3t,CLOCK1,QRST,GND,VCC)
        Q4,Q4f=TOTF(Q4t,CLOCK1,QRST,GND,VCC)
        Q5,Q5f=TOTF(Q5t,CLOCK1,QRST,GND,VCC)
        Q6,Q6f=TOTF(Q6t,CLOCK1,QRST,GND,VCC)
        Q7,Q7f=TOTF(Q7t,CLOCK1,QRST,GND,VCC)
        WINDOW,WINDOWf=JOJF(WINDOWj,CLOCK1,WINDOWk,GND,GND,VCC)

NEWCAN,NEWCANf=RORF(NEWCANd,CLOCK1,GND,GND,VCC)

V2TRUE,V2TRUEf=RORF(V2TRUEd,CLOCK2,GND,GND,VCC)
        N0,N0f=TOTF(N0t,CLOCK2,NRST,GND,VCC)
        N1,N1f=TOTF(N1t,CLOCK2,NRST,GND,VCC)
        N2,N2f=TOTF(N2t,CLOCK2,NRST,GND,VCC)
        N3,N3f=TOTF(N3t,CLOCK2,NRST,GND,VCC)
        N4,N4f=TOTF(N4t,CLOCK2,NRST,GND,VCC)
        N5,N5f=TOTF(N5t,CLOCK2,NRST,GND,VCC)
        CANIN,CANINf=JOJF(CANINj,CLOCK2,CANINk,CANINRST,GND,VCC)

AORB,AORBf=JOJF(AORBj,CLOCK2,AORBk,GND,GND,VCC)
        AORBDEL,AORBDELf=RORF(AORBDELd,CLOCK2,GND,GND,VCC)

EQUATIONS:
        Q0t= QA* QB*/Q7f;
        Q1t=Q0f* QA* QB*/Q7f;
        Q2t=Q1f*Q0f* QA* QB*/Q7f;
        Q3t=Q2f*Q1f*Q0f* QA* QB*/Q7f;
        Q4t=Q3f*Q2f*Q1f*Q0f* QA* QB*/Q7f;
        Q5t=Q4f*Q3f*Q2f*Q1f*Q0f* QA* QB*/Q7f;
        Q6t=Q5f*Q4f*Q3f*Q2f*Q1f*Q0f* QA* QB*/Q7f;
        Q7t=Q6f*Q5f*Q4f*Q3f*Q2f*Q1f*Q0f* QA* QB*/Q7f;
```

```
    QRST=START;
        %RESETS PIXEL COUNT TO ZERO WHEN BLACK & GARBAGE PIXELS HAVE %
        %ALREADY PASSED %
    WINDOWj= Q0f* Q1f*/Q2f*/Q3f* Q4f*/Q5f*/Q6f*/Q7f;  %ON #19%
    WINDOWk= Q0f* Q1f*/Q2f*/Q3f* Q4f*/Q5f*/Q6f*/Q7f;  %OFF #19+64%

NEWCANd= ( AORBDELf* /AORBf)
           + (/AORBDELf*AORBf);

V2TRUEd=WINDOWf*/QA* QB*/DATA; %CHOOSE QA,QB TO LINE WITH DATA%

N0t= ( V2TRUEf*/CANINf);
    N1t= ( V2TRUEf* N0f*/CANINf);
    N2t= ( V2TRUEf* N0f* N1f*/CANINf);
    N3t= ( V2TRUEf* N0f* N1f* N2f*/CANINf);
    N4t= ( V2TRUEf* N0f* N1f* N2f* N3f*/CANINf);
    N5t= ( V2TRUEf* N0f* N1f* N2f* N3f* N4f*/CANINf);
    NRST= NEWCANf;
    CANINj= N0f* N1f* N2f* N3f* N4f* N5f;
        %SET ON A COUNT OF 31 V2TRUE (VIEW2 CAN DATA)%
    CANINk=GND;
    CANINRST=NEWCANf;

AORBj= /ASIG * BSIG;
    AORBk= /BSIG * ASIG;
    AORBDELd= AORBf;

%*********************     CHANGES        ************************ %
%JAN05, 1988 DALE - CREATE FILE - COPY OF EP900INSPD.ADF            %
%JAN16, 1988 DALE - CHANGE AWATCH TO AORB                           %
%MAR15, 1988 DALE - CHANGE A,B TO ASIG,BSIG                         %
%MAR16, 1988 DALE - CHANGE FILENAME FROM EP900CAN.ADF TO P2DAGC.ADF, NUKE %
%                   NEWCAN, CHANGE NEWPULSE TO NEWCAN, NUKE BWATCH  %
%MAR23, 1988 DALE - CHANGE V2TRUE FOR QA,QB TIMING                  %
%MAR28, 1988 DALE - CHANGE ASIG, BSIG FOR NEG'V LOGIC               %
%APR18, 1988 DALE - QUALIFY AORBJ & AORBK TO INCREASE NOISE IMMUNITY%

END$
```

*LISTING 5*

```
RICK SLAMKA
SENTINEL VISION INC.
FEBRUARY 5,1988
1.00
A
P2ENC.ADF
CCD CONTROLLER BOARD DATA ENCODER; PROVIDES START=FF, STOP=00
CHANGES FF TO FE, 00 TO 01
OPTIONS:TURBO=ON
PART:EP600

INPUTS:
    CLOCK1@1,
    CLOCK2@13,
    START@2,
    STOP@23
    D0@4,
    D1@5,
    D2@6,
    D3@7,
```

```
        D4@8,
        D5@9,
        D6@10,
        D7@11,
        D8@14    %ADC OVERFLOW BIT%

OUTPUTS:

Q0@3,
        Q1@22,
        Q2@21,
        Q3@20,
        Q4@19,
        Q5@18,
        Q6@17,
        Q7@16,
        Q8@15
NETWORK:
        START=INP(START)
        STOP=INP(STOP)
        D0=INP(D0)
        D1=INP(D1)
        D2=INP(D2)
        D3=INP(D3)
        D4=INP(D4)
        D5=INP(D5)
        D6=INP(D6)
        D7=INP(D7)
        D8=INP(D8)
        CLOCK1=INP(CLOCK1)
        CLOCK2=INP(CLOCK2)

Q0=RONF(Q0d,CLOCK1,GND,GND,VCC)
        Q1=RONF(Q1d,CLOCK2,GND,GND,VCC)
        Q2=RONF(Q2d,CLOCK2,GND,GND,VCC)
        Q3=RONF(Q3d,CLOCK2,GND,GND,VCC)
        Q4=RONF(Q4d,CLOCK2,GND,GND,VCC)
        Q5=RONF(Q5d,CLOCK2,GND,GND,VCC)
        Q6=RONF(Q6d,CLOCK2,GND,GND,VCC)
        Q7=RONF(Q7d,CLOCK2,GND,GND,VCC)
        Q8=RONF(Q8d,CLOCK2,GND,GND,VCC)

EQUATIONS:

Q0d=(D0*/D1*/START*/STOP)
           +(D0*/D2*/START*/STOP)
           +(D0*/D3*/START*/STOP)
           +(D0*/D4*/START*/STOP)
           +(D0*/D5*/START*/STOP)
           +(D0*/D6*/START*/STOP)
           +(D0*/D7*/START*/STOP)
           +START;

% 00H changes to 02H via Q2d, FFH changes to FEH via Q1d %

Q1d=(/D0*/D1*/D2*/D3*/D4*/D5*/D6*/D7*/START*/STOP)
           +(D1*/START*/STOP)
           +(START);

Q2d=(D2*/START*/STOP)
           +(START);
```

```
        Q3d=(D3*/START*/STOP)
           +(START);

Q4d=(D4*/START*/STOP)
           +(START);

Q5d=(D5*/START*/STOP)
           +(START);

Q6d=(D6*/START*/STOP)
           +(START);

Q7d=(D7*/START*/STOP)
           +(START);

Q8d=D8;    %ADC OVERFLOW BIT PASSED THROUGH TO MOTHERBOARD%

END$
```

LISTING 6

```
RICK SLAMKA
SENTINEL VISION INC.
MAY 30, 1988
1.00
A
EP900
P2XMT
TAXI TRANSMITTER CONTROLLER FOR PROTO2 HEAD, ONE OR TWO HEAD OPERATION
OPTIONS:TURBO=ON
PART:EP900

INPUTS:
%NOTE: THIS DEVICE SENDS EACH HEADSET DATA SEPARATELY IN DUAL MODE%
        TAXICLK1@1,
        TAXICLK2@21,
        TAXICLK3@28,
        EOS@12,      %pulse from CCDCONTROLLER %
        START@13,    %pulse from CCDCONTROLLER %
        STOP@14,     %pulse from CCDCONTROLLER loading 0's in data%
        D0@37,       %LSB of data, dropped in 8 bit TAXI mode%
        D1@38,
        D2@39,
        D3@19,
        D4@18,
        D5@17,
        D6@4,
        D7@3,        %MSB of data%
        D8@2,        %0=headset0, 1=headset1%
        NEWCAN0@24,  %this pulse is produced by the slot switch%
        1OR2@22,     %hi=single fifo, lo=dual fifo's%
        MODE@23      %hi=9bit xmisssion, lo=8bit xmission%

OUTPUTS:
        STARTED@11,
        STRBEN@16,
        STRB@15,
        RSTCAP@27,   %CAPTURES NEWCAN0 TO INITIATE RST SEQUENCE%
        RSTPEN@26,   %SECONDARY SYCH OF RST TO SCAN XMIT SEQUENCE%
        COM0@25,
        FIFRD1@35,   %ACTIVE HIGH, INVERTED LATER%
```

```
        FIFRD0@36,      !ACTIVE HIGH, INVERTED LATER!
        FIFRST@9,       !ACTIVE HIGH, INVERTED LATER!
        DATALCH@5,
        DIAGLCH@6,

ENODIAG@7,
        EN1DIAG@8,

RDSEL@34,

Q0@33,
        Q1@32,
        Q2@31

NETWORK:
        CLOCK1=INP(TAXICLK1)
        CLOCK2=INP(TAXICLK2)
        TAXICLK3=INP(TAXICLK3)
        STOP=INP(STOP)
        EOS=INP(EOS)
        START=INP(START)
        D0=INP(D0)
        D1=INP(D1)
        D2=INP(D2)
        D3=INP(D3)
        D4=INP(D4)
        D5=INP(D5)
        D6=INP(D6)
        D7=INP(D7)
        D8=INP(D8)
        NEWCAN0=INP(NEWCAN0)
        1OR2=INP(1OR2)
        MODE=INP(MODE)

STRBEN,STRBENf=TOTF(STRBENt,CLOCK1,GND,GND,VCC)

STARTED,STARTEDf=RORF(VCC,STARTCLK,STARTCLR,GND,VCC)
        STARTCLK=CLKB(STOP)
        STRB=CONF(STRBi,VCC)
        COMO=RONF(COMOd,CLOCK2,GND,GND,VCC)
        FIFRD1=CONF(FIFRD1i,VCC)
        FIFRD0=CONF(FIFRD0i,VCC)
        FIFRST,FIFRSTf=COIF(FIFRSTi,VCC)
        RSTCAP,RSTCAPf=RORF(VCC,RSTCLK,RSTCLR,GND,VCC)
        RSTCLK=CLKB(NEWCAN0)
        RSTPEN,RSTPENf=RORF(VCC,PENCLK,RSTCLR,GND,VCC)
        PENCLK=CLKB(PENRST)
        DATALCH=CONF(DATALCHi,VCC)

ENODIAG=RONF(ENODIAGd,CLOCK1,GND,GND,VCC)
        EN1DIAG=RONF(EN1DIAGd,CLOCK1,GND,GND,VCC)

Q0,Q0f=TOTF(Q0t,CLOCK2,GND,GND,VCC)
        Q1,Q1f=TOTF(Q1t,CLOCK2,GND,GND,VCC)
        Q2,Q2f=TOTF(Q2t,CLOCK2,GND,GND,VCC)
        DIAGLCH,EOCf=JOJF(EOCj,CLOCK1,EOCk,GND,GND,VCC)

RDSEL,RDSELf=TOTF(RDSELt,CLOCK2,RDSELCLR,GND,VCC)
```

EQUATIONS:

```
STRBENt=( Q0f*/Q1f*/Q2f*/STRBENf*/RSTPENf)
        %STRB AND FIFRD DISABLED ON RESET%
       +(/D0*/D1*/D2*/D3*/D4*/D5*/D6*/D7*/D8* STRBENf* EOCf* MODE* 1OR2)
       +(    /D1*/D2*/D3*/D4*/D5*/D6*/D7*/D8* STRBENf* EOCf*/MODE* 1OR2)
       +(/D0*/D1*/D2*/D3*/D4*/D5*/D6*/D7* D8* STRBENf* EOCf* MODE*/1OR2)
       +(    /D1*/D2*/D3*/D4*/D5*/D6*/D7* D8* STRBENf* EOCf*/MODE*/1OR2);
         %STRB AND FIFRD STOP ON LOCAL 0 FOR SINGLE MODE, %
         %                      ON REMOTE ZERO FOR DUAL MODE%

Q0t=(/EOCf)
   +(Q0f*EOCf);
Q1t=(/EOCf*Q0f)
   +(Q1f*EOCf);
Q2t=(/EOCf*Q0f*Q1f)
   +(Q2f*EOCf);

EOCj= Q0f* Q1f* Q2f;
EOCk= STARTEDf;

STARTCLR= Q0f* Q1f*/Q2f;%GLITCHES CAN OCCUR BUT SHOULDN'T BE A PROBLEM%
COMod=(/EOCf* Q0f*/Q1f*/Q2f)
     +(/EOCf*/Q0f* Q1f*/Q2f);
%DRIVES COM'S ON TAXI,DENOTES COMING OF DIAGDATA%

STRBi= /TAXICLK3*STRBENf;

FIFRD1i= RDSELf*/TAXICLK3* STRBENf* EOCf;
FIFRD0i=/RDSELf*/TAXICLK3* STRBENf* EOCf;
RDSELt=(/RDSELf*EOCf* STRBENf*/1OR2
        */D0*/D1*/D2*/D3*/D4*/D5*/D6*/D7*/D8* MODE)
      +(/RDSELf*EOCf* STRBENf*/1OR2
         */D1*/D2*/D3*/D4*/D5*/D6*/D7*/D8*/MODE);

RDSELCLR=STOP;

RSTCLR= RSTPENf* START;   %CLR FOR RSTCAP AND RSTPEN%
FIFRSTi= RSTPENf* EOS;    %ACTIVE HIGH,INVERTED LATER%
PENRST= RSTCAPf* STOP;    %CLOCK FOR RST PEN%

DATALCHi= TAXICLK3;

ENODIAGd=( Q0f* Q1f*/Q2f)
        +(/Q0f*/Q1f* Q2f);

EN1DIAGd=( Q0f*/Q1f* Q2f)
        +(/Q0f* Q1f* Q2f);

END$
```

LISTING 7

```
RICK SLAMKA
SENTINEL VISION INC.
P2RCVSER, MARCH 24, 1988
1.00
A
EP900
P2RCVSER.ADF
TAXI DATA RECEIVER, SEQUENTIAL NON-INTERLACED SCANS IN DUAL MODE
OPTIONS:TURBO=ON
PART:EP900
INPUTS:
% USE THIS DEVICE WITH P2XMTSER WHEN OPERATING IN DUAL MODE%
    DSTRB1@1,
    D0@2,
    D1@3,
    D2@4,
    D3@17,
    D4@18,
    D5@19,
    D6@39,      %DATA MSB%
    D7@38,      %DATA HEADSET TAG BIT%
    D8@37,      %DATA LSB, DROPPED WHEN TAXI IN 8 BIT MODE%
    DSTRB2@21,
    DSTRB3@22,
    VLTN@23,        %TAGS POORLY RECEIVED DATA%
    CSTRB@14,       %USED TO SUPPLEMENT DSTRB DURING VIOLKATIONS%
    MODE@24,        %HI=9BIT MODE, LO=8BIT MODE%
    1OR2@25,        %HI FOR LOCAL ONLY, LO FOR DUAL HEADSET RECEPTION%
    C0@36,
    C1@35,
    C2@34

OUTPUTS:
    Q0@5,
    Q1@6,
    Q2@7,
    Q3@8,
    Q4@9,
    Q5@10,
    Q6@11,
    Q7@12,
    Q8@13,
    DAT0L@15,       %LATCHES HEADSET0 DATA ONTO LOCAL APP BUS%
    DAT1L@16,       %LATCHES HEADSET1 DATA ONTO REMOTE APP BUS%
    DIA0L@26,       %LATCHES HEADSET0 DIAGNOSTICS%
    DIA1L@27,       %LATCHES HEADSET1 DIAGNOSTICS%
    DATCLK@28,      %MIXES CSTRB AND DSTRB TO PRESERVE DEMUX DURING VLTN%
    COUNT0@33,
    COUNT1@32,
    COMRST@31,
    EOC@30,
    COMEN@29        %DISTINGUISHES BETWEEN DIAG AND DATA%

NETWORK:
    DSTRB1=INP(DSTRB1)
    DSTRB3=INP(DSTRB3)
    DSTRB2=INP(DSTRB2)
    CSTRB=INP(CSTRB)
```

```
D0=INP(D0)
D1=INP(D1)
D2=INP(D2)
D3=INP(D3)
D4=INP(D4)
D5=INP(D5)
D6=INP(D6)      %DATA MSB%
D7=INP(D7)      %DATA HEADSET TAG BIT%
D8=INP(D8)      %DATA LSB, DROPPED WHEN TAXI IN 8 BIT MODE%
VLTN=INP(VLTN)           %TAGS POORLY RECEIVED DATA%
MODE=INP(MODE)           %HI=9BIT MODE, LO=8BIT MODE%
1OR2=INP(1OR2)       %HI FOR LOCAL ONLY, LO FOR DUAL HEADSET RECEPTION%
C0=INP(C0)
C1=INP(C1)
C2=INP(C2)

Q0=RONF(Q0d,DSTRB1,GND,GND,VCC)
Q1=RONF(Q1d,DSTRB1,GND,GND,VCC)
Q2=RONF(Q2d,DSTRB1,GND,GND,VCC)
Q3=RONF(Q3d,DSTRB1,GND,GND,VCC)
Q4=RONF(Q4d,DSTRB1,GND,GND,VCC)
Q5=RONF(Q5d,DSTRB1,GND,GND,VCC)
Q6=RONF(Q6d,DSTRB1,GND,GND,VCC)
Q7=RONF(Q7d,DSTRB1,GND,GND,VCC)
Q8,Q8f=TOTF(Q8t,DSTRB1,GND,GND,VCC)

DATCLK,DATCLKf=COIF(DATCLKi,VCC)

DAT0L=CONF(DATA0Li,VCC)
DAT1L=CONF(DATA1Li,VCC)
DIA0L=CONF(DIA0Li,VCC)
DIA1L=CONF(DIA1Li,VCC)
COUNT0,COUNT0f=TOTF(COUNT0t,DSTRB2,GND,GND,VCC)
COUNT1,COUNT1f=TOTF(COUNT1t,DSTRB2,GND,GND,VCC)
EOC,EOCf=TOTF(EOCt,DSTRB2,GND,GND,VCC)
COMRST,COMRSTf=RORF(COMRSTd,DSTRB2,GND,GND,VCC)
COMEN,COMENf=RORF(VCC,COMCLK,COMCLR,GND,VCC)
COMCLK=CLKB(COMCLKi)

EQUATIONS:

Q0d=(/VLTN* D8* D0*/COMENf* MODE)    %ONLY IF DATA NOT 01 IS Q0 ALLOWED TO BE HIGH%
    +(/VLTN* D8* D1*/COMENf* MODE)
    +(/VLTN* D8* D2*/COMENf* MODE)
    +(/VLTN* D8* D3*/COMENf* MODE)
    +(/VLTN* D8* D4*/COMENf* MODE)
    +(/VLTN* D8* D5*/COMENf* MODE)
    +(/VLTN* D8* D6*/COMENf* MODE)
    +VLTN*/COMENf;

Q1d=(/VLTN* D8*/D0*/D1*/D2*/D3*/D4*/D5*/D6*/COMENf* MODE)
    +(/VLTN* D0*/COMENf);   %Q1 CHANGED TO Q2 IN 9 BIT DATA MODE%

Q2d=/VLTN* D1*/COMENf;

Q3d=/VLTN*D2*/COMENf;

Q4d=/VLTN*D3*/COMENf;

Q5d=/VLTN*D4*/COMENf;
```

```
Q6d=/VLTN*D5*/COMENf;

Q7d=/VLTN*D6*/COMENf;

Q8t=( Q8f* COMENf)
    +(/Q8f*/VLTN* D0* D1* D2* D3* D4* D5* D6* D7);
%REMOTE FF CHANGES Q8 WHICH ACTIVATES DATA1LATCH IN DUAL MODE%

DATCLKi= DSTRB3 + CSTRB;   %CSTRB ADDED TO PRESERVE DEMUX DURING VLTN%

DATA0Li=( EOCf* DATCLKf*/Q8f*/10R2)   %DUAL HEADSET MODE%
       +( EOCf* DATCLKf* 10R2);       %SINGLE(LOCAL) HEADSET MODE%

DATA1Li= EOCf* DATCLKf* Q8f*/10R2;    %DUAL HEADSET MODE%

DIA0Li=( COMENf     * DSTRB3*/VLTN*/D7);
DIA1Li=( COMENf*/10R2* DSTRB3*/VLTN* D7);

COMCLKi= C0* C1* C2*/VLTN;         %COM LINES GOING HI DENOTES START OF SCAN%
COMCLR= COMRSTf;              %END OF DIAGNOSTICS%
COMRSTd=/COUNT0f* COUNT1f;    %END OF DIAGNOSTICS%

COUNT0t=(/EOCf)
       +( EOCf* COUNT0f);

COUNT1t=(/EOCf* COUNT0f)
       +( EOCf* COUNT1f);

EOCt=( EOCf*COMENf)
    +(/EOCf* COUNT1f* COUNT0f);

END$
```

LISTING 8

```
RICK SLANKA
SENTINEL VISION INC.
NOV 27, 1987 CHANGES:DALE DEC15,1987- CHANGE STRTSO1j = 5
1.00
A
P2TXBAP2.ADF
BUFFER TO APP INTERFACE SECONDARY (DATA) CONTROLLER, DEMULTIPLEXER
OPTIONS:TURBO=ON
PART:EP900

INPUTS:
    CLK1@1,
    CLK3@2,
    CLK2@21,
    ENABLE@3,
    NEWPAR@4,
    D0@17,
    D1@18,
    D2@19,
    D3@22,
    D4@23,
    D5@24,
    PCNTRCH@29,
```

```
     D6@37,
     D7@38,
     D8@39

OUTPUTS:
     FFDET@5,
             %FF=START%
     ERDET@6,
             %01=ERROR%
     ERDETRG@7,
             %01=ERROR%
     A574SIN@8,
     B574SIN@9,
     C574SIN@10,
     D574SIN@11,
     LATCHIN@12,
     FFDETRG@13,
     FIFSO1@14,
     FIFSO2@15,
     STRTSO1@16,
     STRTSO2@25,
     APPRST@26,
     EOS@27,
     PSTART@28,
     PCNTCLR@30,
     Q1@31,
     Q0@32,
     DELC3@33,
     DELC2@34,
     DELC1@35,
     DELC0@36

NETWORK:
     CLK1=INP(CLK1)
     CLK3=INP(CLK3)
     CLK2=INP(CLK2)
     ENABLE=INP(ENABLE)
     D0=INP(D0)
     D1=INP(D1)
     D2=INP(D2)
     D3=INP(D3)
     D4=INP(D4)
     D5=INP(D5)
     D6=INP(D6)
     D7=INP(D7)
     D8=INP(D8)
     NEWPAR=INP(NEWPAR)
     PCNTRCH=INP(PCNTRCH)

FFDETRG,FFDETRGf=RORF(FFDETRGd,CLK1,GND,GND,VCC)
             %FF=START%
     FFDET,FFDETf=COIF(FFDETi,VCC)
             %FF=START%
     ERDET,ERDETf=COIF(ERDETi,VCC)
             %01=ERROR%
     ERDETRG,ERDETRGf=RORF(ERDETRGd,CLK1,GND,GND,VCC)
     A574SIN=CONF(A574SINi,VCC)
     B574SIN=CONF(B574SINi,VCC)
     C574SIN=CONF(C574SINi,VCC)
```

```
D574SIN=CONF(D574SINi,VCC)
LATCHIN,LATCHINf=RORF(LATCHINd,CLK1,GND,GND,VCC)

FIFSO1=RONF(FIFOSO1d,CLK1,GND,GND,VCC)
FIFSO2=RONF(FIFOSO2d,CLK1,GND,GND,VCC)
STRTSO1,STRTSO1f=JOJF(STRTSO1j,CLK1,STRTSO1k,GND,GND,VCC)
STRTSO2,STRTSO2f=JOJF(STRTSO2j,CLK2,STRTSO2k,GND,GND,VCC)
PCLK=CLKB(LATCHINf)
DELC0,DELC0f=TOTF(DELC0t,PCLK,PCLR,GND,VCC)
DELC1,DELC1f=TOTF(DELC1t,PCLK,PCLR,GND,VCC)
DELC2,DELC2f=TOTF(DELC2t,PCLK,PCLR,GND,VCC)
DELC3,DELC3f=TOTF(DELC3t,PCLK,PCLR,GND,VCC)
Q0,Q0f=TOTF(Q0t,CLK2,GND,GND,VCC)
Q1,Q1f=TOTF(Q1t,CLK2,GND,GND,VCC)
PCNTCLR=RONF(PCNTCLRd,CLK2,GND,GND,VCC)
PSTART,PSTARTf=JOJF(PSTARTj,CLK2,PSTARTk,GND,GND,VCC)
EOS=RONF(EOSd,CLK2,GND,GND,VCC)
APPRST=RONF(APPRSTd,CLK2,GND,GND,VCC)

EQUATIONS:

FFDETRGd= D0* D1* D2* D3* D4* D5* D6* D7;  %* D8;%
            %FF=START%

FFDETi= D0* D1* D2* D3* D4* D5* D6* D7;  %* D8;%
            %FF=START%

ERDETi= D0*/D1*/D2*/D3*/D4*/D5*/D6*/D7;  %* D8;%
            %01=ERROR%

ERDETRGd=(D0*/D1*/D2*/D3*/D4*/D5*/D6*/D7); %* D8%
%           +( D8*/NEWPAR)     %
%           +(/D8* NEWPAR);    %
    %01 OR PARITY ERRORS DETECTED TO DISABLE APP LOADUP%

Q0t=(PSTARTf)
       +(/PSTARTf* Q0f);

Q1t=(PSTARTf*Q0f)
       +(/PSTARTf* Q1f);

DELC0t=PSTARTf;

DELC1t=PSTARTf*DELC0f;

DELC2t=PSTARTf*DELC0f*DELC1f;

DELC3t=PSTARTf*DELC0f*DELC1f*DELC2f;

PCLR=/PSTARTf;

A574SINi=(/Q0f*/Q1f* PSTARTf*/CLK3*/ERDETRGf)
            +(/Q0f*/Q1f* PSTARTf*/CLK3*/ERDETRGf);

B574SINi=( Q0f*/Q1f* PSTARTf*/CLK3*/ERDETRGf)
            +( Q0f*/Q1f* PSTARTf*/CLK3*/ERDETRGf);

C574SINi=(/Q0f* Q1f* PSTARTf*/CLK3*/ERDETRGf)
            +(/Q0f* Q1f* PSTARTf*/CLK3*/ERDETRGf);
```

```
D574SINi=( Q0f* Q1f* PSTARTf*/CLK3*/ERDETRGf)
        +( Q0f* Q1f* PSTARTf*/CLK3*/ERDETRGf);

LATCHINd={(/Q0f* Q1f)
         +( Q0f* Q1f);

STRTSO1j= /DELC0f*DELC1f*/DELC2f*/DELC3f;

STRTSO1k=/PSTARTf;

STRTSO2j= DELC0f* DELC1f* DELC2f*/DELC3f;

STRTSO2k=/PSTARTf;

FIFOSO1d=/((STRTSO1f*/Q0f* Q1f)

+(STRTSO1f* Q0f* Q1f));
     %FIFOSO IN PHASE WITH LATCHIN TO AVOID STAGGERED DAC GLITCHES%

FIFOSO2d=/((STRTSO2f*/Q0f* Q1f)
        +(STRTSO2f* Q0f* Q1f));
     %FIFOSO IN PHASE WITH LATCHIN TO AVOID STAGGERED DAC GLITCHES%

PSTARTj=(ENABLE*FFDETRGf*/FFDETf*/ERDETf)  %* NEWPAR* D8)%
       +(ENABLE*FFDETRGf*/FFDETf*/ERDETf);  %*/NEWPAR*/D8);%
     %SCAN LOADIN TO APP PROCEEDS ONLY UNDER THE CONDITION%
     %THAT A TRANSITION FROM FF TO VALID DATA IS MADE%

PSTARTk=(/PCNTRCH)
       +(/D0*/D1*/D2*/D3*/D4*/D5*/D6*/D7)  %*/D8)%
       +(/ENABLE);

EOSd=/PCNTRCH;
     %ONLY WHEN THE CORRECT NUMBER OF PIXELS HAVE BEEN LOADED%
     %WILL AN EOS BE GIVEN TO ALLOW A LOADOUT OF VALUES FROM %
     %THE APP TO THE INTERFACE%

APPRSTd= PCNTRCH;    %INVERSE OF EOS DUE TO ON BOARD INVERTER%

PCNTCLRd=/PSTARTf;

END$
```

LISTING 9a (VIEW 1)

```
NADER RIAHI
SENTINEL VISION INC.
NOV 1, 1988
1.00
A
EP900
DIGITAL CONTROLLER FOR THE APP/R (V-1). PROTOII - PINOUT DIFFERS
OPTIONS: TURBO = ON

PART:EP900
INPUTS:
        CLOCK1@1,
        CLOCK2@21,
        PXCLOCK@38,
        COMPA@2,
        COMPB@3,
        HEAD@4,
        MENABLE@39

OUTPUTS:
        START@5,
        STOP@6,
        ENCONT@7,
        SQ0@15,
        SQ1@14,
        SQ2@13,
        SQ3@12,
        SQ4@11,
        SQ5@10,
        SQ6@9,
        SQ7@8,
        STOPEN@16,
        STARTE@25,
        STARTL@36,
        STOPL@35,
        MQ0@26,
        MQ1@27,
        MQ2@28,
        MQ3@29,
        MQ4@30,
        MQ5@31,
        MQ6@32,
        MQ7@33
NETWORK:
        CLOCK1=INP(CLOCK1)
        CLOCK2=INP(CLOCK2)
        COMPA=INP(COMPA)
        COMPB=INP(COMPB)
        HEAD=INP(HEAD)
        PXCLOCK=INP(PXCLOCK)
        MENABLE=INP(MENABLE)

START,STARTi=RORF(STARTd,STARTc,CLEAR,GND,VCC)
        STARTc=CLKB(STARTi)
```

```
STOP,STOPf=RORF(STOPd,STOPc,CLEAR,GND,VCC)
STOPc=CLKB(STOPi)
ENCONT,ENCONTf=RORF(ENCONTd,CLOCK1,CLEAR,GND,VCC)

SQ0,SQ0f=TOTF(SQ0t,CLOCK1,CLEAR,GND,VCC)
SQ1,SQ1f=TOTF(SQ1t,CLOCK1,CLEAR,GND,VCC)
SQ2,SQ2f=TOTF(SQ2t,CLOCK1,CLEAR,GND,VCC)
SQ3,SQ3f=TOTF(SQ3t,CLOCK1,CLEAR,GND,VCC)
SQ4,SQ4f=TOTF(SQ4t,CLOCK1,CLEAR,GND,VCC)
SQ5,SQ5f=TOTF(SQ5t,CLOCK1,CLEAR,GND,VCC)
SQ6,SQ6f=TOTF(SQ6t,CLOCK1,CLEAR,GND,VCC)
SQ7,SQ7f=TOTF(SQ7t,CLOCK1,CLEAR,GND,VCC)

STARTE,STARTEf=TOTF(STARTEt,STARTEc,CLEAR,GND,VCC)
STARTEc=CLKB(STARTEi)
STOPEN,STOPENf=TOTF(STOPENt,STOPENc,CLEAR,GND,VCC)
STOPENc=CLKB(STOPENi)

STARTL=RONF(STARTLd,STARTLc,CLEAR,GND,VCC)
STARTLc=CLKB(STARTLi)
STOPL=RONF(STOPLd,STOPLc,CLEAR,GND,VCC)
STOPLc=CLKB(STOPLi)

MQ0,MQ0f=TOTF(MQ0t,CLOCK2,CLEAR,GND,VCC)
MQ1,MQ1f=TOTF(MQ1t,CLOCK2,CLEAR,GND,VCC)
MQ2,MQ2f=TOTF(MQ2t,CLOCK2,CLEAR,GND,VCC)
MQ3,MQ3f=TOTF(MQ3t,CLOCK2,CLEAR,GND,VCC)
MQ4,MQ4f=TOTF(MQ4t,CLOCK2,CLEAR,GND,VCC)
MQ5,MQ5f=TOTF(MQ5t,CLOCK2,CLEAR,GND,VCC)
MQ6,MQ6f=TOTF(MQ6t,CLOCK2,CLEAR,GND,VCC)
MQ7,MQ7f=TOTF(MQ7t,CLOCK2,CLEAR,GND,VCC)

EQUATIONS:
    STARTd=STARTEf;
    STARTi=COMPA;
    STOPd=STOPENf;
    STOPi=COMPB;
    STARTEt=(( MQ0f* MQ1f* MQ2f* MQ3f*/MQ4f*/MQ5f*/MQ6f*/MQ7f*/HEAD)
            +(/MQ0f*/MQ1f* MQ2f*/MQ3f* MQ4f*/MQ5f*/MQ6f*/MQ7f* HEAD))
            */STARTEf;         %15 AND 20%
    STARTEi=/PXCLOCK;
    STOPENt=(( SQ0f* SQ1f*/SQ2f*/SQ3f*/SQ4f* SQ5f*/SQ6f*/SQ7f*/HEAD)
            +( SQ0f*/SQ1f* SQ2f*/SQ3f*/SQ4f* SQ5f*/SQ6f*/SQ7f* HEAD))
            */STOPENf;         %35 AND 37%
    STOPENi=/PXCLOCK;
    ENCONTd=STARTf;
    STARTLd=(STARTf)
           +(/MQ0f* MQ1f*/MQ2f*/MQ3f*/MQ4f*/MQ5f*/MQ6f*/MQ7f);
    STARTLi=/PXCLOCK;
    STOPLd=(STOPf)
          +( MQ0f*/MQ1f* MQ2f* MQ3f* MQ4f* MQ5f* MQ6f*/MQ7f);
    STOPLi=/PXCLOCK;
    CLEAR=MENABLE;

SQ0t=ENCONTf;
    SQ1t=ENCONTf*SQ0f;
    SQ2t=ENCONTf*SQ0f*SQ1f;
    SQ3t=ENCONTf*SQ0f*SQ1f*SQ2f;
    SQ4t=ENCONTf*SQ0f*SQ1f*SQ2f*SQ3f;
    SQ5t=ENCONTf*SQ0f*SQ1f*SQ2f*SQ3f*SQ4f;
    SQ6t=ENCONTf*SQ0f*SQ1f*SQ2f*SQ3f*SQ4f*SQ5f;
    SQ7t=ENCONTf*SQ0f*SQ1f*SQ2f*SQ3f*SQ4f*SQ5f*SQ6f;
```

```
MQ0t=/MENABLE;
MQ1t=/MENABLE*MQ0f;
MQ2t=/MENABLE*MQ0f*MQ1f;
MQ3t=/MENABLE*MQ0f*MQ1f*MQ2f;
MQ4t=/MENABLE*MQ0f*MQ1f*MQ2f*MQ3f;
MQ5t=/MENABLE*MQ0f*MQ1f*MQ2f*MQ3f*MQ4f;
MQ6t=/MENABLE*MQ0f*MQ1f*MQ2f*MQ3f*MQ4f*MQ5f;
MQ7t=/MENABLE*MQ0f*MQ1f*MQ2f*MQ3f*MQ4f*MQ5f*MQ6f;

END$
```

LISTING 9b (VIEW 2)

```
NADER RIAHI
SENTINEL VISION INC.
NOV 1, 1988
1.00
A
EP900
DIGITAL CONTROLLER FOR THE APP/R, (V-2). PROTOII - PINOUT DIFFERS
OPTIONS: TURBO = ON

PART:EP900
INPUTS:
        CLOCK1@1,
        CLOCK2@21,
        PXCLOCK@38,
        COMPA@2,
        COMPB@3,
        HEAD@4,
        MENABLE@39

OUTPUTS:
        START@5,
        STOP@6,
        ENCONT@7,
        SQ0@15,
        SQ1@14,
        SQ2@13,
        SQ3@12,
        SQ4@11,
        SQ5@10,
        SQ6@9,
        SQ7@8,
        STOPEN@16,
        STARTE@25,
        STARTL@36,
        STOPL@35,
        MQ0@26,
        MQ1@27,
        MQ2@28,
        MQ3@29,
        MQ4@30,
        MQ5@31,
        MQ6@32,
        MQ7@33
```

NETWORK:
```
    CLOCK1=INP(CLOCK1)
    CLOCK2=INP(CLOCK2)
    COMPA=INP(COMPA)
    COMPB=INP(COMPB)
    HEAD=INP(HEAD)
    PXCLOCK=INP(PXCLOCK)
    MENABLE=INP(MENABLE)

START,STARTf=RORF(STARTd,STARTc,CLEAR,GND,VCC)
    STARTc=CLKB(STARTi)

STOP,STOPf=RORF(STOPd,STOPc,CLEAR,GND,VCC)
    STOPc=CLKB(STOPi)
    ENCONT,ENCONTf=RORF(ENCONTd,CLOCK1,CLEAR,GND,VCC)

SQ0,SQ0f=TOTF(SQ0t,CLOCK1,CLEAR,GND,VCC)
    SQ1,SQ1f=TOTF(SQ1t,CLOCK1,CLEAR,GND,VCC)
    SQ2,SQ2f=TOTF(SQ2t,CLOCK1,CLEAR,GND,VCC)
    SQ3,SQ3f=TOTF(SQ3t,CLOCK1,CLEAR,GND,VCC)
    SQ4,SQ4f=TOTF(SQ4t,CLOCK1,CLEAR,GND,VCC)
    SQ5,SQ5f=TOTF(SQ5t,CLOCK1,CLEAR,GND,VCC)
    SQ6,SQ6f=TOTF(SQ6t,CLOCK1,CLEAR,GND,VCC)
    SQ7,SQ7f=TOTF(SQ7t,CLOCK1,CLEAR,GND,VCC)

STARTE,STARTEf=TOTF(STARTEt,STARTEc,CLEAR,GND,VCC)
    STARTEc=CLKB(STARTEi)
    STOPEN,STOPENf=TOTF(STOPENt,STOPENc,CLEAR,GND,VCC)
    STOPENc=CLKB(STOPENi)

STARTL=RONF(STARTLd,STARTLc,CLEAR,GND,VCC)
    STARTLc=CLKB(STARTLi)
    STOPL=RONF(STOPLd,STOPLc,CLEAR,GND,VCC)
    STOPLc=CLKB(STOPLi)

MQ0,MQ0f=TOTF(MQ0t,CLOCK2,CLEAR,GND,VCC)
    MQ1,MQ1f=TOTF(MQ1t,CLOCK2,CLEAR,GND,VCC)
    MQ2,MQ2f=TOTF(MQ2t,CLOCK2,CLEAR,GND,VCC)
    MQ3,MQ3f=TOTF(MQ3t,CLOCK2,CLEAR,GND,VCC)
    MQ4,MQ4f=TOTF(MQ4t,CLOCK2,CLEAR,GND,VCC)
    MQ5,MQ5f=TOTF(MQ5t,CLOCK2,CLEAR,GND,VCC)
    MQ6,MQ6f=TOTF(MQ6t,CLOCK2,CLEAR,GND,VCC)
    MQ7,MQ7f=TOTF(MQ7t,CLOCK2,CLEAR,GND,VCC)
```

EQUATIONS:
```
    STARTd=STARTEf;
    STARTi=COMPA;
    STOPd=STOPENf;
    STOPi=COMPB;
    STARTEt=(( MQ0f*/MQ1f*/MQ2f*/MQ3f* MQ4f*/MQ5f*/MQ6f*/MQ7f*/HEAD)
           +(/MQ0f* MQ1f*/MQ2f* MQ3f*/MQ4f*/MQ5f*/MQ6f*/MQ7f*HEAD))
           */STARTEf;        %17 AND 10%
    STARTEi=/PXCLOCK;
    STOPENt=((/SQ0f*/SQ1f*/SQ2f* SQ3f*/SQ4f*/SQ5f* SQ6f*/SQ7f*/HEAD)
           +( SQ0f* SQ1f* SQ2f*/SQ3f*/SQ4f*/SQ5f* SQ6f*/SQ7f* HEAD))
           */STOPENf;        %72 AND 71%
    STOPENi=/PXCLOCK;
    ENCONTd=STARTf;
    STARTLd=(STARTf)
           +(/MQ0f* MQ1f*/MQ2f*/MQ3f*/MQ4f*/MQ5f*/MQ6f*/MQ7f);
    STARTLi=/PXCLOCK;
```

```
STOPLd=(STOPf)
      +(/MQ0f*/MQ1f* MQ2f* MQ3f* MQ4f* MQ5f* MQ6f*/MQ7f);
STOPLi=/PXCLOCK;
CLEAR=MENABLE;

SQ0t=ENCONTf;
SQ1t=ENCONTf*SQ0f;
SQ2t=ENCONTf*SQ0f*SQ1f;
SQ3t=ENCONTf*SQ0f*SQ1f*SQ2f;
SQ4t=ENCONTf*SQ0f*SQ1f*SQ2f*SQ3f;
SQ5t=ENCONTf*SQ0f*SQ1f*SQ2f*SQ3f*SQ4f;
SQ6t=ENCONTf*SQ0f*SQ1f*SQ2f*SQ3f*SQ4f*SQ5f;
SQ7t=ENCONTf*SQ0f*SQ1f*SQ2f*SQ3f*SQ4f*SQ5f*SQ6f;

MQ0t=/MENABLE;
MQ1t=/MENABLE*MQ0f;
MQ2t=/MENABLE*MQ0f*MQ1f;
MQ3t=/MENABLE*MQ0f*MQ1f*MQ2f;
MQ4t=/MENABLE*MQ0f*MQ1f*MQ2f*MQ3f;
MQ5t=/MENABLE*MQ0f*MQ1f*MQ2f*MQ3f*MQ4f;
MQ6t=/MENABLE*MQ0f*MQ1f*MQ2f*MQ3f*MQ4f*MQ5f;
MQ7t=/MENABLE*MQ0f*MQ1f*MQ2f*MQ3f*MQ4f*MQ5f*MQ6f;

END$
```

LISTING 9c
(VIEW 3)

```
NADER RIAHI/JAMES WONG
SENTINEL VISION INC.
NOV 1, 1988 /JAN 5, 1989
1.00
A
EP900
DIGITAL CONTROLLER FOR THE APP/R (V-3). PROTOII - PINOUT DIFFERS
OPTIONS: TURBO = ON

PART:EP900
INPUTS:
      CLOCK1@1,
      CLOCK2@21,
      PXCLOCK@38,
      COMPA@2,
      COMPB@3,
      HEAD@4,
      MENABLE@39

OUTPUTS:
      START@5,
      STOP@6,
      ENCONT@7,
      SQ0@15,
      SQ1@14,
      SQ2@13,
      SQ3@12,
      SQ4@11,
      SQ5@10,
      SQ6@9,
      SQ7@8,
```

```
        STOPEN@16,
        STARTE@25,
        STARTL@36,
        STOPL@35,
        MQ0@26,
        MQ1@27,
        MQ2@28,
        MQ3@29,
        MQ4@30,
        MQ5@31,
        MQ6@32,
        MQ7@33
NETWORK:
        CLOCK1=INP(CLOCK1)
        CLOCK2=INP(CLOCK2)
        COMPA=INP(COMPA)
        COMPB=INP(COMPB)
        HEAD=INP(HEAD)
        PXCLOCK=INP(PXCLOCK)
        MENABLE=INP(MENABLE)

START,STARTf=RORF(STARTd,STARTc,CLEAR,GND,VCC)
        STARTc=CLKB(STARTi)

STOP,STOPf=RORF(STOPd,STOPc,CLEAR,GND,VCC)
        STOPc=CLKB(STOPi)
        ENCONT,ENCONTf=RORF(ENCONTd,CLOCK1,CLEAR,GND,VCC)

SQ0,SQ0f=TOTF(SQ0t,CLOCK1,CLEAR,GND,VCC)
        SQ1,SQ1f=TOTF(SQ1t,CLOCK1,CLEAR,GND,VCC)
        SQ2,SQ2f=TOTF(SQ2t,CLOCK1,CLEAR,GND,VCC)
        SQ3,SQ3f=TOTF(SQ3t,CLOCK1,CLEAR,GND,VCC)
        SQ4,SQ4f=TOTF(SQ4t,CLOCK1,CLEAR,GND,VCC)
        SQ5,SQ5f=TOTF(SQ5t,CLOCK1,CLEAR,GND,VCC)
        SQ6,SQ6f=TOTF(SQ6t,CLOCK1,CLEAR,GND,VCC)
        SQ7,SQ7f=TOTF(SQ7t,CLOCK1,CLEAR,GND,VCC)

STARTE,STARTEf=TOTF(STARTEt,STARTEc,CLEAR,GND,VCC)
        STARTEc=CLKB(STARTEi)
        STOPEN,STOPENf=TOTF(STOPENt,STOPENc,CLEAR,GND,VCC)
        STOPENc=CLKB(STOPENi)

STARTL=RONF(STARTLd,STARTLc,CLEAR,GND,VCC)
        STARTLc=CLKB(STARTLi)
        STOPL=RONF(STOPLd,STOPLc,CLEAR,GND,VCC)
        STOPLc=CLKB(STOPLi)

MQ0,MQ0f=TOTF(MQ0t,CLOCK2,CLEAR,GND,VCC)
        MQ1,MQ1f=TOTF(MQ1t,CLOCK2,CLEAR,GND,VCC)
        MQ2,MQ2f=TOTF(MQ2t,CLOCK2,CLEAR,GND,VCC)
        MQ3,MQ3f=TOTF(MQ3t,CLOCK2,CLEAR,GND,VCC)
        MQ4,MQ4f=TOTF(MQ4t,CLOCK2,CLEAR,GND,VCC)
        MQ5,MQ5f=TOTF(MQ5t,CLOCK2,CLEAR,GND,VCC)
        MQ6,MQ6f=TOTF(MQ6t,CLOCK2,CLEAR,GND,VCC)
        MQ7,MQ7f=TOTF(MQ7t,CLOCK2,CLEAR,GND,VCC)

EQUATIONS:
        STARTd=STARTEf;
        STARTi=COMPA;
        STOPd=STOPENf;
        STOPi=COMPB;
```

```
STARTEt=((/MQ0f*/MQ1f*/MQ2f* MQ3f*/MQ4f* MQ5f*/MQ6f*/MQ7f*/HEAD)
       +(/MQ0f*/MQ1f*/MQ2f* MQ3f*/MQ4f* MQ5f*/MQ6f*/MQ7f* HEAD))
       */STARTEf;          %40 AND 40%
STARTEi=/PXCLOCK;
STOPENt=((/SQ0f*/SQ1f* SQ2f* SQ3f*/SQ4f*/SQ5f*/SQ6f*/SQ7f*/HEAD)
       +( /SQ0f*/SQ1f* SQ2f* SQ3f*/SQ4f*/SQ5f*/SQ6f*/SQ7f* HEAD))
       */STOPENf;          %12 AND 12 / USE TO BE 13 AND 13%
STOPENi=/PXCLOCK;
ENCONTd=STARTf;
STARTLd=(STARTf)
       +(/MQ0f* MQ1f*/MQ2f*/MQ3f*/MQ4f*/MQ5f*/MQ6f*/MQ7f);
STARTLi=/PXCLOCK;
STOPLd=(STOPf)
       +( MQ0f*/MQ1f* MQ2f* MQ3f* MQ4f* MQ5f* MQ6f*/MQ7f);
STOPLi=/PXCLOCK;
CLEAR=MENABLE;
SQ0t=ENCONTf;
SQ1t=ENCONTf*SQ0f;
SQ2t=ENCONTf*SQ0f*SQ1f;
SQ3t=ENCONTf*SQ0f*SQ1f*SQ2f;
SQ4t=ENCONTf*SQ0f*SQ1f*SQ2f*SQ3f;
SQ5t=ENCONTf*SQ0f*SQ1f*SQ2f*SQ3f*SQ4f;
SQ6t=ENCONTf*SQ0f*SQ1f*SQ2f*SQ3f*SQ4f*SQ5f;
SQ7t=ENCONTf*SQ0f*SQ1f*SQ2f*SQ3f*SQ4f*SQ5f*SQ6f;

MQ0t=/MENABLE;
MQ1t=/MENABLE*MQ0f;
MQ2t=/MENABLE*MQ0f*MQ1f;
MQ3t=/MENABLE*MQ0f*MQ1f*MQ2f;
MQ4t=/MENABLE*MQ0f*MQ1f*MQ2f*MQ3f;
MQ5t=/MENABLE*MQ0f*MQ1f*MQ2f*MQ3f*MQ4f;
MQ6t=/MENABLE*MQ0f*MQ1f*MQ2f*MQ3f*MQ4f*MQ5f;
MQ7t=/MENABLE*MQ0f*MQ1f*MQ2f*MQ3f*MQ4f*MQ5f*MQ6f;

END$

NADER RIAHI
SENTINEL VISION INC.
NOV 1, 1988
1.00
A
EP900
DIGITAL CONTROLLER FOR THE APP/R (V-4). PROTOII - PINOUT DIFFERS
OPTIONS: TURBO = ON

PART:EP900
INPUTS:
     CLOCK1@1,
     CLOCK2@21,
     PXCLOCK@38,
     COMPA@2,
     COMPB@3,
     HEAD@4,
     MENABLE@39

OUTPUTS:
     START@5,
     STOP@6,
     ENCONT@7,
     SQ0@15,
```

```
        SQ1@14,
        SQ2@13,
        SQ3@12,
        SQ4@11,
        SQ5@10,
        SQ6@9,
        SQ7@8,
        STOPEN@16,
        STARTE@25,
        STARTL@36,
        STOPL@35,
        MQ0@26,
        MQ1@27,
        MQ2@28,
        MQ3@29,
        MQ4@30,
        MQ5@31,
        MQ6@32,
        MQ7@33
NETWORK:
        CLOCK1=INP(CLOCK1)
        CLOCK2=INP(CLOCK2)
        COMPA=INP(COMPA)
        COMPB=INP(COMPB)
        HEAD=INP(HEAD)
        PXCLOCK=INP(PXCLOCK)
        MENABLE=INP(MENABLE)

START,STARTf=RORF(STARTd,STARTc,CLEAR,GND,VCC)
        STARTc=CLKB(STARTi)
        STOP,STOPf=RORF(STOPd,STOPc,CLEAR,GND,VCC)
        STOPc=CLKB(STOPi)
        ENCONT,ENCONTf=RORF(ENCONTd,CLOCK1,CLEAR,GND,VCC)

SQ0,SQ0f=TOTF(SQ0t,CLOCK1,CLEAR,GND,VCC)
        SQ1,SQ1f=TOTF(SQ1t,CLOCK1,CLEAR,GND,VCC)
        SQ2,SQ2f=TOTF(SQ2t,CLOCK1,CLEAR,GND,VCC)
        SQ3,SQ3f=TOTF(SQ3t,CLOCK1,CLEAR,GND,VCC)
        SQ4,SQ4f=TOTF(SQ4t,CLOCK1,CLEAR,GND,VCC)
        SQ5,SQ5f=TOTF(SQ5t,CLOCK1,CLEAR,GND,VCC)
        SQ6,SQ6f=TOTF(SQ6t,CLOCK1,CLEAR,GND,VCC)
        SQ7,SQ7f=TOTF(SQ7t,CLOCK1,CLEAR,GND,VCC)

STARTE,STARTEf=TOTF(STARTEt,STARTEc,CLEAR,GND,VCC)
        STARTEc=CLKB(STARTEi)
        STOPEN,STOPENf=TOTF(STOPENt,STOPENc,CLEAR,GND,VCC)
        STOPENc=CLKB(STOPENi)

STARTL=RONF(STARTLd,STARTLc,CLEAR,GND,VCC)
        STARTLc=CLKB(STARTLi)
        STOPL=RONF(STOPLd,STOPLc,CLEAR,GND,VCC)
        STOPLc=CLKB(STOPLi)

MQ0,MQ0f=TOTF(MQ0t,CLOCK2,CLEAR,GND,VCC)
        MQ1,MQ1f=TOTF(MQ1t,CLOCK2,CLEAR,GND,VCC)
        MQ2,MQ2f=TOTF(MQ2t,CLOCK2,CLEAR,GND,VCC)
        MQ3,MQ3f=TOTF(MQ3t,CLOCK2,CLEAR,GND,VCC)
        MQ4,MQ4f=TOTF(MQ4t,CLOCK2,CLEAR,GND,VCC)
        MQ5,MQ5f=TOTF(MQ5t,CLOCK2,CLEAR,GND,VCC)
        MQ6,MQ6f=TOTF(MQ6t,CLOCK2,CLEAR,GND,VCC)
        MQ7,MQ7f=TOTF(MQ7t,CLOCK2,CLEAR,GND,VCC)
```

EQUATIONS:
```
    STARTd=STARTEf;
    STARTi=COMPA;
    STOPd=STOPENf;
    STOPi=COMPB;
    STARTEt=(( MQ0f*/MQ1f* MQ2f* MQ3f*/MQ4f*/MQ5f*/MQ6f*/MQ7f*/HEAD)
            +(/MQ0f* MQ1f*/MQ2f* MQ3f*/MQ4f*/MQ5f*/MQ6f*/MQ7f* HEAD))
            */STARTEf;         %13 AND 10%
    STARTEi=/PXCLOCK;
    STOPENt=(( SQ0f*/SQ1f*/SQ2f*/SQ3f*/SQ4f*/SQ5f* SQ6f*/SQ7f*/HEAD)
            +( SQ0f* SQ1f* SQ2f* SQ3f* SQ4f* SQ5f*/SQ6f*/SQ7f* HEAD))
            */STOPENf;         %65 AND 63%
    STOPENi=/PXCLOCK;
    ENCONTd=STARTf;
    STARTLd=(STARTf)
            +(/MQ0f* MQ1f*/MQ2f*/MQ3f*/MQ4f*/MQ5f*/MQ6f*/MQ7f);
    STARTLi=/PXCLOCK;
    STOPLd=(STOPf)
            +(/MQ0f* MQ1f*/MQ2f*/MQ3f*/MQ4f*/MQ5f*/MQ6f*/MQ7f);
    STOPLi=/PXCLOCK;
    CLEAR=MENABLE;

SQ0t=ENCONTf;
    SQ1t=ENCONTf*SQ0f;
    SQ2t=ENCONTf*SQ0f*SQ1f;
    SQ3t=ENCONTf*SQ0f*SQ1f*SQ2f;
    SQ4t=ENCONTf*SQ0f*SQ1f*SQ2f*SQ3f;
    SQ5t=ENCONTf*SQ0f*SQ1f*SQ2f*SQ3f*SQ4f;
    SQ6t=ENCONTf*SQ0f*SQ1f*SQ2f*SQ3f*SQ4f*SQ5f;
    SQ7t=ENCONTf*SQ0f*SQ1f*SQ2f*SQ3f*SQ4f*SQ5f*SQ6f;

MQ0t=/MENABLE;
    MQ1t=/MENABLE*MQ0f;
    MQ2t=/MENABLE*MQ0f*MQ1f;
    MQ3t=/MENABLE*MQ0f*MQ1f*MQ2f;
    MQ4t=/MENABLE*MQ0f*MQ1f*MQ2f*MQ3f;
    MQ5t=/MENABLE*MQ0f*MQ1f*MQ2f*MQ3f*MQ4f;
    MQ6t=/MENABLE*MQ0f*MQ1f*MQ2f*MQ3f*MQ4f*MQ5f;
    MQ7t=/MENABLE*MQ0f*MQ1f*MQ2f*MQ3f*MQ4f*MQ5f*MQ6f;

END$

AL KLEINSCHMIDT
SENTINEL VISION INC.
04/03/88
1.00
A
EP900
P2INTF.ADF
CONTROLLER FOR APP-DSP INTERFACE - LOCAL - PROTOII.

OPTIONS: TURBO = ON

PART: EP900

INPUTS:

CLOCK0@1,
    CLOCK1@21,
    EOS@3,         % end of scan %
```

```
        OVERIDE@4,      % overide request from dsp %
        IOE@17,         % I/O expansion control signal from dsp %
        RW@18,          % read /write control from dsp %
        A0@19,          % lsb of four address lines from dsp %
        A1@22,
        A2@23,
        A3@24,
        ABSdsp@37       % dsp selects memory bank during an overide condition %
        ABSapp@38,      % bank select from app ; given during normal op %

OUTPUTS:

RWS@5,          % controls direction of data transfer wrt dsp %
        ABSEL@6,        % conditioned bank select %
        WRB@7,          % write to bank B %
        OEB@8,          % b bank oe %
        IOEWR2@9,       % during overide, data is written to the interface %
                        % from the dsp via this port %
        IOEWR0@36,      % used to delay IOEWR2 %
        IOERD2@10,      % data read from interface via this port %
        EOC@12,         % end of latch count %
        CLEAR@13,       % used to clear hi order address bits %
        CLOCK8@14,
        CLOCK4@15,      % divided clock %
        CLOCK2@16,
        C15@25,         % for demux input for app 1 of 16 latch select %
        C14@26,
        C13@27,
        C12@28,
        C@11,
        RWNUM@29,       % clocks counter for dsp address generation %
        RDOE@30,        % enables the IOERD2 port %
        JKRWS@31,       % latched read/write select %
        OEA@32,         % a bank oe %
        WRA@33,         % write to bank A %
        IOERD1@34,      % port contains app and interface status %
        IOEWR1@35,      % port contains commands from dsp to interface %

NETWORK:

CLOCK0=INP(CLOCK0)
        CLOCK1=INP(CLOCK1)
        CLOCKa=CLKB(CLOCK8f)            % drives the high order address bits %
        CLOCKb=CLKB(INVEOS)
        EOS=INP(EOS)
        OVERIDE=INP(OVERIDE)
        ABSapp=INP(ABSapp)
        ABSdsp=INP(ABSdsp)
        IOE=INP(IOE)
        RW=INP(RW)
        A0=INP(A0)
        A1=INP(A1)
        A2=INP(A2)
        A3=INP(A3)

CLOCK8,CLOCK8f=TOTF(CLOCK8t,CLOCK0,GND,GND,VCC)
        CLOCK4,CLOCK4f=TOTF(CLOCK4t,CLOCK0,GND,GND,VCC)
        CLOCK2,CLOCK2f=TOTF(VCC,CLOCK0,GND,GND,VCC)
        C15,C15f=TOTF(C15t,CLOCKa,GND,GND,VCC)
```

```
C14,C14f=TOTF(C14t,CLOCKa,GND,GND,VCC)
C13,C13f=TOTF(C13t,CLOCKa,GND,GND,VCC)
C12,C12f=TOTF(C12t,CLOCKa,GND,GND,VCC)
C,Cf=TOTF(Ct,CLOCKa,GND,GND,VCC)
EOC,EOCf=TOTF(EOCt,CLOCKa,GND,GND,VCC)
CLEAR,CLEARf=RORF(CLEARd,CLOCKb,RESET,GND,VCC)
IOERD1=CONF(IOERD1c,VCC)
IOEWR1=CONF(IOEWR1c,VCC)
IOEWR2=CONF(IOEWR2c,VCC)
IOEWR0,IOEWR0f=COIF(IOEWR0c,VCC)
IOERD2=CONF(IOERD2c,VCC)
WRA=CONF(WRAc,VCC)
OEA=RONF(OEAd,CLOCK1,GND,GND,VCC)
WRB=CONF(WRBc,VCC)
OEB=RONF(OEBd,CLOCK0,GND,GND,VCC)
JKRWS,JKRWSf=JOJF(JKRWSj,CLOCK1,JKRWSk,GND,GND,VCC)
RWS,RWSf=COIF(RWSc,VCC)
RDOE=CONF(RDOEc,VCC)
RWNUM=CONF(RWNUMc,VCC)
ABSEL=RONF(ABSELd,CLOCK0,GND,GND,VCC)

EQUATIONS:

CLOCK4t = CLOCK2f;   % divides 12MHz input clock by 8 to 1.5 MHz %
    CLOCK8t = CLOCK4f;

Ct =    /CLEARf*/EOCf
           +  EOCf * /Cf
           +  CLEARf * Cf;
                              % high order address generation %

C12t =  /CLEARf*/EOCf* Cf
           +  CLEARf * C12f;
      C13t =  /CLEARf*/EOCf* Cf * C12f
           +  CLEARf * C13f;
      C14t =  /CLEARf*/EOCf* Cf * C12f * C13f
           +  CLEARf * C14f;
      C15t =  /CLEARf*/EOCf* Cf * C12f * C13f * C14f
           +  CLEARf * C15f;
      EOCt =  /CLEARf*/EOCf*/Cf * C12f * C13f * C14f * C15f
           +  CLEARf * EOCf;

INVEOS = /EOS;        % used as CLOCKb %

CLEARd = EOCf;        % used to clear the Q 's synchronously %

RESET  = /EOCf;

ABSELd =   /OVERIDE * ABSapp
            +   OVERIDE */ABSdsp;

WRAc = /( /OVERIDE * ABSapp */Cf */CLOCK8f
           + ( OVERIDE * ABSdsp * JKRWSf));

WRBc = /( /OVERIDE */ABSapp */Cf */CLOCK8f
           + ( OVERIDE */ABSdsp * JKRWSf));
```

```
OEAd  =  /((/OVERIDE */ABSapp)
         + ( OVERIDE * ABSdsp * /JKRWSf));

OEBd  =  /((/OVERIDE * ABSapp)
         + ( OVERIDE */ABSdsp * /JKRWSf));

IOEWR0c =  ( /IOE * /RW * A0 * /A1 * /A2 * A3);    % write port 09H %
IOEWR2c =  IOEWR0f;
IOERD2c =  RWSf;                                    % read port 09H %
IOEWR1c =  /IOE * /RW * /A0 * /A1 * /A2 * A3;       % write port 08H %
IOERD1c =  /(/IOE * RW * /A0 * /A1 * /A2 * A3);     % read port 08H %

RWNUMc =   IOEWR0f
         + RWSf;

RWSc  =    /IOE * RW * A0 * /A1 * /A2 * A3  ;   % low for read - %
                                                % RW = 1 %
RDOEc =    /RWSf;

JKRWSj =   /IOE * /RW * A0 * /A1 * /A2 * A3;   % high for write %
JKRWSk =   /IOE * RW * A0 * /A1 * /A2 * A3;    % in order to latch -%
           % ep clock must have period less than 150 nsec %

END$
```

We claim:

1. Apparatus for detecting an irregularity in the surface of an elongated seam having a curvate surface cross-section, said apparatus comprising:
   (a) irradiation means for irradiating said surface to produce reflected signals;
   (b) a plurality of radiation sensors, each being disposed to have a selected field of view of the surface, each such view being defined by a width extending longitudinally of said seam and a length curvately extending in a plane lying transverse to the longitudinal direction of said seam; each such sensor for receiving such portion of said reflected signals as are reflected within its corresponding field of view and for producing corresponding sensor output signals in response thereto;
   (c) signal processing means for receiving said sensor output signals for a succession of fields of view along the longitudinal length of said seam, and for deriving therefrom signal data representing a dimensional feature of said seam; and,
   (d) signal comparison means for comparing said signal data with signal data representing an acceptable dimensional limit, and for producing a rejection signal in the event that said dimensional feature does not fall within said limit.

2. Apparatus as defined in claim 1, wherein said signal data representing an acceptable dimensional limit is derived by said signal processing means from said sensor output signals.

3. Apparatus as defined in claim 2, further including classification means for characterizing the nature of the irregularity if said dimensional feature does not fall within said limit.

4. Apparatus as defined in claim 1, 2 or 3, including means for longitudinally moving said seam through the field of view of said sensors.

5. Apparatus as defined in claim 2, wherein said seam is a longitudinally circular double seam joining the lid and body of a can.

6. Apparatus as defined in claim 5, including transport means for rotating said can to longitudinally move said seam through the field of view of said sensors.

7. Apparatus as defined in claim 5, including transport means for lifting said can to move said seam into the field of view of said sensors and for rotating said can to longitudinally move said seam through the field of view of said sensors.

8. Apparatus as defined in claim 6, wherein said transport means comprises:
   (a) an inspection rotor and means for rotating same about a fixed vertically extending central axis; said sensors being mounted to said rotor so as to rotate therewith; and,
   (b) a rotatable inspection platform mounted to said rotor to support said can in an upright position radially away from said central axis, and means for rotating said platform with said can in a direction of rotation opposite to that of said rotor about a planetary axis extending parallel to said central axis.

9. Apparatus as defined in claim 5, 6 or 8, comprising four of said sensors, wherein:
   (a) a first one of said sensors is disposed to have a field of view looking upwardly and radially inwardly at said seam;
   (b) a second one of said sensors is disposed to have a field of view horizontally inwardly at said seam;
   (c) a third one of said sensors is disposed to have a field of view looking vertically downwardly at said seam; and,
   (d) a fourth one of said sensors is disposed to have a field of view looking downwardly and radially outwardly at said seam.

10. Apparatus as defined in claim 2, wherein said signal processing means comprises, for each of said sensors, an associated means for deriving data on length for each of said succession of fields of view, such data on length relating to the transverse length of said seam as viewed by the corresponding sensor.

11. Apparatus as defined in claim 10, wherein said signal comparison means comprises, for each of said sensors, an associated means for comparing data on length as derived for one of said succession of fields of view with data on length derived for another one of said fields of view, and means for recording a deviation if any difference in such data exceeds a predetermined threshold.

12. Apparatus as defined in claim 11, including means for removing noise from said data prior to said data comparison.

13. Apparatus as defined in claim 10, 11, or 12, further including classification means for characterizing the nature of the irregularity if said dimensional feature does not fall within said limit.

* * * * *